US011104673B2

(12) United States Patent
Flygare et al.

(10) Patent No.: US 11,104,673 B2
(45) Date of Patent: Aug. 31, 2021

(54) QUATERNARY AMINE COMPOUNDS AND ANTIBODY-DRUG CONJUGATES THEREOF

(71) Applicant: Genentech, Inc., South San Francisco, CA (US)

(72) Inventors: John A. Flygare, Burlingame, CA (US); Thomas Pillow, San Francisco, CA (US); Leanna Staben, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 16/697,706

(22) Filed: Nov. 27, 2019

(65) Prior Publication Data
US 2020/0087297 A1 Mar. 19, 2020

Related U.S. Application Data

(60) Division of application No. 15/583,492, filed on May 1, 2017, now Pat. No. 10,556,895, which is a continuation of application No. PCT/US2015/063538, filed on Dec. 2, 2015.

(60) Provisional application No. 62/087,127, filed on Dec. 3, 2014.

(51) Int. Cl.
| | | |
|---|---|---|
| *A61K 39/00* | (2006.01) | |
| *C07D 417/14* | (2006.01) | |
| *C07D 403/14* | (2006.01) | |
| *C07D 403/12* | (2006.01) | |
| *C07D 471/02* | (2006.01) | |
| *A61K 47/68* | (2017.01) | |

(52) U.S. Cl.
CPC ......... *C07D 417/14* (2013.01); *C07D 403/12* (2013.01); *C07D 403/14* (2013.01); *C07D 471/02* (2013.01); *A61K 47/6803* (2017.08); *A61K 47/6805* (2017.08); *A61K 47/6851* (2017.08); *A61K 47/6889* (2017.08)

(58) Field of Classification Search
CPC ................................................ A61K 47/6851
See application file for complete search history.

(56) References Cited

U.S. PATENT DOCUMENTS

| | | | |
|---|---|---|---|
| 5,024,835 A | 6/1991 | Rao et al. | |
| 6,214,345 B1 | 4/2001 | Firestone et al. | |
| 7,223,837 B2 | 5/2007 | De Groot et al. | |
| 7,521,541 B2 | 4/2009 | Eigenbrot et al. | |
| 2009/0318668 A1 | 12/2009 | Beusker et al. | |
| 2014/0030281 A1* | 1/2014 | Polakis | A61K 47/6867 424/181.1 |
| 2016/0279260 A1* | 9/2016 | Flygare | A61P 35/02 |
| 2016/0279261 A1* | 9/2016 | Lee | A61P 31/00 |
| 2016/0310611 A1* | 10/2016 | Flygare | A61K 47/6867 |
| 2017/0232113 A1 | 8/2017 | Flygare et al. | |

FOREIGN PATENT DOCUMENTS

| | | | | |
|---|---|---|---|---|
| EP | 0328446 A1 | 8/1989 | | |
| WO | 2007038658 A2 | 4/2007 | | |
| WO | 2009099741 A1 | 8/2009 | | |
| WO | 2010009124 A2 | 1/2010 | | |
| WO | 2012166560 A1 | 12/2012 | | |
| WO | 2013068874 A1 | 5/2013 | | |
| WO | 2013149159 A1 | 10/2013 | | |
| WO | 2013165940 A1 | 11/2013 | | |
| WO | 2013177055 A2 | 11/2013 | | |
| WO | 2013185117 A1 | 12/2013 | | |
| WO | 2013192360 A1 | 12/2013 | | |
| WO | 2014092804 A1 | 6/2014 | | |
| WO | 2014100762 A1 | 6/2014 | | |
| WO | 2014193722 A1 | 12/2014 | | |
| WO | 2014194247 A1 | 12/2014 | | |
| WO | 2015023355 A1 | 2/2015 | | |
| WO | 2015095124 A1 | 6/2015 | | |
| WO | 2015095223 A2 | 6/2015 | | |
| WO | 2015095227 A2 | 6/2015 | | |
| WO | WO-2015095124 A1 * | 6/2015 | ......... | A61K 47/6867 |
| WO | WO-2015095223 A2 * | 6/2015 | ......... | A61K 47/6849 |
| WO | WO-2015095227 A2 * | 6/2015 | .............. | A61P 31/00 |
| WO | 2016040684 A1 | 3/2016 | | |
| WO | WO-2016040684 A1 * | 3/2016 | ......... | A61K 47/6889 |

OTHER PUBLICATIONS

Cohen, R, et al., "Development of Novel ADCs: Conjugation of Tubulysin Analogues to Trastuzumab Monitored by Dual Radiolabeling", Cancer Res 74(20), 5700-5710 (2014).
Dokter, W, et al., "Novel HER2 targeting antibody-drug conjugates based on DNA-interacting duocarmycin and an unique linker technology with great potential in breast cancer and NSCLC", Cancer Research, Abstract 4329, Proceedings: AACR 104th Annual Meeting, Washington, DC, Apr. 6-10, 2013. [Retrieved from Internet: URL:tyyp://cancerres.aacrjournals.org/cgi/content/meeting_abstract/73/8_MeetingAbstracts/439].
Dokter, W, et al., "Preclinical profile of the HER2-targeting ADC SYD983/SYD985; introduction of a new duocarmycin-based linker-drug platform", Mol Cancer Ther 13(11), 2618-2629 (2014).
Doronina, S, et al., "Development of potent monoclonal antibody auristatin conjugates for cancer therapy", Nat Biotechnol 21, 778-784 (2003).
Doronina, S, et al., "Novel Peptide Linkers for Highly Potent Antibody—Auristatin Conjugate", Bioconjugate Chem 19, 1960-1963 (2008).
Dubowchik, G, et al., "Cathepsin B-Labile Dipeptide Linkers for Lysosomal Release of Doxorubicin from Internalizing Immunoconjugates: Model Studies of Enzymatic Drug Release and Antigen-Specific in Vitro Anticancer Activity", Bioconjugate Chem 13, 855-869 (2002).

(Continued)

*Primary Examiner* — Matthew P Coughlin
(74) *Attorney, Agent, or Firm* — Viksnins Harris Padys Malen LLP

(57) ABSTRACT

This invention relates to quaternary amine linkers and anti-body drug conjugates thereof, to pharmaceutical compositions containing them, and to their use in therapy for the prevention or treatment of cancer.

18 Claims, 1 Drawing Sheet
Specification includes a Sequence Listing.

(56) References Cited

OTHER PUBLICATIONS

Dubowchik, G, et al., "Cathepsin B-Sensitive Dipeptide Prodrugs. 1. A Model Study of Structural Requirements for Efficient Release of Doxorubicin", Bioorganic & Medicinal Chemistry Letters 8, 3341-3346 (1998).

Dubowchik, G, et al., "Doxorubicin Immunoconjugates Containing Bivalent, Lysosomally-Cleavable Dipeptide Linkages", Bioorganic & Medicinal Chemistry Letters 12, 1529-1532 (2002).

Ducry, L, et al., "Antibody-Drug Conjugates: Linking Cytotoxic Payloads to Monoclonal Antibodies", Bioconjugate Chem 21, 5-13 (2010).

Flygare, J, et al., "Antibody-Drug Conjugates for the Treatment of Cancer", Chem Biol Drug Des 81, 113-121 (2013).

Junutula, J, et al., "Rapid identification of reactive cysteine residues for site-specific labeling of antibody—Fabs", Journal of Immunological Methods 332, 41-52 (2008).

Junutula, J, et al., "Site-specific conjugation of a cytotoxic drug to an antibody improves the therapeutic index", Nature Biotechnology 26(8), 925-932 (2008).

Patent Cooperation Treaty, International Searching Authority, Search Report and Written Opinion for PCT/US2015/063538, 17 pages, dated Mar. 3, 2016.

Staben, L, et al., "Stabilizing a Tubulysin Antibody—Drug Conjugate to Enable Activity Against Multidrug-Resistant Tumors", ACS Med Chem Lett 8, 1037-1041 (2017).

Staben, L, et al., "Targeted drug delivery through the traceless release of tertiary and heteroaryl amines from antibody-drug conjugates", Nature Chemistry 8, 1112-1119 (2016).

Suzawa, T, et al., "Synthesis and HPLC analysis of enzymatically cleavable linker consisting of poly(ethylene glycol) and dipeptide for the development of immunoconjugate", Journal of Controlled Release 69(1), 27-41 (2000).

Wei, B, et al., "Discovery of Peptidomimetic Antibody-Drug Conjugate Linkers with Enhanced Protease Specificity", J Med Chem 61, 989-1000 (2018).

* cited by examiner

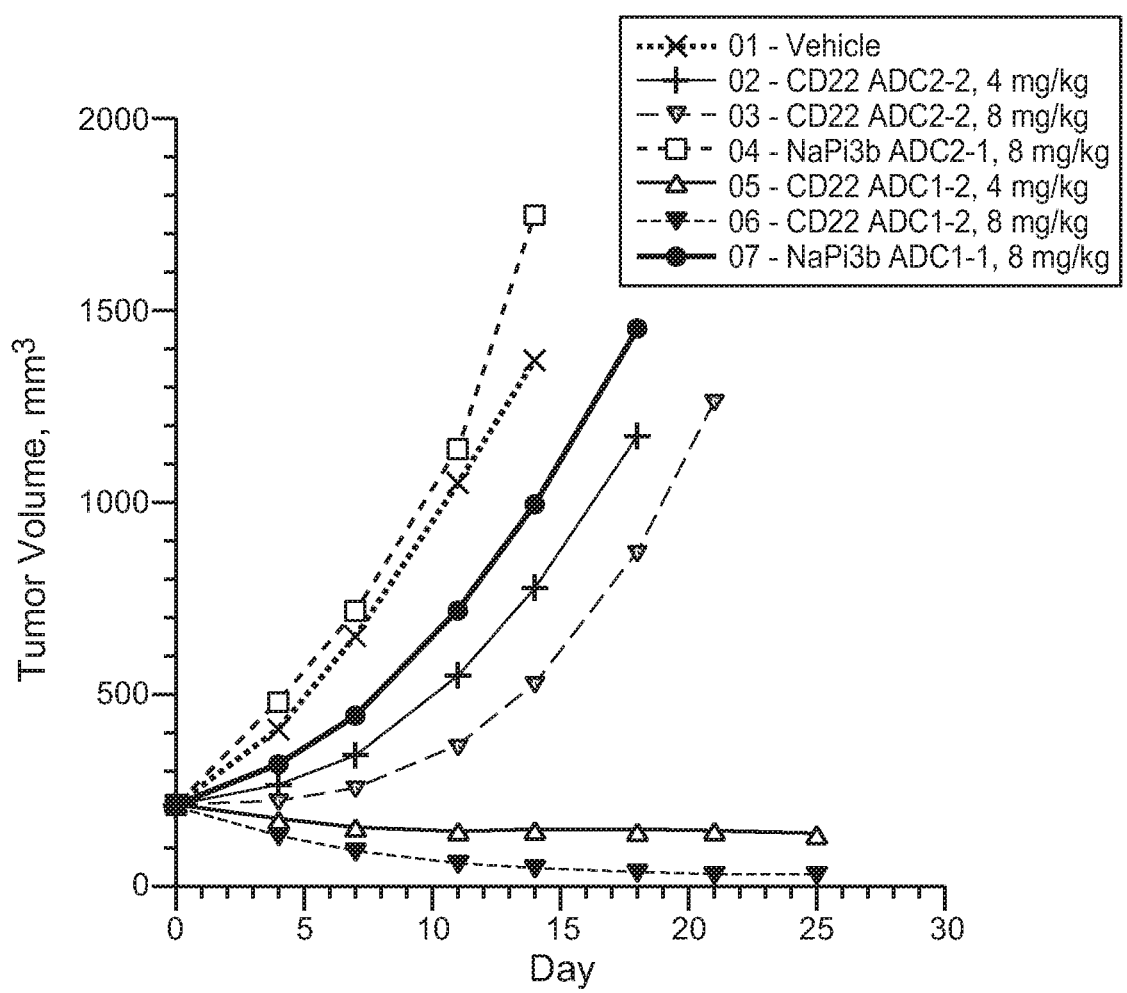

SEQUENCE LISTING

```
<160> NUMBER OF SEQ ID NOS: 50

<210> SEQ ID NO 1
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Arg Ser Ser Glu Thr Leu Val His Ser Ser Gly Asn Thr Tyr Leu Glu
1               5                   10                  15

<210> SEQ ID NO 2
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Arg Val Ser Asn Arg Phe Ser
1               5

<210> SEQ ID NO 3
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Phe Gln Gly Ser Phe Asn Pro Leu Thr
1               5

<210> SEQ ID NO 4
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Gly Phe Ser Phe Ser Asp Phe Ala Met Ser
1               5                   10

<210> SEQ ID NO 5
<211> LENGTH: 18
<212> TYPE: PRT
<213> ORGANISM: Artificial Sequence
<220> FEATURE:
<221> NAME/KEY: source
```

<223> OTHER INFORMATION: /note="Description of Artificial Sequence:
     Synthetic peptide"

<400> SEQUENCE: 5

Ala Thr Ile Gly Arg Val Ala Phe His Thr Tyr Tyr Pro Asp Ser Met
1               5                   10                  15

Lys Gly

<210> SEQ ID NO 6
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic peptide"

<400> SEQUENCE: 6

Ala Arg His Arg Gly Phe Asp Val Gly His Phe Asp Phe
1               5                   10

<210> SEQ ID NO 7
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ser Ser Glu Thr Leu Val His Ser
            20                  25                  30

Ser Gly Asn Thr Tyr Leu Glu Trp Tyr Gln Gln Lys Pro Gly Lys Ala
        35                  40                  45

Pro Lys Leu Leu Ile Tyr Arg Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Phe Gln Gly
                85                  90                  95

Ser Phe Asn Pro Leu Thr Phe Gly Gln Gly Thr Lys Val Glu Ile Lys
            100                 105                 110

Arg

<210> SEQ ID NO 8
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp Phe
            20                  25                  30

Ala Met Ser Trp Val Arg Gln Ala Pro Gly Lys Gly Leu Glu Trp Val

```
                35                  40                  45
Ala Thr Ile Gly Arg Val Ala Phe His Thr Tyr Tyr Pro Asp Ser Met
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg His Arg Gly Phe Asp Val Gly His Phe Asp Phe Trp Gly Gln
            100                 105                 110

Gly Thr Leu Val Thr Val Ser Ser
            115                 120

<210> SEQ ID NO 9
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Asp Ile Gln Met Thr Gln Ser Pro Ser Ser Leu Ser Ala Ser Val Gly
  1               5                  10                  15

Asp Arg Val Thr Ile Thr Cys Arg Ser Ser Glu Thr Leu Val His Ser
                20                  25                  30

Ser Gly Asn Thr Tyr Leu Glu Trp Tyr Gln Gln Lys Pro Gly Lys Ala
            35                  40                  45

Pro Lys Leu Leu Ile Tyr Arg Val Ser Asn Arg Phe Ser Gly Val Pro
 50                  55                  60

Ser Arg Phe Ser Gly Ser Gly Ser Gly Thr Asp Phe Thr Leu Thr Ile
 65                  70                  75                  80

Ser Ser Leu Gln Pro Glu Asp Phe Ala Thr Tyr Tyr Cys Phe Gln Gly
                85                  90                  95

Ser Phe Asn Pro Leu Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 10
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic polypeptide"

<400> SEQUENCE: 10

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp Phe
            20                  25                  30

Ala Met Ser Trp Val Arg Gln Ala Pro Gly Lys Gly Leu Glu Trp Val
        35                  40                  45

Ala Thr Ile Gly Arg Val Ala Phe His Thr Tyr Tyr Pro Asp Ser Met
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Arg Gly Phe Asp Val Gly His Phe Asp Phe Trp Gly Gln
            100                 105                 110

Gly Thr Leu Val Thr Val Ser Ser Cys Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400
```

```
Leu Asp Ser Asp Gly Ser Phe Phe Leu Tyr Ser Lys Leu Thr Val Asp
            405                 410                 415
Lys Ser Arg Trp Gln Gln Gly Asn Val Phe Ser Cys Ser Val Met His
        420                 425                 430
Glu Ala Leu His Asn His Tyr Thr Gln Lys Ser Leu Ser Leu Ser Pro
    435                 440                 445
Gly Lys
    450

<210> SEQ ID NO 11
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Arg Ser Ser Gln Ser Leu Leu His Ser Asn Gly Tyr Asn Tyr Leu Asp
1               5                   10                  15

<210> SEQ ID NO 12
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Leu Gly Val Asn Ser Val Ser
1               5

<210> SEQ ID NO 13
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Met Gln Ala Leu Gln Thr Pro Trp Thr
1               5

<210> SEQ ID NO 14
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Asn His Ala Ile Ser
1               5

<210> SEQ ID NO 15
<211> LENGTH: 17
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic peptide"

<400> SEQUENCE: 15

Gly Ile Ile Pro Ile Phe Gly Thr Ala Asn Tyr Ala Gln Lys Phe Gln
1               5                   10                  15

Gly

<210> SEQ ID NO 16
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Glu Trp Ala Asp Val Phe Asp Ile
1               5

<210> SEQ ID NO 17
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Glu Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Val Asn Ser Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110

<210> SEQ ID NO 18
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ile Phe Ser Asn His
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
            50                  55                  60

Gln Gly Arg Val Thr Ile Thr Ala Asp Glu Ser Thr Ser Thr Ala Phe
 65                  70                  75                  80

Met Glu Leu Ser Ser Leu Arg Ser Glu Asp Thr Ala Val Tyr Tyr Cys
                 85                  90                  95

Ala Arg Glu Trp Ala Asp Val Phe Asp Ile Trp Gly Gln Gly Thr Met
             100                 105                 110

Val Thr Val Ser Ser
        115

<210> SEQ ID NO 19
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Arg Ala Ser Gln Gly Ile Arg Asn Asp Leu Gly
1               5                   10

<210> SEQ ID NO 20
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Ala Ala Ser Ser Leu Gln Ser
1               5

<210> SEQ ID NO 21
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Leu Gln His Asn Ser Tyr Pro Trp Thr
1               5

<210> SEQ ID NO 22
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Gly Asn Tyr Met Ser
1               5

<210> SEQ ID NO 23
<211> LENGTH: 16
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Leu Ile Tyr Ser Gly Asp Ser Thr Tyr Tyr Ala Asp Ser Val Lys Gly
1               5                   10                  15

<210> SEQ ID NO 24
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Asp Gly Tyr Tyr Val Ser Asp Met Val Val
1               5                   10

<210> SEQ ID NO 25
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Leu Glu Ile Lys
            100                 105

<210> SEQ ID NO 26
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Glu Val Gln Leu Val Glu Ser Gly Gly Ala Leu Ile Gln Pro Gly Gly
1               5                   10                  15

Ser Leu Arg Leu Ser Cys Val Ala Ser Gly Phe Thr Ile Ser Gly Asn
                20                  25                  30

Tyr Met Ser Trp Val Arg Gln Ala Pro Gly Lys Gly Leu Glu Trp Val
            35                  40                  45
```

```
Ser Leu Ile Tyr Ser Gly Asp Ser Thr Tyr Tyr Ala Asp Ser Val Lys
    50                  55                  60

Gly Arg Phe Asn Ile Ser Arg Asp Ile Ser Lys Asn Thr Val Tyr Leu
65                  70                  75                  80

Gln Met Asn Ser Leu Arg Val Glu Asp Thr Ala Val Tyr Tyr Cys Val
                85                  90                  95

Arg Asp Gly Tyr Tyr Val Ser Asp Met Val Val Trp Gly Lys Gly Thr
            100                 105                 110

Thr Val Thr Val Ser Ser
            115
```

```
<210> SEQ ID NO 27
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Leu Glu Ile Lys
            100                 105
```

```
<210> SEQ ID NO 28
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

Glu Val Gln Leu Val Glu Ser Gly Gly Ala Leu Ile Gln Pro Gly Gly
1               5                   10                  15

Ser Leu Arg Leu Ser Cys Val Ala Ser Gly Phe Thr Ile Ser Gly Asn
            20                  25                  30

Tyr Met Ser Trp Val Arg Gln Ala Pro Gly Lys Gly Leu Glu Trp Val
        35                  40                  45

Ser Leu Ile Tyr Ser Gly Asp Ser Thr Tyr Tyr Ala Asp Ser Val Lys
    50                  55                  60

Gly Arg Phe Thr Ile Ser Arg Asp Ile Ser Lys Asn Thr Val Tyr Leu
65                  70                  75                  80

Gln Met Asn Ser Leu Arg Val Glu Asp Thr Ala Val Tyr Tyr Cys Val
                85                  90                  95
```

```
Arg Asp Gly Tyr Tyr Val Ser Asp Met Val Val Trp Gly Lys Gly Thr
                100                 105                 110

Thr Val Thr Val Ser Ser
        115

<210> SEQ ID NO 29
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Leu Glu Ile Lys
                100                 105

<210> SEQ ID NO 30
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Glu Val Gln Leu Val Glu Ser Gly Gly Ala Leu Ile Gln Pro Gly Gly
1               5                   10                  15

Ser Leu Arg Leu Ser Cys Val Ala Ser Gly Phe Thr Ile Ser Gly Asn
            20                  25                  30

Tyr Met Ser Trp Val Arg Gln Ala Pro Gly Lys Gly Leu Glu Trp Val
        35                  40                  45

Ser Leu Ile Tyr Ser Gly Asp Ser Thr Tyr Tyr Ala Asp Ser Val Lys
    50                  55                  60

Gly Arg Phe Ser Ile Ser Arg Asp Ile Ser Lys Asn Thr Val Tyr Leu
65                  70                  75                  80

Gln Met Asn Ser Leu Arg Val Glu Asp Thr Ala Val Tyr Tyr Cys Val
                85                  90                  95

Arg Asp Gly Tyr Tyr Val Ser Asp Met Val Val Trp Gly Lys Gly Thr
                100                 105                 110

Thr Val Thr Val Ser Ser
        115

<210> SEQ ID NO 31
<211> LENGTH: 107
<212> TYPE: PRT
```

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 31

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Leu Glu Ile Lys
            100                 105
```

<210> SEQ ID NO 32
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 32

```
Glu Val Gln Leu Val Glu Ser Gly Gly Ala Leu Ile Gln Pro Gly Gly
1               5                   10                  15

Ser Leu Arg Leu Ser Cys Val Ala Ser Gly Phe Thr Ile Ser Gly Asn
            20                  25                  30

Tyr Met Ser Trp Val Arg Gln Ala Pro Gly Lys Gly Leu Glu Trp Val
        35                  40                  45

Ser Leu Ile Tyr Ser Gly Asp Ser Thr Tyr Tyr Ala Asp Ser Val Lys
    50                  55                  60

Gly Arg Phe Ala Ile Ser Arg Asp Ile Ser Lys Asn Thr Val Tyr Leu
65                  70                  75                  80

Gln Met Asn Ser Leu Arg Val Glu Asp Thr Ala Val Tyr Tyr Cys Val
                85                  90                  95

Arg Asp Gly Tyr Tyr Val Ser Asp Met Val Val Trp Gly Lys Gly Thr
            100                 105                 110

Thr Val Thr Val Ser Ser
        115
```

<210> SEQ ID NO 33

<400> SEQUENCE: 33

000

<210> SEQ ID NO 34

<400> SEQUENCE: 34

000

<210> SEQ ID NO 35

<400> SEQUENCE: 35

000

<210> SEQ ID NO 36

<400> SEQUENCE: 36

000

<210> SEQ ID NO 37

<400> SEQUENCE: 37

000

<210> SEQ ID NO 38

<400> SEQUENCE: 38

000

<210> SEQ ID NO 39

<400> SEQUENCE: 39

000

<210> SEQ ID NO 40

<400> SEQUENCE: 40

000

<210> SEQ ID NO 41
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Arg Ser Ser Gln Ser Ile Val His Ser Val Gly Asn Thr Phe Leu Glu
1               5                   10                  15

<210> SEQ ID NO 42
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Lys Val Ser Asn Arg Phe Ser
1               5

<210> SEQ ID NO 43
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Phe Gln Gly Ser Gln Phe Pro Tyr Thr
1               5

<210> SEQ ID NO 44
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Gly Tyr Glu Phe Ser Arg Ser Trp Met Asn
1               5                   10

<210> SEQ ID NO 45
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Arg Ile Tyr Pro Gly Asp Gly Asp Thr Asn Tyr Ser Gly Lys Phe Lys
1               5                   10                  15

Gly

<210> SEQ ID NO 46
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Asp Gly Ser Ser Trp Asp Trp Tyr Phe Asp Val
1               5                   10

<210> SEQ ID NO 47
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Val His Ser
            20                  25                  30

Val Gly Asn Thr Phe Leu Glu Trp Tyr Gln Gln Lys Pro Gly Lys Ala
        35                  40                  45

Pro Lys Leu Leu Ile Tyr Lys Val Ser Asn Arg Phe Ser Gly Val Pro
    50                  55                  60

-continued

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Phe Gln Gly
                85                  90                  95

Ser Gln Phe Pro Tyr Thr Phe Gly Gln Gly Thr Lys Val Glu Ile Lys
            100                 105                 110

Arg

<210> SEQ ID NO 48
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Glu Phe Ser Arg Ser
            20                  25                  30

Trp Met Asn Trp Val Arg Gln Ala Pro Gly Lys Gly Leu Glu Trp Val
        35                  40                  45

Gly Arg Ile Tyr Pro Gly Asp Gly Asp Thr Asn Tyr Ser Gly Lys Phe
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Gly Ser Ser Trp Asp Trp Tyr Phe Asp Val Trp Gly Gln
            100                 105                 110

Gly Thr Leu Val Thr Val Ser Ser
        115                 120

<210> SEQ ID NO 49
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 49

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Val His Ser
            20                  25                  30

Val Gly Asn Thr Phe Leu Glu Trp Tyr Gln Gln Lys Pro Gly Lys Ala
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Phe Gln Gly
                85                  90                  95

Ser Gln Phe Pro Tyr Thr Phe Gly Gln Gly Thr Lys Val Glu Ile Lys
            100                 105                 110

```
Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Cys Val Asp Asn Ala Leu Gln
145                 150                 155                 160

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
        180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
        210                 215

<210> SEQ ID NO 50
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Glu Phe Ser Arg Ser
            20                  25                  30

Trp Met Asn Trp Val Arg Gln Ala Pro Gly Lys Gly Leu Glu Trp Val
        35                  40                  45

Gly Arg Ile Tyr Pro Gly Asp Gly Asp Thr Asn Tyr Ser Gly Lys Phe
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Gly Ser Ser Trp Asp Trp Tyr Phe Asp Val Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
        210                 215                 220

Lys Thr His Thr Cys Pro Pro Cys Pro Ala Pro Glu Leu Leu Gly Gly
225                 230                 235                 240
```

```
Pro Ser Val Phe Leu Phe Pro Pro Lys Pro Lys Asp Thr Leu Met Ile
            245             250             255
Ser Arg Thr Pro Glu Val Thr Cys Val Val Asp Val Ser His Glu
        260             265             270
Asp Pro Glu Val Lys Phe Asn Trp Tyr Val Asp Gly Val Glu Val His
        275             280             285
Asn Ala Lys Thr Lys Pro Arg Glu Glu Gln Tyr Asn Ser Thr Tyr Arg
    290             295             300
Val Val Ser Val Leu Thr Val Leu His Gln Asp Trp Leu Asn Gly Lys
305             310             315             320
Glu Tyr Lys Cys Lys Val Ser Asn Lys Ala Leu Pro Ala Pro Ile Glu
            325             330             335
Lys Thr Ile Ser Lys Ala Lys Gly Gln Pro Arg Glu Pro Gln Val Tyr
            340             345             350
Thr Leu Pro Pro Ser Arg Glu Glu Met Thr Lys Asn Gln Val Ser Leu
            355             360             365
Thr Cys Leu Val Lys Gly Phe Tyr Pro Ser Asp Ile Ala Val Glu Trp
    370             375             380
Glu Ser Asn Gly Gln Pro Glu Asn Asn Tyr Lys Thr Thr Pro Pro Val
385             390             395             400
Leu Asp Ser Asp Gly Ser Phe Phe Leu Tyr Ser Lys Leu Thr Val Asp
                405             410             415
Lys Ser Arg Trp Gln Gln Gly Asn Val Phe Ser Cys Ser Val Met His
            420             425             430
Glu Ala Leu His Asn His Tyr Thr Gln Lys Ser Leu Ser Leu Ser Pro
            435             440             445
Gly Lys
    450
```

QUATERNARY AMINE COMPOUNDS AND ANTIBODY-DRUG CONJUGATES THEREOF

CROSS REFERENCE TO RELATED APPLICATIONS

This application is a divisional application of U.S. application Ser. No. 15/583,492 filed on 1 May 2017 which is a continuation of International Application No. PCT/US2015/063538 having an International Filing Date of 2 Dec. 2015, the entire contents of which are incorporated herein by reference, and which claims the benefit of priority under 35 USC § 119(e) of U.S. Provisional Application Ser. No. 62/087,127 filed on 3 Dec. 2014, which is hereby incorporated by reference in its entirety.

SEQUENCE LISTING

This application contains a Sequence Listing which has been submitted electronically in ASCII format and is hereby incorporated by reference in its entirety. Said ASCII copy, created on May 1, 2017, is named P32456-US-1_SequenceListing.txt and is 35,080 bytes in size.

FIELD OF INVENTION

This invention relates to novel quaternary amine compounds which are useful as linkers of antibody-drug conjugates (ADC). This invention also relates to ADCs containing quaternary amine linkers. This invention also relates to methods of treating diseases in humans.

BACKGROUND OF THE INVENTION

The use of monoclonal antibodies (mABs) to deliver anticancer drugs directly to tumor cells has attracted a great deal of focus in recent years. Two new antibody-drug conjugates have been approved by the FDA for the treatment of cancer. Adcetris® (brentuximab vedotin) is a CD30-directed antibody-drug conjugate (ADC) indicated for the treatment of relapsed or refractory Hodgkin's lymphoma and systemic anaplastic large cell lymphoma (ALCL). Kadcyla® (ado-trastuzumab emtansine) is a new therapy approved for patients with HER2-positive, late-stage (metastatic) breast cancer. To obtain both potent anti-tumor activity and an acceptable therapeutic index in an ADC, several aspects of design may be optimized. Particularly, it is well known that the chemical structure of the linker can have significant impact on both the efficacy and the safety of ADC (Ducry & Stump, Bioconjugate Chem, 2010, 21, 5-13). Choosing the right linker influences proper drug delivery to the intended cellular compartment of cancer cells. Traditionally, options for conjugating drugs (also sometimes called toxins) containing tertiary amines or pyridine functional groups have been limited mainly to attaching these to other functional groups in the molecule. Therefore, it is desirable to develop methods for linking amine or pyridine containing toxins by forming a quaternary salt. Provided herein are different types of quaternary salt containing ADCs that can be cleaved in tumor cells.

SUMMARY OF THE INVENTION

This invention relates to antibody-drug conjugates represented by Formula (I)

Ab-(L-D)$_p$,

Ab is an antibody;
p is 1-8;
L-D is a chemical moiety represented by the following formula -Str-(Pep)-Sp-D;

Str is a stretcher unit covalently attached to Ab;
Pep is a linker;
D is anti-tumor agent represented by the following formula

wherein $R^{20}$ and $R^{30}$ are each independently $C_1$-$C_6$ alkyl, and
$R^{10}$ is a non-hydrogen substituent; or
$R^{30}$ is $C_1$-$C_6$alkyl, and $R^{10}$ and $R^{20}$ together with the N form a substituted $C_3$-$C_7$ heterocycloalkyl ring; or
$R^{30}$ is absent, and $R^{10}$ and $R^{20}$ together with the N form a substituted heteroaryl ring; Sp-D is a spacer moiety of formula:

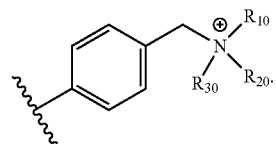

This invention also relates to a method of treating cancer, use of antibody-drug conjugates of Formula (I) in therapy, and use of antibody-drug conjugates of Formula (I) in manufacturing a medicament for treating cancer. This invention also relates to method of preparing antibody-drug conjugates of Formula (I).

BRIEF DESCRIPTION OF THE FIGURES

FIG. 1 shows the efficacy comparison of CD22 ADCs in SCID mice with WSU-DLCL2 human diffuse large B-cell lymphoma tumors. CD22 ADC1-2 and ADC2-2 both demonstrated dose-dependent inhibition of tumor growth compared with vehicle group, and ADC1-2 displayed greater anti-tumor activity than ADC2-2. The non-binding control NaPi2b ADCs had minimal effect on the tumor growth.

DETAILED DESCRIPTION OF THE INVENTION

This invention relates to antibody-conjugates of Formula (I).

In one embodiment, D is an anti-tumor moiety with a potency of $IC_{50}$ 10 nM or less.
In one embodiment, Pep is a peptidyl moiety.
In one embodiment, Pep is a Val-Cit moiety.
In one embodiment, Pep is a Phe-Lys moiety.
In one embodiment, Pep is a Val-Ala moiety.
In one embodiment, Pep is a non-peptide chemical moiety selected from the group consisting of:

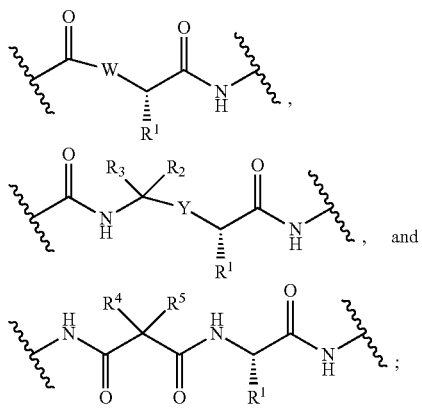

W is —NH-heterocycloalkyl- or heterocycloalkyl;

Y is heteroaryl, aryl, —C(O)$C_1$-$C_6$alkylene, $C_2$-$C_6$alkenyl, $C_1$-$C_6$alkylenyl or —$C_1$-$C_6$alkylene-NH—;

each $R^1$ is independently $C_1$-$C_{10}$alkyl, $C_2$-$C_{10}$alkenyl, ($C_1$-$C_{10}$alkyl)NHC(NH)$NH_2$ or ($C_1$-$C_{10}$alkyl)NHC(O)$NH_2$;

$R^3$ and $R^2$ are each independently H, $C_1$-$C_{10}$alkyl, $C_2$-$C_{10}$alkenyl, arylalkyl or heteroarylalkyl, or $R^3$ and $R^2$ together may form a $C_3$-$C_7$ cycloalkyl;

$R^4$ and $R^5$ are each independently $C_1$-$C_{10}$ alkyl, $C_2$-$C_{10}$ alkenyl, arylalkyl, heteroarylalkyl, ($C_1$-$C_{10}$ alkyl)$OCH_2$—, or $R^4$ and $R^5$ may form a $C_3$-$C_7$ cycloalkyl ring; and p is an integer from 1 to 8.

This invention also relates to antibody-conjugates of Formula (I), which is represented by:

Ab-(L-D)$_p$ wherein Ab is an antibody; L-D is a chemical moiety represented by the following formula

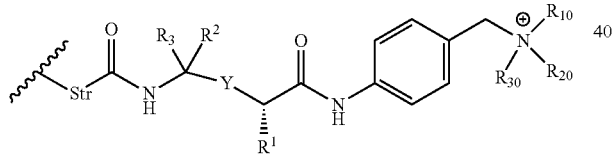

$R^1$ is $C_1$-$C_6$ alkyl, $C_2$-$C_6$ alkenyl, ($C_1$-$C_6$ alkyl)NHC(NH)$NH_2$ or ($C_1$-$C_6$ alkyl)NHC(O)$NH_2$; and $R^3$ and $R^2$ are each independently H, $C_1$-$C_{10}$ alkyl.

This invention also relates to antibody-conjugates of Formula (I), which is represented by:

Ab-(L-D)$_p$ wherein Ab is an antibody; L-D is a chemical moiety of the following formula:

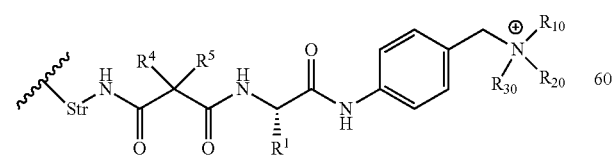

$R^1$ is $C_1$-$C_6$ alkyl, ($C_1$-$C_6$ alkyl)NHC(NH)$NH_2$ or ($C_1$-$C_6$ alkyl)NHC(O)$NH_2$; and $R^4$ and $R^5$ together form a $C_3$-$C_7$ cycloalkyl ring.

This invention also relates to antibody-conjugates of Formula (I), which is represented by:

Ab-(L-D)$_p$ wherein Ab is an antibody;

L-D is a chemical moiety represented by the following formula

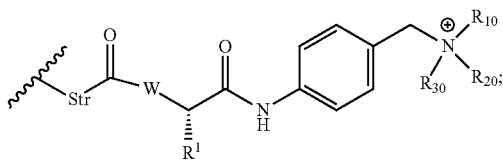

and $R^1$ is $C_1$-$C_6$ alkyl, ($C_1$-$C_6$ alkyl)NHC(NH)$NH_2$ or ($C_1$-$C_6$ alkyl)NHC(O)$NH_2$.

This invention also relates to antibody-conjugates of Formula (I) represented by the following formula:

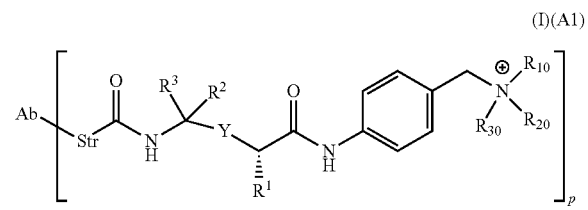

(I)(A1)

wherein:

Str is a chemical moiety represented by the following formula:

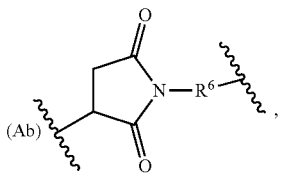

wherein $R^6$ is selected from the group consisting of $C_1$-$C_{10}$ alkylene, and $C_1$-$C_{10}$alkylene-C(O)N($R^a$)—$C_2$-$C_6$ alkylene, where each alkylene may be substituted by one to five substituents selected from the group consisting of halo, trifluoromethyl, difluoromethyl, amino, alkylamino, cyano, sulfonyl, sulfonamide, sulfoxide, hydroxy, alkoxy, ester, carboxylic acid, alkylthio aryl, $C_3$-$C_8$ cycloalkyl, $C_4$-$C_7$ heterocycloalkyl, heteroarylalkyl and heteroaryl;

each $R^a$ is independently H or $C_1$-$C_6$ alkyl; and p is 1, 2, 3 or 4.

This invention also relates to antibody-conjugates of Formula (I) represented by the following formula:

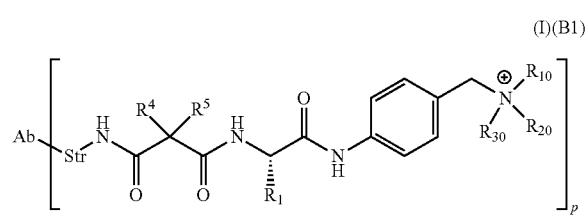

(I)(B1)

wherein:

Str is a chemical moiety represented by the following formula:

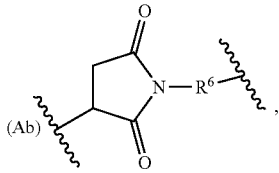

wherein R⁶ is selected from the group consisting of $C_1$-$C_{10}$ alkylene, and $C_1$-$C_{10}$ alkylene-C(O)N(R$^a$)—$C_2$-$C_6$ alkylene, where each alkylene may be substituted by one to five substituents selected from the group consisting of halo, trifluoromethyl, difluoromethyl, amino, alkylamino, cyano, sulfonyl, sulfonamide, sulfoxide, hydroxy, alkoxy, ester, carboxylic acid, alkylthio aryl, $C_3$-$C_8$ cycloalkyl, $C_4$-$C_7$ heterocycloalkyl, heteroarylalkyl and heteroaryl;

each R$^a$ is independently H or $C_1$-$C_6$ alkyl; and p is 1, 2, 3 or 4.

This invention also relates to antibody-conjugates of Formula (I) represented by the following formula:

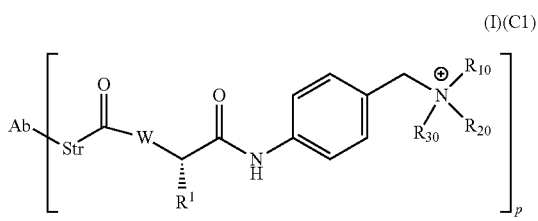
(I)(C1)

wherein:

Str is a chemical moiety represented by the following formula:

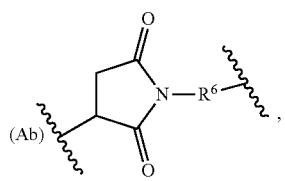

wherein R⁶ is selected from the group consisting of $C_1$-$C_{10}$ alkylene, and $C_1$-$C_{10}$ alkylene-C(O)N(R$^a$)—$C_2$-$C_6$alkylene, where each alkylene may be substituted by one to five substituents selected from the group consisting of halo, trifluoromethyl, difluoromethyl, amino, alkylamino, cyano, sulfonyl, sulfonamide, sulfoxide, hydroxy, alkoxy, ester, carboxylic acid, alkylthio aryl, $C_3$-$C_8$ cycloalkyl, $C_4$-$C_7$ heterocycloalkyl, heteroarylalkyl and heteroaryl;

each R$^a$ is independently H or $C_1$-$C_6$ alkyl; and p is 1, 2, 3 or 4.

This invention also relates to antibody-conjugates of Formula (I)(A1) represented by the following formula:

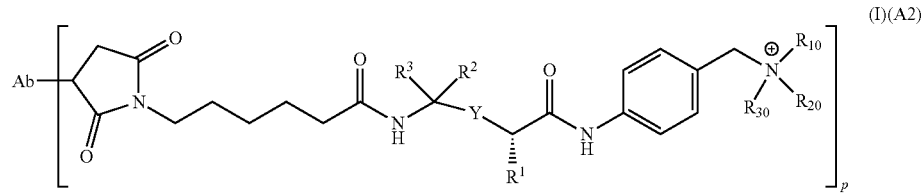
(I)(A2)

wherein:

R¹ is $C_1$-$C_6$ alkyl-NH$_2$, ($C_1$-$C_6$ alkyl)NHC(NH)NH$_2$ or ($C_1$-$C_6$ alkyl)NHC(O)NH$_2$; and p is 1, 2, 3 or 4.

This invention also relates to antibody-conjugates of Formula (I)(B1) represented by the following formula:

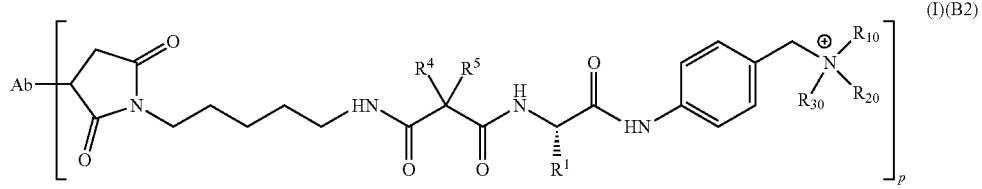
(I)(B2)

wherein:

p is 1, 2, 3 or 4;

$R^1$ is $C_1$-$C_6$alkyl-$NH_2$, ($C_1$-$C_6$alkyl)NHC(NH)$NH_2$ or ($C_1$-$C_6$alkyl)NHC(O)$NH_2$; and $R^4$ and $R^5$ are each independently $C_1$-$C_6$ alkyl, wherein said alkyl are unsubstituted, or $R^4$ and $R^5$ may form a $C_3$-$C_7$ cycloalkyl ring.

This invention also relates to antibody-conjugates of Formula (I)(C1) represented by the following formula:

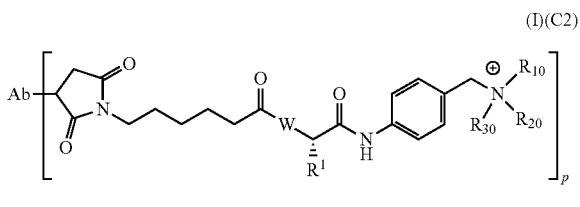

(I)(C2)

wherein:

$R^1$ is $C_1$-$C_6$alkyl-$NH_2$, ($C_1$-$C_6$alkyl)NHC(NH)$NH_2$ or ($C_1$-$C_6$alkyl)NHC(O)$NH_2$; and p is 1, 2, 3 or 4.

In one embodiment, Ab-(L-D)$_p$ is a chemical moiety of Formula (II)

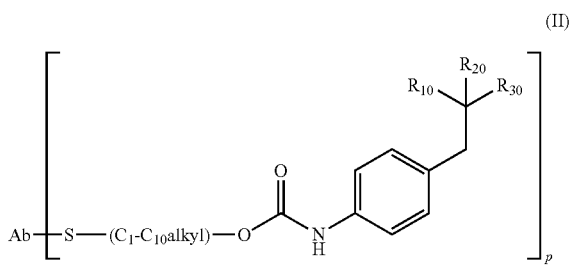

(II)

In one embodiment, Ab-(L-D)$_p$ is Formula (III)

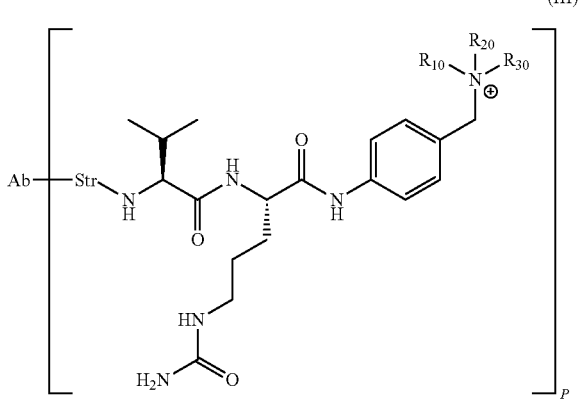

(III)

This invention also relates to antibody-conjugates of formula (I), (I)(A1), (I)(A2), wherein Y is heteroaryl, aryl or alkenyl; and $R^6$ is $C_1$-$C_{10}$alkylene.

This invention also relates to antibody-conjugates of formula (I), (I)(A1), (I)(A2), wherein Y is

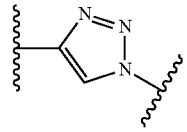

This invention also relates to any one of the above antibody-conjugates, wherein Y is

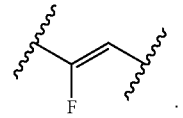

This invention also relates to any one of the above antibody-conjugates, wherein Y is

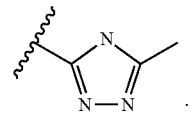 [SMILES: *c1nnc(C)[nH]1]

This invention also relates to any one of the above antibody-conjugates, wherein Str is a chemical moiety represented by the following formula:

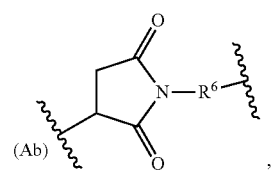

wherein $R^6$ is selected from the group consisting of $C_1$-$C_{10}$alkylene, $C_2$-$C_{10}$alkenyl, $C_3$-$C_8$cycloalkyl, ($C_1$-$C_8$alkylene)O—, and $C_1$-$C_{10}$alkylene-C(O)N($R^a$)—$C_2$-$C_6$alkylene, where each alkylene may be substituted by one to five substituents selected from the group consisting of halo, trifluoromethyl, difluoromethyl, amino, alkylamino, cyano, sulfonyl, sulfonamide, sulfoxide, hydroxy, alkoxy, ester, carboxylic acid, alkylthio aryl, $C_3$-$C_8$cycloalkyl, $C_4$-$C_7$heterocycloalkyl, heteroarylalkyl and heteroaryl; and each $R^a$ is independently H or $C_1$-$C_6$alkyl.

This invention also relates to any one of the above antibody-conjugates, wherein Str has the formula:

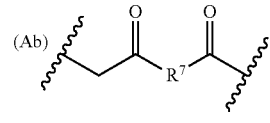

wherein $R^7$ is selected from $C_1$-$C_{10}$alkylene, $C_2$-$C_{10}$alkenyl, ($C_1$-$C_{10}$alkylene)O—, N($R^c$)—($C_2$-$C_6$alkylene)-N($R^c$) and N($R^c$)—($C_2$-$C_6$alkylene); and each $R^c$ is independently H or $C_1$-$C_6$ alkyl.

This invention also relates to any one of the above antibody-conjugates, wherein Str is a chemical moiety represented by the following formula:

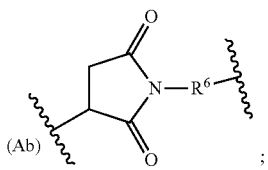

and $R^6$ is $C_1$-$C_6$alkylene.

Linker-Drugs

This invention also relates to a compound of Formula L-D, which is represented by the following formula -Str-(Pep)-Sp-D;

Str is a stretcher unit covalently attached to Ab;
Pep is a linker;
D is anti-tumor antibiotic agent represented by the following formula

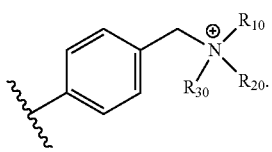

wherein $R^{20}$ and $R^{30}$ are each independently $C_1$-$C_6$alkyl, and $R^{10}$ is a non-hydrogen substituent; or $R^{30}$ is $C_1$-$C_6$alkyl, and $R^{10}$ and $R^{20}$ together with the N form a substituted $C_3$-$C_7$heterocycloalkyl ring; or $R^{30}$ is absent, and $R^{10}$ and $R^{20}$ together with the N form a substituted heteroaryl ring; and Sp-D is a chemical moiety of Formula:

This invention also relates to non-peptide compounds of Formula:

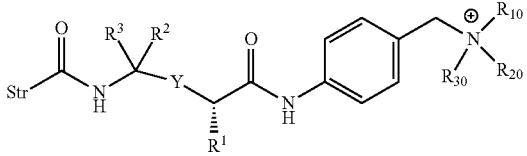

wherein:
Str is a stretcher unit which can be covalently attached to an antibody;
Y is heteroaryl, aryl, —C(O)$C_2$-$C_6$alkenyl, $C_2$-$C_6$alkenyl or —$C_2$-$C_6$alkenyl-NH—;
$R^1$ is $C_1$-$C_{10}$alkyl, ($C_1$-$C_{10}$alkyl)NHC(NH)NH$_2$ or ($C_1$-$C_{10}$alkyl)NHC(O)NH$_2$;

$R^3$ and $R^2$ are each independently H, $C_1$-$C_{10}$alkyl, arylalkyl or heteroarylalkyl, or $R^3$ and $R^2$ together may form a $C_3$-$C_7$cycloalkyl; and D is a drug.

This invention also relates to non-peptide compounds represented by the following formula:

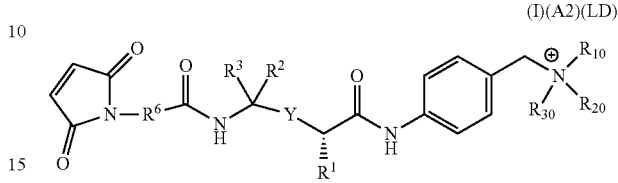

wherein $R_6$ is $C_1$-$C_{10}$alkylene.

This invention also relates to non-peptide compounds represented by the following formula:

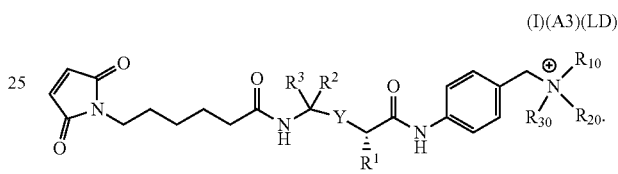

This invention also relates to non-peptide compounds of Formula:

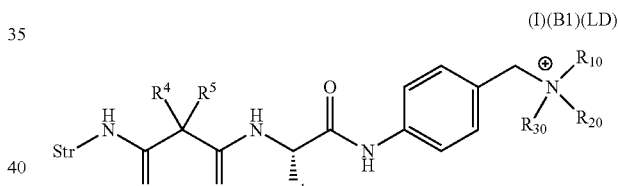

wherein:
Str is a stretcher unit which can be covalently attached to an antibody;
$R^1$ is $C_1$-$C_{10}$alkyl, ($C_1$-$C_{10}$alkyl)NHC(NH)NH$_2$ or ($C_1$-$C_{10}$alkyl)NHC(O)NH$_2$; and
$R^4$ and $R^5$ are each independently $C_1$-$C_{10}$alkyl, arylalkyl, heteroarylalkyl, ($C_1$-$C_{10}$alkyl)OCH$_2$—, or $R^4$ and $R^5$ may form a $C_3$-$C_7$cycloalkyl ring.

This invention also relates to non-peptide compounds represented by the following formula

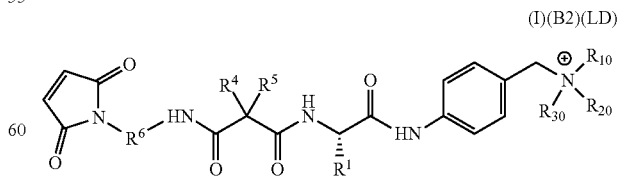

wherein $R_6$ is $C_1$-$C_{10}$alkylene; and $R^4$ and $R^5$ together form a $C_3$-$C_7$cycloalkyl ring.

This invention also relates to non-peptide compounds represented by the following formula

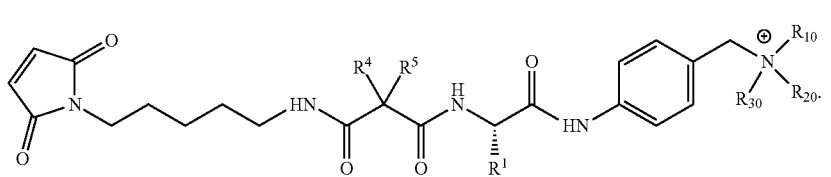
(I)(B3)(LD)

This invention also relates to compounds of Formula (II)(A1)(LD)

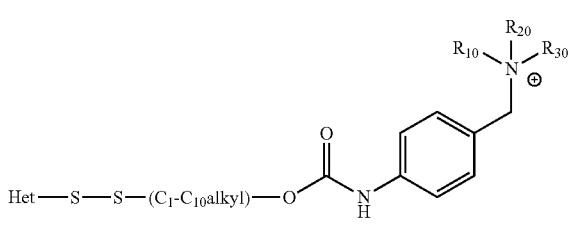

wherein Het is an optionally substituted heteroaryl group.
This invention also relates to compounds of Formula (II)(A2)(LD)

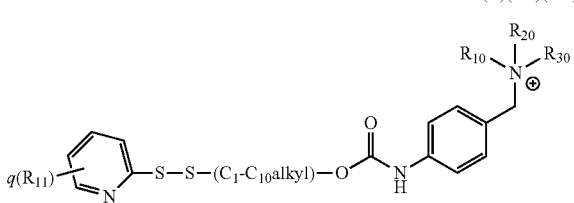

wherein q is 0-5; and $R^{11}$ is $NO_2$ or CN.
This invention also relates to compounds of Formula (II)(A3)(LD)

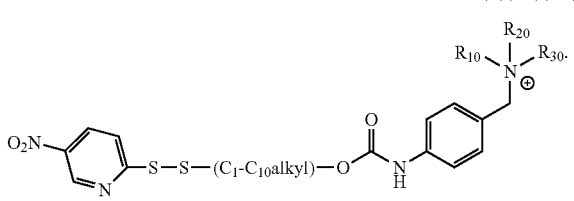

This invention also relates to compounds of Formula (III)(A1)(LD)

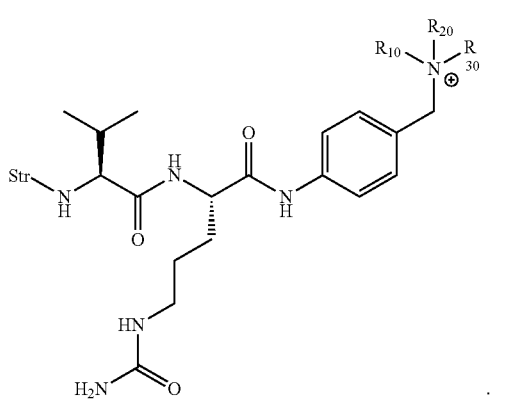

This invention also relates to any of the above compounds of Formula (I)(A1)(LD), (I)(A2)(LD), (I)(A3)(LD), (I)(B1)(LD), (I)(B2)(LD), (I)(B3)(LD), (II)(A1)(LD), or (III)(A1)(LD), wherein Str has the following formula:

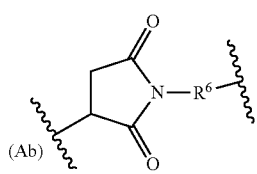

wherein $R^6$ is selected from the group consisting of $C_1$-$C_{10}$alkylene, $C_3$-$C_8$cycloalkyl, O—($C_1$-$C_8$alkylene), and $C_1$-$C_{10}$alkylene-C(O)N($R^a$)—$C_2$-$C_6$alkylene, where each alkylene may be substituted by one to five substituents selected from the group consisting of halo, trifluoromethyl, difluoromethyl, amino, alkylamino, cyano, sulfonyl, sulfonamide, sulfoxide, hydroxy, alkoxy, ester, carboxylic acid, alkylthio aryl, $C_3$-$C_8$cycloalkyl, $C_4$-$C_7$heterocycloalkyl and heteroaryl; each $R^a$ is independently H or $C_1$-$C_6$alkyl;
Sp is —Ar—$R^b$—, wherein Ar is aryl or heteroaryl; and $R^b$ is ($C_1$-$C_{10}$alkylene)O—.
This invention also relates to compounds of formula (I)(A1)(LD), (I)(A2)(LD), (I)(A3)(LD), (I)(B1)(LD), (I)(B2)(LD), (I)(B3)(LD), (II)(A1)(LD), (II)(A2)(LD), (II)(A3)(LD), and (IV)(A1)(LD), wherein $R^6$ is $C_1$-$C_{10}$alkylene;
Sp is —Ar—$R^b$—, wherein Ar is aryl; and $R^b$ is $C_1$-$C_6$alkylene.
This invention also relates to any compounds of Formula (I)(A1)(LD), (I)(A2)(LD), (I)(A3)(LD), (I)(B1)(LD), (I)(B2)(LD), (I)(B3)(LD), (II)(A1)(LD), or (III)(A1)(LD), where $R_6$ is —$(CH_2)_q$ is 1-10.
This invention also relates to compounds of formula (I)(A1)(LD), (I)(A2)(LD), (I)(A3)(LD), (I)(B1)(LD), (I)(B2)(LD), (I)(B3)(LD), (II)(A1)(LD), (II)(A2)(LD), (II)(A3)(LD), and (IV)(A1)(LD), wherein:
Str is a chemical moiety represented by the following formula:

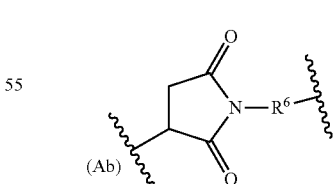

wherein $R^6$ is selected from the group consisting of $C_1$-$C_{10}$alkylene, $C_2$-$C_{10}$alkenyl, $C_3$-$C_8$cycloalkyl, ($C_1$-$C_8$alkylene)O—, and $C_1$-$C_{10}$alkylene-C(O)N($R^a$)—$C_2$-$C_6$alkylene, where each alkylene may be substituted by one to five substituents selected from the group consisting of halo, trifluoromethyl, difluoromethyl, amino, alkylamino, cyano, sulfonyl, sulfonamide, sulfoxide, hydroxy, alkoxy, ester, carboxylic acid, alkylthio aryl, $C_3$-$C_8$cycloalkyl, $C_4$-$C_7$heterocycloalkyl, heteroarylalkyl and heteroaryl; and
each $R^a$ is independently H or $C_1$-$C_6$alkyl.

This invention also relates to compounds of formula (I)(A1)(LD), (I)(A2)(LD), (I)(A3)(LD), (I)(B1)(LD), (I)(B2)(LD), (I)(B3)(LD), (II)(A1)(LD), (II)(A2)(LD), (II)(A3)(LD), and (IV)(A1)(LD), wherein Str has the formula:

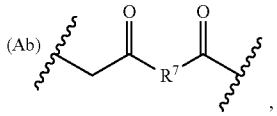

wherein $R^7$ is selected from $C_1$-$C_{10}$alkylene, $C_2$-$C_{10}$alkenyl, ($C_1$-$C_{10}$alkylene)O—, $N(R^c)$—($C_2$-$C_6$alkylene)-$N(R^c)$ and $N(R^c)$—($C_2$-$C_6$alkylene); and
each $R^c$ is independently H or $C_1$-$C_6$ alkyl.

This invention also relates to non-peptide compounds wherein $R^6$ is $C_1$-$C_{10}$ alkylene.

This invention also relates to any one of the above antibody-drug conjugates wherein p is 1.

This invention also relates to any one of the above antibody-drug conjugates wherein p is 2.

This invention also relates to any one of the above antibody-drug conjugates wherein the antibody binds to one or more of polypeptides selected from the group consisting of:
CLL1;
BMPR1B;
E16;
STEAP1;
0772P;
MPF;
NaPi2b;
Sema 5b;
PSCA hlg;
ETBR;
MSG783;
STEAP2;
TrpM4;
CRIPTO;
CD21;
CD79b;
FcRH2;
HER2;
NCA;
MDP;
IL20Rα;
Brevican;
EphB2R;
ASLG659;
PSCA;
GEDA;
BAFF-R;
CD22;
CD79a;
CXCR5;
HLA-DOB;
P2X5;
CD72;
LY64;
FcRH1;
IRTA2;
TENB2;
PMEL17;
TMEFF1;
GDNF-Ra1;
Ly6E;
TMEM46;
Ly6G6D;
LGR5;
RET;
LY6K;
GPR19;
GPR54;
ASPHD1;
Tyrosinase;
TMEM118;
GPR172A;
MUC16 and
CD33.

This invention also relates to methods of treating a disease in a human in need thereof, comprising administering to said human an effective amount of an antibody-drug conjugate of any of the above-described embodiments.

This invention also relates to pharmaceutical compositions comprising an antibody-drug conjugate of any of the above-described embodiments and a pharmaceutically acceptable carrier thereof.

This invention also relates to any of the above-described antibody-drug conjugates, wherein the antibody binds to one or more of polypeptides selected from the group consisting of:
CLL1;
STEAP1;
NaPi2b;
STEAP2;
TrpM4;
CRIPTO;
CD21;
CD79b;
FcRH2;
HER2;
CD22;
CD79a;
CD72;
LY64;
Ly6E;
MUC16; and
CD33.

This invention also relates to any of the above-described antibody-drug conjugates wherein the antibody binds to CD33.

This invention also relates to any of the above-described antibody-drug conjugates wherein the antibody binds to CD33 and the anti-CD33 antibody comprise an HVR-L1 comprising the amino acid sequence of SEQ ID NO:11, an HVR-L2 comprising the amino acid sequence of SEQ ID NO:12, an HVR-L3 comprising the amino acid sequence of SEQ ID NO:13, an HVR-H1 comprising the amino acid sequence of SEQ ID NO: 14, an HVR-H2 comprising the amino acid sequence of SEQ ID NO:15, and an HVR-H3 comprising the amino acid sequence of SEQ ID NO: 16.

This invention also relates to any of the above-described antibody-drug conjugates wherein the antibody binds to CD33 and the anti-CD33 antibody comprises a VL domain comprising the amino acid sequence of SEQ ID NO:17 and a VH domain comprising the amino acid sequence of SEQ ID NO:18.

In some embodiments, the antibody of the antibody-drug conjugate binds CD33. In some embodiments, the antibody of the antibody-drug conjugate comprises (a) HVR-H1 comprising the amino acid sequence of SEQ ID NO:22; (b) HVR-H2 comprising the amino acid sequence of SEQ ID NO:23; (c) HVR-H3 comprising the amino acid sequence of SEQ ID NO:24; (d) HVR-L1 comprising the amino acid sequence of SEQ ID NO:19; (e) HVR-L2 comprising the amino acid sequence of SEQ ID NO:20; and (f) HVR-L3 comprising an amino acid sequence selected from SEQ ID NO:21.

In some embodiments, the antibody comprises a VH as in any of the embodiments provided above, and a VL as in any of the embodiments provided above. In one embodiment, the antibody comprises the VL and VH sequences in SEQ ID NO:25 and SEQ ID NO:26, respectively, including post-translational modifications of those sequences.

This invention also relates to any of the above-described antibody-drug conjugates wherein the antibody binds to NaPi2b.

This invention also relates to any of the above-described antibody-drug conjugates wherein the antibody binds to NaPi2b and the NaPi2b antibody comprise an HVR-L1 comprising the amino acid sequence of SEQ ID NO:1, an HVR-L2 comprising the amino acid sequence of SEQ ID NO:2, an HVR-L3 comprising the amino acid sequence of SEQ ID NO:3, an HVR-H1 comprising the amino acid sequence of SEQ ID NO:4, an HVR-H2 comprising the amino acid sequence of SEQ ID NO:5, and an HVR-H3 comprising the amino acid sequence of SEQ ID NO: 6.

This invention also relates to any of the above-described antibody-drug conjugates wherein the antibody binds to NaPi2b and the NaPi2b antibody comprise s a VL domain comprising the amino acid sequence of SEQ ID NO:7 and a VH domain comprising the amino acid sequence of SEQ ID NO:8.

This invention also relates to any of the above-described antibody-drug conjugates wherein the antibody binds to NaPi2b and the NaPi2b antibody comprises an amino acid sequence of SEQ ID NO:9 and an amino acid sequence of SEQ ID NO: 10.

This invention also relates to any of the above-described antibody-drug conjugates wherein the antibody binds to NaPi2b.

This invention also relates to any of the above-described antibody-drug conjugates wherein the antibody binds to CD-22 and the anti-CD-22 antibody comprise an HVR-L1 comprising the amino acid sequence of SEQ ID NO:41, an HVR-L2 comprising the amino acid sequence of SEQ ID NO: 42, an HVR-L3 comprising the amino acid sequence of SEQ ID NO:43, an HVR-H1 comprising the amino acid sequence of SEQ ID NO:44, an HVR-H2 comprising the amino acid sequence of SEQ ID NO:45, and an HVR-H3 comprising the amino acid sequence of SEQ ID NO:46.

This invention also relates to any of the above-described antibody-drug conjugates wherein the antibody binds to CD-22 and the CD-22 antibody comprise s a VL domain comprising the amino acid sequence of SEQ ID NO:47 and a VH domain comprising the amino acid sequence of SEQ ID NO:48.

This invention also relates to any of the above-described antibody-drug conjugates wherein the antibody binds to CD-22 and the CD-22 antibody comprises an amino acid sequence of SEQ ID NO:49 and an amino acid sequence of SEQ ID NO: 50.

Definitions

Unless stated otherwise, the following terms and phrases as used herein are intended to have the following meanings. When trade names are used herein, applicants intend to independently include the trade name product formulation, the generic drug, and the active pharmaceutical ingredient(s) of the trade name product.

The term "peptidomimetic" or PM as used herein means a non-peptide chemical moiety. Peptides are short chains of amino acid monomers linked by peptide (amide) bonds, the covalent chemical bonds formed when the carboxyl group of one amino acid reacts with the amino group of another. The shortest peptides are dipeptides, consisting of 2 amino acids joined by a single peptide bond, followed by tripeptides, tetrapeptides, etc. A quaternary amine chemical moiety includes non-amino acid chemical moieties. A quaternary amine chemical moiety may also include one or more amino acid that are separated by one or more non-amino acid chemical units. A quaternary amine chemical moiety does not contain in any portion of its chemical structure two or more adjacent amino acids that are linked by peptide bonds.

The term "amino acid" as used herein means glycine, alanine, valine, leucine, isoleucine, phenylalanine, proline, serine, threonine, tyrosine, cysteine, methionine, lysine, arginine, histidine, tryptophan, aspartic acid, glutamic acid, asparagine, glutamine or citrulline.

The term "antibody" herein is used in the broadest sense and specifically covers monoclonal antibodies, polyclonal antibodies, dimers, multimers, multispecific antibodies (e.g., bispecific antibodies), and antibody fragments, so long as they exhibit the desired biological activity (Miller et al (2003) Jour. of Immunology 170:4854-4861). Antibodies may be murine, human, humanized, chimeric, or derived from other species. An antibody is a protein generated by the immune system that is capable of recognizing and binding to a specific antigen. (Janeway, C., Travers, P., Walport, M., Shlomchik (2001) Immuno Biology, 5th Ed., Garland Publishing, New York). A target antigen generally has numerous binding sites, also called epitopes, recognized by CDRs on multiple antibodies. Each antibody that specifically binds to a different epitope has a different structure. Thus, one antigen may have more than one corresponding antibody. An antibody includes a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin disclosed herein can be of any type (e.g., IgG, IgE, IgM, IgD, and IgA), class (e.g., IgG1, IgG2, IgG3, IgG4, IgA1 and IgA2) or subclass of immunoglobulin molecule. The immunoglobulins can be derived from any species. In one aspect, however, the immunoglobulin is of human, murine, or rabbit origin.

The term "antibody fragment(s)" as used herein comprises a portion of a full length antibody, generally the antigen binding or variable region thereof. Examples of antibody fragments include Fab, Fab', F(ab')$_2$, and Fv fragments; diabodies; linear antibodies; minibodies (Olafsen et al (2004) Protein Eng. Design & Sel. 17(4):315-323), fragments produced by a Fab expression library, anti-idiotypic (anti-Id) antibodies, CDR (complementary determining region), and epitope-binding fragments of any of the above which immunospecifically bind to cancer cell antigens, viral antigens or microbial antigens, single-chain antibody molecules; and multispecific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al (1975) Nature, 256:495, or may be made by recombinant DNA methods (see for example: U.S. Pat. Nos. 4,816,567; 5,807,715). The monoclonal antibodies may also be isolated from phage antibody libraries using the techniques described in Clackson et al (1991) Nature, 352:624-628; Marks et al (1991) J. Mol. Biol., 222:581-597; for example.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al (1984) Proc. Natl. Acad. Sci. USA, 81:6851-6855). Chimeric antibodies of interest herein include "primatized" antibodies comprising variable domain antigen-binding sequences derived from a non-human primate (e.g., Old World Monkey, Ape, etc.) and human constant region sequences.

The term "intact antibody" as used herein is one comprising a VL and VH domains, as well as a light chain constant domain (CL) and heavy chain constant domains, CH1, CH2 and CH3. The constant domains may be native sequence constant domains (e.g., human native sequence constant domains) or amino acid sequence variant thereof. The intact antibody may have one or more "effector functions" which refer to those biological activities attributable to the Fc constant region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; and down regulation of cell surface receptors such as B cell receptor and BCR.

The term "Fc region" as used herein means a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest,* 5th Ed. Public Health Service, National Institutes of Health, Bethesda, Md., 1991.

The term "framework" or "FR" as used herein refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4. Depending on the amino acid sequence of the constant domain of their heavy chains, intact antibodies can be assigned to different "classes." There are five major classes of intact immunoglobulin antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called $\alpha$, $\delta$, $\epsilon$, $\gamma$, and $\mu$, respectively. The subunit structures and three-dimensional configurations of different classes of immunoglobulins are well known. Ig forms include hinge-modifications or hingeless forms (Roux et al (1998) J. Immunol. 161:4083-4090; Lund et al (2000) Eur. J. Biochem. 267:7246-7256; US 2005/0048572; US 2004/0229310).

The term "human antibody" as used herein refers to an antibody which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

The term "human consensus framework" as used herein refers to a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest,* Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

The term "humanized antibody" as used herein refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, *J. Mol. Biol.* 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., *Sequences of Proteins of Immunological Interest,* 5th Ed. Public Health Service, National Institutes of Health, Bethesda, Md. (1991).) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., supra.

The term "variable region" or "variable domain" as used herein refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology,* 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector" as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The term "free cysteine amino acid" as used herein refers to a cysteine amino acid residue which has been engineered into a parent antibody, has a thiol functional group (—SH), and is not paired as an intramolecular or intermolecular disulfide bridge.

The term "Linker", "Linker Unit", or "link" as used herein means a chemical moiety comprising a chain of atoms that covalently attaches a drug moiety to an antibody. In various embodiments, a linker is a divalent radical, specified as L.

The term "drug moiety" as used herein means a substance that that inhibits or prevents a cellular function and/or causes cell death or destruction. Cytotoxic agents include, but are not limited to, radioactive isotopes (e.g., At$^{211}$, I$^{131}$, I$^{125}$, Y$^{90}$, Re$^{186}$, Re$^{188}$, Sm$^{153}$, Bi$^{212}$, P$^{32}$, Pb$^{212}$ and radioactive isotopes of Lu); chemotherapeutic agents or drugs (e.g., methotrexate, adriamycin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; and the various antitumor or anticancer agents disclosed below.

As used herein, unless defined otherwise in a claim, the term "acyl" refers to the group —C(O)R', where R' is alkyl, $C_3$-$C_6$cycloalkyl, or heterocyclyl, as each is defined herein.

As used herein, unless defined otherwise in a claim, the term "alkoxy" refers to the group —OR', where R' is $C_1$-$C_4$alkyl or $C_3$-$C_6$cycloalkyl as defined above. Examples of "alkoxy" include methoxy, ethoxy, isopropoxy, propoxy, butoxy, t-butoxy, isobutoxy, cyclopropoxy, and cyclobutoxy, and halogenated forms thereof, e.g. fluoromethoxy and difluoromethoxy.

As used herein, unless defined otherwise in a claim, the term "alkyl" refers to a straight or branched, monovalent or divalent hydrocarbon chain radical having from one to twelve ($C_1$-$C_{12}$) carbon atoms, which may be unsubstituted or substituted with multiple degrees of substitution, for example one, two, three, four, five or six included within the present invention. Examples of substituents are selected from the group consisting of halo, trifluoromethyl, difluoromethyl, amino, alkylamino, cyano, sulfonyl, sulfonamide, sulfoxide, hydroxy, alkoxy, ester, carboxylic acid and alkylthio. Examples of "alkyl" as used herein include, but are not limited to, methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), as well as the divalent ("alkylene") and substituted versions thereof. Examples of substituted alkyl include but are not limited to, hydroxymethyl, difluoromethyl and trifluoromethyl.

As used herein unless otherwise defined in a claim, the term "alkenyl" means a linear or branched, monovalent or divalent hydrocarbon chain radical of any length from two to eight carbon atoms ($C_2$-$C_{10}$) with at least one site of unsaturation, i.e., a carbon-carbon, sp$^2$ double bond, wherein the alkenyl radical may be optionally substituted independently with one or more substituents described above in the definition of "alkyl", and includes radicals having "cis" and "trans" orientations, or alternatively, "E" and "Z" orientations. Examples of alkenyl include, but are not limited to, ethenyl or vinyl (—CH═CH$_2$), prop-1-enyl (—CH═CHCH$_3$), prop-2-enyl (—CH$_2$CH═CH$_2$), 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl, hexa-1,3-dienyl as well as the divalent ("alkenylene") and substituted versions thereof.

As used herein unless otherwise defined in a claim, the term "alkynyl" refers to a linear or branched, monovalent or divalent hydrocarbon radical of any length from two to eight carbon atoms ($C_2$-$C_{10}$) with at least one site of unsaturation, i.e., a carbon-carbon, sp triple bond, wherein the alkynyl radical may be optionally substituted independently with one or more substituents described above in the definition of alkyl, examples of alkynyl includes, but not limited to, ethynyl (—C≡CH), prop-1-ynyl (—C≡CCH$_3$), prop-2-ynyl (propargyl, —CH$_2$C≡CH), but-1-ynyl, but-2-ynyl and but-3-ynyl, as well as the divalent ("alkynylene") and substituted versions thereof.

As used herein, unless defined otherwise in a claim, the term "alkylamino" refers to the group —NR'R", wherein R' is H, $C_1$-$C_6$alkyl or $C_3$-$C_6$cycloalkyl, and R" is $C_1$-$C_6$alkyl or $C_3$-$C_6$cycloalkyl, examples of alkylamino include, but are not limited to, methylamino, dimethylamino, ethylamino, diethylamino, propylamino and cyclopropylamino.

As used herein, unless defined otherwise in a claim, the term "amide" refers to the group —C(O)NR'R", wherein R' and R" are each independently H, $C_1$-$C_6$alkyl, or $C_3$-$C_6$cycloalkyl; examples of amide include, but are not limited to, —C(O)NH$_2$, —C(O)NHCH$_3$, and —C(O)N(CH$_3$)$_2$.

As used herein, unless defined otherwise in a claim, the term "aryl" refers to an aromatic, hydrocarbon, ring system. The ring system may be monocyclic or fused polycyclic (e.g., bicyclic, tricyclic, etc.), substituted or unsubstituted. In various embodiments, the monocyclic aryl ring is $C_5$-$C_{10}$, or $C_5$-$C_7$, or $C_5$-$C_6$, where these carbon numbers refer to the number of carbon atoms that form the ring system. A $C_6$ ring system, i.e. a phenyl ring, is an aryl group. In various embodiments, the polycyclic ring is a bicyclic aryl group, where examples of bicyclic aryl groups include are $C_8$-$C_{12}$, or $C_9$-$C_{10}$. A naphthyl ring, which has 10 carbon atoms, is a polycyclic aryl group. Examples of substituents for aryl are described below in the definition of "optionally substituted".

As used herein, unless defined otherwise in a claim, the term "cyano" refers to the group —CN. As used herein, unless defined otherwise in a claim, "cycloalkyl" refers to a non-aromatic, substituted or unsubstituted, saturated or partially unsaturated hydrocarbon ring group. Examples of substituents are described in the definition of "optionally substituted". In one example, the cycloalkyl group is 3 to 12 carbon atoms ($C_3$-$C_{12}$). In other examples, cycloalkyl is $C_3$-$C_8$, $C_3$-$C_{10}$ or $C_5$-$C_{10}$. In other examples, the cycloalkyl group, as a monocycle, is $C_3$-$C_8$, $C_3$-$C_6$ or $C_5$-$C_6$. In another example, the cycloalkyl group, as a bicycle, is $C_7$-$C_{12}$. In another example, the cycloalkyl group, as a spiro system, is $C_5$-$C_{12}$. Examples of monocyclic cycloalkyl include cyclopropyl, cyclobutyl, cyclopentyl, 1-cyclopent-1-enyl, 1-cyclopent-2-enyl, 1-cyclopent-3-enyl, cyclohexyl, perdeuteriocyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl and cyclododecyl. Exemplary arrangements of bicyclic cycloalkyls having 7 to 12 ring atoms include, but are not limited to, [4,4], [4,5], [5,5], [5,6] or [6,6] ring systems. Exemplary bridged bicyclic cycloalkyls include, but are not limited to, bicyclo[2.2.1]heptane, bicyclo[2.2.2]octane and bicyclo[3.2.2]nonane. Examples of spiro cycloalkyl include, spiro[2.2]pentane, spiro[2.3]hexane, spiro[2.4]heptane, spiro[2.5]octane and spiro[4.5]decane.

As used herein, unless defined otherwise in a claim, the term "ester" refers to the group —C(O)OR', where R' is $C_1$-$C_6$alkyl, or $C_3$-$C_6$cycloalkyl.

As used herein, unless defined otherwise in a claim, the term "heterocycle" "heterocycloalkyl" or "heterocyclyl" refers to unsubstituted and substituted mono- or polycyclic non-aromatic ring system containing 2 to 12 ring carbon atoms and 1 to 3 ring hetero atoms. Polycyclic ring systems can be fused bi- or tri-cyclic, spiro or bridged. Examples of heteroatoms include N, O, and S, including N-oxides, sulfur oxides, and dioxides. In one embodiment, the ring is three to eight-membered and is either fully saturated or has one or more degrees of unsaturation. Multiple degrees of substitution are included within the present definition. Examples of substituents are defined hereunder. Examples of "heterocyclic" groups include, but are not limited to tetrahydrofuranyl, pyranyl, 1,4-dioxanyl, 1,3-dioxanyl, oxolanyl, oxetanyl, 2-oxa-6-azaspiro[3.3]heptan-6-yl, piperidinyl, pyrrolidinyl, morpholinyl, azetidinyl, piperazinyl, pyrrolidinonyl, piperazinonyl, pyrazolidinyl, imidazolinyl, imidazolidinyl, and their various tautomers.

As used herein, unless defined otherwise in a claim, the term "heteroaryl", unless defined otherwise in a claim, refers to an aromatic ring system containing 1 to 9 carbon(s) and at least one heteroatom. Examples of heteroatoms include N, O, and S. Heteroaryl may be monocyclic or polycyclic, substituted or unsubstituted. A monocyclic heteroaryl group may have 2 to 6 ring carbon atoms and 1 to 3 ring hetero atoms in the ring, while a polycyclic heteroaryl may contain 3 to 9 ring carbon atoms and 1 to 5 ring hetero atoms. A polycyclic heteroaryl ring may contain fused, spiro or bridged ring junctions, for example, bicyclic heteroaryl is a polycyclic heteroaryl. Bicyclic heteroaryl rings may contain from 8 to 12 member atoms. Monocyclic heteroaryl rings may contain from 5 to 8 member atoms (carbons and heteroatoms). Exemplary heteroaryl groups include but are not limited to: benzofuranyl, benzothiophenyl, furanyl, imidazolyl, indolyl, azaindolyl, azabenzimidazolyl, benzoxazolyl, benzthiazolyl, benzothiadiazolyl, benzotriazolyl, benzoimidazolyl, tetrazinyl, tetrazolyl, isothiazolyl, oxazolyl, isoxazolyl, pyrazinyl, pyrazolyl, pyridazinyl, pyridinyl, pyrimidinyl, pyrrolyl, quinolinyl, quinazolinyl, quinoxalinyl, triazinyl, triazolyl, thiazolyl and thiophenyl. Examples of substituents for heteroaryl are described below in the definition of "optionally substituted".

As used herein, unless defined otherwise in a claim, the term "heteroarylalkyl" means the group (heteroaryl)$C_1$-$C_3$alkyl.

As used herein, unless defined otherwise in a claim, the term "arylalkyl" means the group (aryl)$C_1$-$C_3$alkyl.

As used herein, unless defined otherwise in a claim, the term "urea" refers to the group —NR'C(O)NR", wherein R' and R" are each independently H, $C_1$-$C_6$alkyl, or $C_3$-$C_6$cycloalkyl.

As used herein, unless defined otherwise in a claim, the term "optionally" means that the subsequently described event(s) may or may not occur, and includes both event(s) that occur and event(s) that do not occur.

As used herein, unless defined otherwise, the phrase "optionally substituted", "substituted" or variations thereof denote an optional substitution, including multiple degrees of substitution, with one or more substituent group, for example, one, two or three. The phrase should not be interpreted as duplicative of the substitutions herein described and depicted. Exemplary optional substituent groups include acyl, $C_1$-$C_6$alkyl, sulfonyl, amino, sulfonamide, sulfoxide, alkoxy, cyano, halo, urea, ester, carboxylic acid, amide, hydroxy, oxo, and nitro.

As used herein, unless defined otherwise in a claim, the term "treatment" refers to alleviating the specified condition, eliminating or reducing one or more symptoms of the condition, slowing or eliminating the progression of the condition.

As used herein, unless defined otherwise in a claim, the term "effective amount" means that amount of a drug or pharmaceutical agent that will elicit the biological or medical response of a tissue, system, animal, or human that is being sought, for instance, by a researcher or clinician. As used herein, unless defined otherwise in a claim, the term "therapeutically effective amount" means any amount which, as compared to a corresponding subject who has not received such amount, results in treatment of a disease, disorder, or side effect, or a decrease in the rate of advancement of a disease or disorder. The term also includes within its scope amounts effective to enhance normal physiological function. For use in therapy, therapeutically effective amounts of a compound of Formula I, as well as salts thereof, may be administered as the raw chemical. Additionally, the active ingredient may be presented as a pharmaceutical composition.

This invention also relates to any one of the examples in the Experimental section.

The phrase "pharmaceutically acceptable salt," as used herein, refers to pharmaceutically acceptable organic or inorganic salts of an antibody-drug conjugate (ADC) or a linker-drug moiety. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

Other salts, which are not pharmaceutically acceptable, may be useful in the preparation of compounds of this invention and these should be considered to form a further aspect of the invention. These salts, such as oxalic or trifluoroacetate, while not in themselves pharmaceutically acceptable, may be useful in the preparation of salts useful as intermediates in obtaining the compounds of the invention and their pharmaceutically acceptable salts.

Compounds of the present invention may exist in solid or liquid form. In the solid state, it may exist in crystalline or noncrystalline form, or as a mixture thereof. The skilled artisan will appreciate that pharmaceutically acceptable solvates may be formed for crystalline or noncrystalline compounds. In crystalline solvates, solvent molecules are incorporated into the crystalline lattice during crystallization. Solvates may involve non-aqueous solvents such as, but not limited to, ethanol, isopropanol, DMSO, acetic acid, ethanolamine, or ethyl acetate, or they may involve water as the solvent that is incorporated into the crystalline lattice. Solvates wherein water is the solvent incorporated into the crystalline lattice are typically referred to as "hydrates." Hydrates include stoichiometric hydrates as well as compositions containing variable amounts of water. The invention includes all such solvates.

The skilled artisan will further appreciate that certain compounds of the invention that exist in crystalline form, including the various solvates thereof, may exhibit polymorphism (i.e. the capacity to occur in different crystalline structures). These different crystalline forms are typically known as "polymorphs." The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

Compounds of the present invention or a salt thereof may exist in stereoisomeric forms (e.g., it contains one or more asymmetric carbon atoms). The individual stereoisomers (enantiomers and diastereomers) and mixtures of these are included within the scope of the present invention. Likewise, it is understood that a compound or salt of Formula (I) may exist in tautomeric forms other than that shown in the formula and these are also included within the scope of the present invention. It is to be understood that the present invention includes all combinations and subsets of the particular groups defined hereinabove. The scope of the present invention includes mixtures of stereoisomers as well as purified enantiomers or enantiomerically/diastereomerically enriched mixtures. It is to be understood that the present invention includes all combinations and subsets of the particular groups defined hereinabove.

The subject invention also includes isotopically-labelled forms of the compounds of the present invention, but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulphur, fluorine, iodine, and chlorine, such as $^2$H, $^3$H, $^{11}$C, $^{13}$C, $^{14}$C, $^{15}$N, $^{17}$O, $^{18}$O, $^{31}$P, $^{32}$P, $^{35}$S, $^{18}$F, $^{36}$Cl, $^{123}$I and $^{125}$I.

Compounds of the present invention and pharmaceutically acceptable salts of said compounds that contain the aforementioned isotopes and/or other isotopes of other atoms are within the scope of the present invention. Isotopically-labelled compounds of the present invention, for example those into which radioactive isotopes such as $^3$H, $^{14}$C are incorporated, are useful in drug and/or substrate tissue distribution assays. Tritiated, i.e., $^3$H, and carbon-14, i.e., u isotopes are commonly used for their ease of preparation and detectability. $^{11}$C and $^{18}$F isotopes are useful in PET (positron emission tomography), and $^{125}$I isotopes are useful in SPECT (single photon emission computerized tomography), all useful in brain imaging. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of formula I and following of this invention can generally be prepared by carrying out the procedures disclosed in the Schemes and/or in the Examples below, by substituting a readily available isotopically labelled reagent for a non-isotopically labelled reagent.

Pharmaceutical Composition of ADCs

Pharmaceutical formulations of therapeutic antibody-drug conjugates (ADC) of the invention are typically prepared for parenteral administration, i.e. bolus, intravenous, intratumor injection with a pharmaceutically acceptable parenteral vehicle and in a unit dosage injectable form. An antibody-drug conjugate (ADC) having the desired degree of purity is optionally mixed with pharmaceutically acceptable diluents, carriers, excipients or stabilizers (Remington's Pharmaceutical Sciences (1980) 16th edition, Osol, A. Ed.), in the form of a lyophilized formulation or an aqueous solution.

Cysteine Engineered Antibodies

The compounds of the invention include antibody-drug conjugates comprising cysteine engineered antibodies where one or more amino acids of a wild-type or parent antibody are replaced with a cysteine amino acid. Any form of antibody may be so engineered, i.e. mutated. For example, a parent Fab antibody fragment may be engineered to form a cysteine engineered Fab, referred to herein as "ThioFab." Similarly, a parent monoclonal antibody may be engineered to form a "ThioMab." It should be noted that a single site mutation yields a single engineered cysteine residue in a ThioFab, while a single site mutation yields two engineered cysteine residues in a ThioMab, due to the dimeric nature of the IgG antibody. Mutants with replaced ("engineered") cysteine (Cys) residues are evaluated for the reactivity of the newly introduced, engineered cysteine thiol groups. The thiol reactivity value is a relative, numerical term in the range of 0 to 1.0 and can be measured for any cysteine engineered antibody. Thiol reactivity values of cysteine engineered antibodies of the invention are in the ranges of 0.6 to 1.0; 0.7 to 1.0; or 0.8 to 1.0. To prepare a cysteine engineered antibody by mutagenesis, DNA encoding an amino acid sequence variant of the starting polypeptide is prepared by a variety of methods known in the art. These methods include, but are not limited to, preparation by site-directed (or oligonucleotide-mediated) mutagenesis, PCR mutagenesis, and cassette mutagenesis of an earlier prepared DNA encoding the polypeptide. Variants of recombinant antibodies may be constructed also by restriction fragment manipulation or by overlap extension PCR with synthetic oligonucleotides. Mutagenic primers encode the cysteine codon replacement(s). Standard mutagenesis techniques can be employed to generate DNA encoding such mutant cysteine engineered antibodies. General guidance can be found in Sambrook et al Molecular Cloning, A Laboratory Manual, Cold Spring Harbor Laboratory Press, Cold Spring Harbor, N.Y., 1989; and Ausubel et al Current Protocols in Molecular Biology, Greene Publishing and Wiley-Interscience, New York, N.Y., 1993. Cysteine amino acids may be engineered at reactive sites in an antibody and which do not form intrachain or intermolecular disulfide linkages (Junutula, et al., 2008b Nature Biotech., 26(8):925-932; Dornan et al (2009) Blood 114(13):2721-2729; U.S. Pat. Nos. 7,521,541; 7,723,485; WO2009/052249, Shen et al (2012) Nature Biotech., 30(2):184-191; Junutula et al (2008) Jour of Immun. Methods 332:41-52). The engineered cysteine thiols may react with linker reagents or the linker-drug intermediates of the present invention which have thiol-reactive, electrophilic groups such as maleimide or alpha-halo amides to form ADC with cysteine engineered antibodies (ThioMabs) and the drug (D) moiety. The location of the drug moiety can thus be designed, controlled, and known. The drug loading can be controlled since the engineered cysteine thiol groups typically react with thiol-reactive linker reagents or linker-drug intermediates in high yield. Engineering an antibody to introduce a cysteine amino acid by substitution at a single site on the heavy or light chain gives two new cysteines on the symmetrical antibody. A drug loading near 2 can be achieved and near homogeneity of the conjugation product ADC.

Cysteine engineered antibodies of the invention preferably retain the antigen binding capability of their wild type, parent antibody counterparts. Thus, cysteine engineered antibodies are capable of binding, preferably specifically, to antigens. Such antigens include, for example, tumor-associated antigens (TAA), cell surface receptor proteins and other cell surface molecules, transmembrane proteins, signaling proteins, cell survival regulatory factors, cell proliferation regulatory factors, molecules associated with (for e.g., known or suspected to contribute functionally to) tissue development or differentiation, lymphokines, cytokines, molecules involved in cell cycle regulation, molecules involved in vasculogenesis and molecules associated with (for e.g., known or suspected to contribute functionally to) angiogenesis. The tumor-associated antigen may be a cluster differentiation factor (i.e., a CD protein). An antigen to which a cysteine engineered antibody is capable of binding may be a member of a subset of one of the above-mentioned categories, wherein the other subset(s) of said category comprise other molecules/antigens that have a distinct characteristic (with respect to the antigen of interest).

Cysteine engineered antibodies are prepared for conjugation with linker-drug intermediates by reduction and reoxidation of intrachain disulfide groups.

Tumor-Associated Antigens:

Antibodies, including but not limited to cysteine engineered antibodies, which may be useful in the antibody-drug conjugates of the invention in the treatment of cancer include, but are not limited to, antibodies against cell surface receptors and tumor-associated antigens (TAA). Certain tumor-associated antigens are known in the art, and can be prepared for use in generating antibodies using methods and information which are well known in the art. In attempts to discover effective cellular targets for cancer diagnosis and therapy, researchers have sought to identify transmembrane or otherwise tumor-associated polypeptides that are specifically expressed on the surface of one or more particular type(s) of cancer cell as compared to on one or more normal non-cancerous cell(s). Often, such tumor-associated polypeptides are more abundantly expressed on the surface of the cancer cells as compared to on the surface of the non-cancerous cells. The identification of such tumor-associated cell surface antigen polypeptides has given rise to the ability to more specifically target cancer cells for destruction via antibody-based therapies.

Examples of tumor-associated antigens TAA include, but are not limited to, those listed below. For convenience, information relating to these antigens, all of which are known in the art, is listed below and includes names, alternative names, Genbank accession numbers and primary reference(s), following nucleic acid and protein sequence identification conventions of the National Center for Biotechnology Information (NCBI). Nucleic acid and protein sequences corresponding to TAA listed below are available in public databases such as GenBank. Tumor-associated antigens targeted by antibodies include all amino acid sequence variants and isoforms possessing at least about 70%, 80%, 85%, 90%, or 95% sequence identity relative to the sequences identified in the cited references, and/or which exhibit substantially the same biological properties or characteristics as a TAA having a sequence found in the cited references. For example, a TAA having a variant sequence generally is able to bind specifically to an antibody that binds specifically to the TAA with the corresponding sequence listed. The sequences and disclosure in the reference specifically recited herein are expressly incorporated by reference.

(1) BMPR1B (bone morphogenetic protein receptor-type IB, Genbank accession no. NM_001203)

ten Dijke, P., et al Science 264 (5155):101-104 (1994), Oncogene 14 (11):1377-1382 (1997)); WO2004063362 (Claim 2); WO2003042661 (Claim 12); US2003134790-A1 (Page 38-39); WO2002102235 (Claim 13; Page 296); WO2003055443 (Page 91-92); WO200299122 (Example 2; Page 528-530); WO2003029421 (Claim 6); WO2003024392 (Claim 2; FIG. 112); WO200298358 (Claim 1; Page 183); WO200254940 (Page 100-101); WO200259377 (Page 349-350); WO200230268 (Claim 27; Page 376); WO200148204 (Example; FIG. 4)

NP_001194 bone morphogenetic protein receptor, type IB/pid=NP_001194.1—

Cross-references: MIM:603248; NP_001194.1; AY065994

(2) E16 (LAT1, SLC7A5, Genbank accession no. NM_003486)

Biochem. Biophys. Res. Commun. 255 (2), 283-288 (1999), Nature 395 (6699):288-291 (1998), Gaugitsch, H. W., et al (1992) J. Biol. Chem. 267 (16):11267-11273); WO2004048938 (Example 2); WO2004032842 (Example IV); WO2003042661 (Claim 12); WO2003016475 (Claim 1); WO200278524 (Example 2); WO200299074 (Claim 19; Page 127-129); WO200286443 (Claim 27; Pages 222, 393); WO2003003906 (Claim 10; Page 293); WO200264798 (Claim 33; Page 93-95); WO200014228 (Claim 5; Page 133-136); US2003224454 (FIG. 3); WO2003025138 (Claim 12; Page 150);

NP_003477 solute carrier family 7 (cationic amino acid transporter, y+ system), member 5/pid=NP_003477.3— *Homo sapiens*

Cross-references: MIM:600182; NP_003477.3; NM_015923; NM_003486_1

(3) STEAP1 (six transmembrane epithelial antigen of prostate, Genbank accession no. NM_012449)

Cancer Res. 61 (15), 5857-5860 (2001), Hubert, R. S., et al (1999) Proc. Natl. Acad. Sci. U.S.A. 96 (25):14523-14528); WO2004065577 (Claim 6); WO2004027049 (FIG. 1L); EP1394274 (Example 11); WO2004016225 (Claim 2); WO2003042661 (Claim 12); US2003157089 (Example 5); US2003185830 (Example 5); US2003064397 (FIG. 2); WO200289747 (Example 5; Page 618-619); WO2003022995 (Example 9; FIG. 13A, Example 53; Page 173, Example 2; FIG. 2A);

NP_036581 six transmembrane epithelial antigen of the prostate

Cross-references: MIM:604415; NP_036581.1; NM_0124491

(4) 0772P (CA125, MUC16, Genbank accession no. AF361486)

J. Biol. Chem. 276 (29):27371-27375 (2001)); WO2004045553 (Claim 14); WO200292836 (Claim 6; FIG. 12); WO200283866 (Claim 15; Page 116-121); US2003124140 (Example 16); Cross-references: GI:34501467; AAK74120.3; AF361486_1

(5) MPF (MPF, MSLN, SMR, megakaryocyte potentiating factor, mesothelin, Genbank accession no. NM_005823) Yamaguchi, N., et al Biol. Chem. 269 (2), 805-808 (1994), Proc. Natl. Acad. Sci. U.S.A. 96 (20):11531-11536 (1999), Proc. Natl. Acad. Sci. U.S.A. 93 (1):136-140 (1996), J. Biol. Chem. 270 (37):21984-21990 (1995)); WO2003101283 (Claim 14); (WO2002102235 (Claim 13; Page 287-288); WO2002101075 (Claim 4; Page 308-309); WO200271928 (Page 320-321); WO9410312 (Page 52-57); Cross-references: MIM:601051; NP_005814.2; NM_005823_1

(6) NaPi2b (NAPI-3B, NPTIIb, SLC34A2, solute carrier family 34 (sodium phosphate), member 2, type II sodium-dependent phosphate transporter 3b, Genbank accession no. NM_006424)

J. Biol. Chem. 277 (22):19665-19672 (2002), Genomics 62 (2):281-284 (1999), Feild, J. A., et al (1999) Biochem. Biophys. Res. Commun. 258 (3):578-582); WO2004022778 (Claim 2); EP1394274 (Example 11); WO2002102235 (Claim 13; Page 326); EP875569 (Claim 1; Page 17-19); WO200157188 (Claim 20; Page 329); WO2004032842 (Example IV); WO200175177 (Claim 24; Page 139-140);

Cross-references: MIM:604217; NP_006415.1; NM_006424_1

(7) Sema 5b (FLJ10372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B, Genbank accession no. AB040878)

Nagase T., et al (2000) DNA Res. 7 (2):143-150); WO2004000997 (Claim 1); WO2003003984 (Claim 1); WO200206339 (Claim 1; Page 50); WO200188133 (Claim 1; Page 41-43, 48-58); WO2003054152 (Claim 20); WO2003101400 (Claim 11);

Accession: Q9P283; EMBL; AB040878; BAA95969.1. Genew; HGNC: 10737;

(8) PSCA hlg (2700050C12Rik, C530008O16Rik, RIKEN cDNA 2700050C12, RIKEN cDNA 2700050C12 gene, Genbank accession no. AY358628); Ross et al (2002) Cancer Res. 62:2546-2553; US2003129192 (Claim 2); US2004044180 (Claim 12); US2004044179 (Claim 11); US2003096961 (Claim 11); US2003232056 (Example 5); WO2003105758 (Claim 12); US2003206918 (Example 5); EP1347046 (Claim 1); WO2003025148 (Claim 20);

Cross-references: GI:37182378; AAQ88991.1; AY358628_1

(9) ETBR (Endothelin type B receptor, Genbank accession no. AY275463);

Nakamuta M., et al Biochem. Biophys. Res. Commun. 177, 34-39, 1991; Ogawa Y., et al Biochem. Biophys. Res. Commun. 178, 248-255, 1991; Arai H., et al Jpn. Circ. J. 56, 1303-1307, 1992; Arai H., et al J. Biol. Chem. 268, 3463-3470, 1993; Sakamoto A., Yanagisawa M., et al Biochem. Biophys. Res. Commun. 178, 656-663, 1991; Elshourbagy N. A., et al J. Biol. Chem. 268, 3873-3879, 1993; Haendler B., et al J. Cardiovasc. Pharmacol. 20, s1-S4, 1992; Tsutsumi M., et al Gene 228, 43-49, 1999; Strausberg R. L., et al Proc. Natl. Acad. Sci. U.S.A. 99, 16899-16903, 2002; Bourgeois C., et al J. Clin. Endocrinol. Metab. 82, 3116-3123, 1997; Okamoto Y., et al Biol. Chem. 272, 21589-21596, 1997; Verheij J. B., et al Am. J. Med. Genet. 108, 223-225, 2002; Hofstra R. M. W., et al Eur. J. Hum. Genet. 5, 180-185, 1997; Puffenberger E. G., et al Cell 79, 1257-1266, 1994; Attie T., et al, Hum. Mol. Genet. 4, 2407-2409, 1995; Auricchio A., et al Hum. Mol. Genet. 5:351-354, 1996; Amiel J., et al Hum. Mol. Genet. 5, 355-357, 1996; Hofstra R. M. W., et al Nat. Genet. 12, 445-447, 1996; Svensson P. J., et al Hum. Genet. 103, 145-148, 1998; Fuchs S., et al Mol. Med. 7, 115-124, 2001; Pingault V., et al (2002) Hum. Genet. 111, 198-206; WO2004045516 (Claim 1);

WO2004048938 (Example 2); WO2004040000 (Claim 151); WO2003087768 (Claim 1); WO2003016475 (Claim 1); WO2003016475 (Claim 1); WO200261087 (FIG. 1); WO2003016494 (FIG. 6); WO2003025138 (Claim 12; Page 144); WO200198351 (Claim 1; Page 124-125); EP522868 (Claim 8; FIG. 2); WO200177172 (Claim 1; Page 297-299); US2003109676; U.S. Pat. No. 6,518,404 (FIG. 3); U.S. Pat. No. 5,773,223 (Claim 1a; Col 31-34); WO2004001004;

(10) MSG783 (RNF124, hypothetical protein FLJ20315, Genbank accession no. NM_017763); WO2003104275 (Claim 1); WO2004046342 (Example 2); WO2003042661 (Claim 12); WO2003083074 (Claim 14; Page 61); WO2003018621 (Claim 1); WO2003024392 (Claim 2; FIG. 93); WO200166689 (Example 6);

Cross-references: LocusID:54894; NP_060233.2; NM_017763_1

(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein, Genbank accession no. AF455138) Lab. Invest. 82 (11):1573-1582 (2002)); WO2003087306; US2003064397 (Claim 1; FIG. 1); WO200272596 (Claim 13; Page 54-55); WO200172962 (Claim 1; FIG. 4B); WO2003104270 (Claim 11); WO2003104270 (Claim 16); US2004005598 (Claim 22); WO2003042661 (Claim 12); US2003060612 (Claim 12; FIG. 10); WO200226822 (Claim 23; FIG. 2); WO200216429 (Claim 12; FIG. 10);

Cross-references: GI:22655488; AAN04080.1; AF455138_1

(12) TrpM4 (BR22450, FLJ20041, TRPM4, TRPM4B, transient receptor potential cation channel, subfamily M, member 4, Genbank accession no. NM_017636)

Xu, X. Z., et al Proc. Natl. Acad. Sci. U.S.A. 98 (19): 10692-10697 (2001), Cell 109 (3):397-407 (2002), J. Biol. Chem. 278 (33):30813-30820 (2003)); US2003143557 (Claim 4); WO200040614 (Claim 14; Page 100-103); WO200210382 (Claim 1; FIG. 9A); WO2003042661 (Claim 12); WO200230268 (Claim 27; Page 391); US2003219806 (Claim 4); WO200162794 (Claim 14; FIG. 1A-D);

Cross-references: MIM:606936; NP_060106.2; NM_017636_1

(13) CRIPTO (CR, CR1, CRGF, CRIPTO, TDGF1, teratocarcinoma-derived growth factor, Genbank accession no. NP_003203 or NM_003212)

Ciccodicola, A., et al EMBO J. 8 (7):1987-1991 (1989), Am. J. Hum. Genet. 49 (3):555-565 (1991)); US2003224411 (Claim 1); WO2003083041 (Example 1); WO2003034984 (Claim 12); WO200288170 (Claim 2; Page 52-53); WO2003024392 (Claim 2; FIG. 58); WO200216413 (Claim 1; Page 94-95, 105); WO200222808 (Claim 2; FIG. 1); U.S. Pat. No. 5,854,399 (Example 2; Col 17-18); U.S. Pat. No. 5,792,616 (FIG. 2);

Cross-references: MIM:187395; NP_003203.1; NM_003212_1

(14) CD21 (CR2 (Complement receptor 2) or C3DR (C3d/Epstein Barr virus receptor) or Hs.73792 Genbank accession no. M26004)

Fujisaku et al (1989) J. Biol. Chem. 264 (4):2118-2125); Weis J. J., et al J. Exp. Med. 167, 1047-1066, 1988; Moore M., et al Proc. Natl. Acad. Sci. U.S.A. 84, 9194-9198, 1987; Barel M., et al Mol. Immunol. 35, 1025-1031, 1998; Weis J. J., et al Proc. Natl. Acad. Sci. U.S.A. 83, 5639-5643, 1986; Sinha S. K., et al (1993) J. Immunol. 150, 5311-5320; WO2004045520 (Example 4); US2004005538 (Example 1); WO2003062401 (Claim 9); WO2004045520 (Example 4); WO9102536 (FIGS. 9.1-9.9); WO2004020595 (Claim 1);

Accession: P20023; Q13866; Q14212; EMBL; M26004; AAA35786.1.

(15) CD79b (CD79B, CD79β, IGb (immunoglobulin-associated beta), B29, Genbank accession no. NM_000626 or 11038674)

Proc. Natl. Acad. Sci. U.S.A. (2003) 100 (7):4126-4131, Blood (2002) 100 (9):3068-3076, Muller et al (1992) Eur. J. Immunol. 22 (6):1621-1625); WO2004016225 (Claim 2, FIG. 140); WO2003087768, US2004101874 (Claim 1, page 102); WO2003062401 (Claim 9); WO200278524 (Example 2); US2002150573 (Claim 5, page 15); U.S. Pat. No. 5,644,033; WO2003048202 (Claim 1, pages 306 and 309); WO 99/558658, U.S. Pat. No. 6,534,482 (Claim 13, FIG. 17A/B); WO200055351 (Claim 11, pages 1145-1146);

Cross-references: MIM:147245; NP_000617.1; NM_000626_1

(16) FcRH2 (IFGP4, IRTA4, SPAP1A (SH2 domain containing phosphatase anchor protein 1a), SPAP1B, SPAP1C, Genbank accession no. NM_030764, AY358130)

Genome Res. 13 (10):2265-2270 (2003), Immunogenetics 54 (2):87-95 (2002), Blood 99 (8):2662-2669 (2002), Proc. Natl. Acad. Sci. U.S.A. 98 (17):9772-9777 (2001), Xu, M. J., et al (2001) Biochem. Biophys. Res. Commun. 280 (3):768-775; WO2004016225 (Claim 2); WO2003077836; WO200138490 (Claim 5; FIG. 18D-1-18D-2); WO2003097803 (Claim 12); WO2003089624 (Claim 25);

Cross-references: MIM:606509; NP_110391.2; NM_030764_1

(17) HER2 (ErbB2, Genbank accession no. M11730)

Coussens L., et al Science (1985) 230(4730):1132-1139); Yamamoto T., et al Nature 319, 230-234, 1986; Semba K., et al Proc. Natl. Acad. Sci. U.S.A. 82, 6497-6501, 1985; Swiercz J. M., et al J. Cell Biol. 165, 869-880, 2004; Kuhns J. J., et al J. Biol. Chem. 274, 36422-36427, 1999; Cho H.-S., et al Nature 421, 756-760, 2003; Ehsani A., et al (1993) Genomics 15, 426-429; WO2004048938 (Example 2); WO2004027049 (FIG. 1I); WO2004009622; WO2003081210; WO2003089904 (Claim 9); WO2003016475 (Claim 1); US2003118592; WO2003008537 (Claim 1); WO2003055439 (Claim 29; FIG. 1A-B); WO2003025228 (Claim 37; FIG. 5C); WO200222636 (Example 13; Page 95-107); WO200212341 (Claim 68; FIG. 7); WO200213847 (Page 71-74); WO200214503 (Page 114-117); WO200153463 (Claim 2; Page 41-46); WO200141787 (Page 15); WO200044899 (Claim 52; FIG. 7); WO200020579 (Claim 3; FIG. 2); U.S. Pat. No. 5,869,445 (Claim 3; Col 31-38); WO9630514 (Claim 2; Page 56-61); EP1439393 (Claim 7); WO2004043361 (Claim 7); WO2004022709; WO200100244 (Example 3; FIG. 4); Accession: P04626; EMBL; M11767; AAA35808.1. EMBL; M11761; AAA35808.1.

(18) NCA (CEACAM6, Genbank accession no. M18728);

Barnett T., et al Genomics 3, 59-66, 1988; Tawaragi Y., et al Biochem. Biophys. Res. Commun. 150, 89-96, 1988; Strausberg R. L., et al Proc. Natl. Acad. Sci. U.S.A. 99:16899-16903, 2002; WO2004063709; EP1439393 (Claim 7); WO2004044178 (Example 4); WO2004031238; WO2003042661 (Claim 12); WO200278524 (Example 2); WO200286443 (Claim 27; Page 427); WO200260317 (Claim 2);

Accession: P40199; Q14920; EMBL; M29541; AAA59915.1. EMBL; M18728;

(19) MDP (DPEP1, Genbank accession no. BC017023)
Proc. Natl. Acad. Sci. U.S.A. 99 (26):16899-16903 (2002)); WO2003016475 (Claim 1); WO200264798 (Claim 33; Page 85-87); JP05003790 (FIG. 6-8); WO9946284 (FIG. 9);

Cross-references: MIM:179780; AAH17023.1; BC017023_1

(20) IL20Rα (IL20Ra, ZCYTOR7, Genbank accession no. AF184971);

Clark H. F., et al Genome Res. 13, 2265-2270, 2003; Mungall A. J., et al Nature 425, 805-811, 2003; Blumberg H., et al Cell 104, 9-19, 2001; Dumoutier L., et al J. Immunol. 167, 3545-3549, 2001; Parrish-Novak J., et al J. Biol. Chem. 277, 47517-47523, 2002; Pletnev S., et al (2003) Biochemistry 42:12617-12624; Sheikh F., et al (2004) J. Immunol. 172, 2006-2010; EP1394274 (Example 11); US2004005320 (Example 5); WO2003029262 (Page 74-75); WO2003002717 (Claim 2; Page 63); WO200222153 (Page 45-47); US2002042366 (Page 20-21); WO200146261 (Page 57-59); WO200146232 (Page 63-65); WO9837193 (Claim 1; Page 55-59);

Accession: Q9UHF4; Q6UWA9; Q96SH8; EMBL; AF184971; AAF01320.1.

(21) Brevican (BCAN, BEHAB, Genbank accession no. AF229053)

Gary S. C., et al Gene 256, 139-147, 2000; Clark H. F., et al Genome Res. 13, 2265-2270, 2003; Strausberg R. L., et al Proc. Natl. Acad. Sci. U.S.A. 99, 16899-16903, 2002; US2003186372 (Claim 11); US2003186373 (Claim 11); US2003119131 (Claim 1; FIG. 52); US2003119122 (Claim 1; FIG. 52); US2003119126 (Claim 1); US2003119121 (Claim 1; FIG. 52); US2003119129 (Claim 1); US2003119130 (Claim 1); US2003119128 (Claim 1; FIG. 52); US2003119125 (Claim 1); WO2003016475 (Claim 1); WO200202634 (Claim 1);

(22) EphB2R (DRT, ERK, Hek5, EPHT3, Tyro5, Genbank accession no. NM_004442) Chan, J. and Watt, V. M., Oncogene 6 (6), 1057-1061 (1991) Oncogene 10 (5):897-905 (1995), Annu. Rev. Neurosci. 21:309-345 (1998), Int. Rev. Cytol. 196:177-244 (2000)); WO2003042661 (Claim 12); WO200053216 (Claim 1; Page 41); WO2004065576 (Claim 1); WO2004020583 (Claim 9); WO2003004529 (Page 128-132); WO200053216 (Claim 1; Page 42);

Cross-references: MIM:600997; NP_004433.2; NM_004442_1

(23) ASLG659 (B7h, Genbank accession no. AX092328)
US20040101899 (Claim 2); WO2003104399 (Claim 11); WO2004000221 (FIG. 3); US2003165504 (Claim 1); US2003124140 (Example 2); US2003065143 (FIG. 60); WO2002102235 (Claim 13; Page 299); US2003091580 (Example 2); WO200210187 (Claim 6; FIG. 10); WO200194641 (Claim 12; FIG. 7b); WO200202624 (Claim 13; FIG. 1A-1B); US2002034749 (Claim 54; Page 45-46); WO200206317 (Example 2; Page 320-321, claim 34; Page 321-322); WO200271928 (Page 468-469); WO200202587 (Example 1; FIG. 1); WO200140269 (Example 3; Pages 190-192); WO200036107 (Example 2; Page 205-207); WO2004053079 (Claim 12); WO2003004989 (Claim 1); WO200271928 (Page 233-234, 452-453); WO 0116318;

(24) PSCA (Prostate stem cell antigen precursor, Genbank accession no. AJ297436)

Reiter R. E., et al Proc. Natl. Acad. Sci. U.S.A. 95, 1735-1740, 1998; Gu Z., et al Oncogene 19, 1288-1296, 2000; Biochem. Biophys. Res. Commun. (2000) 275(3): 783-788; WO2004022709; EP1394274 (Example 11); US2004018553 (Claim 17); WO2003008537 (Claim 1); WO200281646 (Claim 1; Page 164); WO2003003906 (Claim 10; Page 288); WO200140309 (Example 1; FIG. 17); US2001055751 (Example 1; FIG. 1b); WO200032752 (Claim 18; FIG. 1); WO9851805 (Claim 17; Page 97); WO9851824 (Claim 10; Page 94); WO9840403 (Claim 2; FIG. 1B);

Accession: 043653; EMBL; AF043498; AAC39607.1.

(25) GEDA (Genbank accession No. AY260763);

AAP14954 lipoma HMGIC fusion-partner-like protein/pid=AAP14954.1—*Homo sapiens* Species: *Homo sapiens* (human)

WO2003054152 (Claim 20); WO2003000842 (Claim 1); WO2003023013 (Example 3, claim 20); US2003194704 (Claim 45);

Cross-references: GI:30102449; AAP14954.1; AY260763_1

(26) BAFF-R (B cell-activating factor receptor, BLyS receptor 3, BR3, Genbank accession No. AF116456); BAFF receptor/pid=NP_443177.1—*Homo sapiens*

Thompson, J. S., et al Science 293 (5537), 2108-2111 (2001); WO2004058309; WO2004011611; WO2003045422 (Example; Page 32-33); WO2003014294 (Claim 35; FIG. 6B); WO2003035846 (Claim 70; Page 615-616); WO200294852 (Col 136-137); WO200238766 (Claim 3; Page 133); WO200224909 (Example 3; FIG. 3);

Cross-references: MIM: 606269; NP_443177.1; NM_052945_1; AF132600

(27) CD22 (B-cell receptor CD22-B isoform, BL-CAM, Lyb-8, Lyb8, SIGLEC-2, FLJ22814, Genbank accession No. AK026467);

Wilson et al (1991) J. Exp. Med. 173:137-146; WO2003072036 (Claim 1; FIG. 1);

Cross-references: MIM:107266; NP_001762.1; NM_001771_1

(28) CD79a (CD79A, CD79a, immunoglobulin-associated alpha, a B cell-specific protein that covalently interacts with Ig beta (CD79B) and forms a complex on the surface with Ig M molecules, transduces a signal involved in B-cell differentiation), pI: 4.84, MW: 25028 TM: 2 [P] Gene Chromosome: 19q13.2, Genbank accession No. NP_001774.10)

WO2003088808, US20030228319; WO2003062401 (Claim 9); US2002150573 (Claim 4, pages 13-14); WO9958658 (Claim 13, FIG. 16); WO9207574 (FIG. 1); U.S. Pat. No. 5,644,033; Ha et al (1992) J. Immunol. 148(5):1526-1531; Mueller et al (1992) Eur. J. Biochem. 22:1621-1625; Hashimoto et al (1994) Immunogenetics 40(4):287-295; Preud'homme et al (1992) Clin. Exp. Immunol. 90(1):141-146; Yu et al (1992) J. Immunol. 148(2) 633-637; Sakaguchi et al (1988) EMBO J. 7(11):3457-3464;

(29) CXCR5 (Burkitt's lymphoma receptor 1, a G protein-coupled receptor that is activated by the CXCL13 chemokine, functions in lymphocyte migration and humoral defense, plays a role in HIV-2 infection and perhaps development of AIDS, lymphoma, myeloma, and leukemia); 372 aa, pI: 8.54 MW: 41959 TM: 7 [P] Gene Chromosome: 11q23.3, Genbank accession No. NP_001707.1)

WO2004040000; WO2004015426; US2003105292 (Example 2); U.S. Pat. No. 6,555,339 (Example 2); WO200261087 (FIG. 1); WO200157188 (Claim 20, page 269); WO200172830 (pages 12-13); WO200022129 (Example 1, pages 152-153, Example 2, pages 254-256); WO9928468 (Claim 1, page 38); U.S. Pat. No. 5,440,021 (Example 2, col 49-52); WO9428931 (pages 56-58); WO9217497 (Claim 7, FIG. 5); Dobner et al (1992) Eur. J. Immunol. 22:2795-2799; Barella et al (1995) Biochem. J. 309:773-779;

(30) HLA-DOB (Beta subunit of MHC class II molecule (Ia antigen) that binds peptides and presents them to CD4+

T lymphocytes); 273 aa, pI: 6.56 MW: 30820 TM: 1 [P] Gene Chromosome: 6p21.3, Genbank accession No. NP_002111.1)

Tonnelle et al (1985) EMBO J. 4(11):2839-2847; Jonsson et al (1989) Immunogenetics 29(6):411-413; Beck et al (1992) J. Mol. Biol. 228:433-441; Strausberg et al (2002) Proc. Natl. Acad. Sci USA 99:16899-16903; Servenius et al (1987) J. Biol. Chem. 262:8759-8766; Beck et al (1996) J. Mol. Biol. 255:1-13; Naruse et al (2002) Tissue Antigens 59:512-519; WO9958658 (Claim 13, FIG. 15); U.S. Pat. No. 6,153,408 (Col 35-38); U.S. Pat. No. 5,976,551 (col 168-170); U.S. Pat. No. 6,011,146 (col 145-146); Kasahara et al (1989) Immunogenetics 30(1):66-68; Larhammar et al (1985) J. Biol. Chem. 260(26):14111-14119;

(31) P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability); 422 aa), pI: 7.63, MW: 47206 TM: 1 [P] Gene Chromosome: 17p13.3, Genbank accession No. NP_002552.2)

Le et al (1997) FEBS Lett. 418(1-2):195-199; WO2004047749; WO2003072035 (Claim 10); Touchman et al (2000) Genome Res. 10:165-173; WO200222660 (Claim 20); WO2003093444 (Claim 1); WO2003087768 (Claim 1); WO2003029277 (page 82);

(32) CD72 (B-cell differentiation antigen CD72, Lyb-2) PROTEIN SEQUENCE Full maeaity . . . tafrfpd (1 . . . 359; 359 aa), pI: 8.66, MW: 40225 TM: 1 [P] Gene Chromosome: 9p13.3, Genbank accession No. NP_001773.1)

WO2004042346 (Claim 65); WO2003026493 (pages 51-52, 57-58); WO200075655 (pages 105-106); Von Hoegen et al (1990) J. Immunol. 144(12):4870-4877; Strausberg et al (2002) Proc. Natl. Acad. Sci USA 99:16899-16903;

(33) LY64 (Lymphocyte antigen 64 (RP105), type I membrane protein of the leucine rich repeat (LRR) family, regulates B-cell activation and apoptosis, loss of function is associated with increased disease activity in patients with systemic lupus erythematosis); 661 aa, pI: 6.20, MW: 74147 TM: 1 [P] Gene Chromosome: 5q12, Genbank accession No. NP_005573.1)

US2002193567; WO9707198 (Claim 11, pages 39-42); Miura et al (1996) Genomics 38(3):299-304; Miura et al (1998) Blood 92:2815-2822; WO2003083047; WO9744452 (Claim 8, pages 57-61); WO200012130 (pages 24-26);

(34) FcRH1 (Fc receptor-like protein 1, a putative receptor for the immunoglobulin Fc domain that contains $C_2$ type Ig-like and ITAM domains, may have a role in B-lymphocyte differentiation); 429 aa, pI: 5.28, MW: 46925 TM: 1 [P] Gene Chromosome: 1q21-1q22, Genbank accession No. NP_443170.1)

WO2003077836; WO200138490 (Claim 6, FIG. 18E-1-18-E-2); Davis et al (2001) Proc. Natl. Acad. Sci USA 98(17):9772-9777; WO2003089624 (Claim 8); EP1347046 (Claim 1); WO2003089624 (Claim 7);

(35) IRTA2 (Immunoglobulin superfamily receptor translocation associated 2, a putative immunoreceptor with possible roles in B cell development and lymphomagenesis; deregulation of the gene by translocation occurs in some B cell malignancies); 977 aa, pI: 6.88 MW: 106468 TM: 1 [P] Gene Chromosome: 1q21, Genbank accession No. Human: AF343662, AF343663, AF343664, AF343665, AF369794, AF397453, AK090423, AK090475, AL834187, AY358085; Mouse: AK089756, AY158090, AY506558; NP_112571.1 WO2003024392 (Claim 2, FIG. 97); Nakayama et al (2000) Biochem. Biophys. Res. Commun. 277(1):124-127; WO2003077836; WO200138490 (Claim 3, FIG. 18B-1-18B-2);

(36) TENB2 (TMEFF2, tomoregulin, TPEF, HPP1, TR, putative transmembrane proteoglycan, related to the EGF/heregulin family of growth factors and follistatin); 374 aa, NCBI Accession: AAD55776, AAF91397, AAG49451, NCBI RefSeq: NP_057276; NCBI Gene: 23671; OMIM: 605734; SwissProt Q9UIK5; Genbank accession No. AF179274; AY358907, CAF85723, CQ782436

WO2004074320; JP2004113151; WO2003042661; WO2003009814; EP1295944 (pages 69-70); WO200230268 (page 329); WO200190304; US2004249130; US2004022727; WO2004063355; US2004197325; US2003232350; US2004005563; US2003124579; Hone et al (2000) Genomics 67:146-152; Uchida et al (1999) Biochem. Biophys. Res. Commun. 266:593-602; Liang et al (2000) Cancer Res. 60:4907-12; Glynne-Jones et al (2001) Int J Cancer. October 15; 94(2): 178-84;

(37) PMEL17 (silver homolog; SILV; D12S53E; PMEL17; (SI); (SIL); ME20; gp100) BC001414; BT007202; M32295; M77348; NM_006928; McGlinchey, R. P. et al (2009) Proc. Natl. Acad. Sci. U.S.A. 106 (33), 13731-13736; Kummer, M. P. et al (2009) J. Biol. Chem. 284 (4), 2296-2306;

(38) TMEFF1 (transmembrane protein with EGF-like and two follistatin-like domains 1; Tomoregulin-1; H7365; C9orf2; C9ORF2; U19878; X83961) NM_080655; NM_003692; Harms, P. W. (2003) Genes Dev. 17 (21), 2624-2629; Gery, S. et al (2003) Oncogene 22 (18):2723-2727;

(39) GDNF-Ra1 (GDNF family receptor alpha 1; GFRA1; GDNFR; GDNFRA; RETL1; TRNR1; RET1L; GDNFR-alpha1; GFR-ALPHA-1; U95847; BC014962; NM_145793) NM_005264; Kim, M. H. et al (2009) Mol. Cell. Biol. 29 (8), 2264-2277; Treanor, J. J. et al (1996) Nature 382 (6586):80-83;

(40) Ly6E (lymphocyte antigen 6 complex, locus E: Ly67,RIG-E,SCA-2,TSA-1) NP_002337.1; NM_002346.2; de Nooij-van Dalen, A. G. et al (2003) Int. J. Cancer 103 (6), 768-774; Zammit, D. J. et al (2002) Mol. Cell. Biol. 22 (3):946-952;

(41) TMEM46 (shisa homolog 2 (*Xenopus laevis*); SHISA2) NP_001007539.1; NM_001007538.1; Furushima, K. et al (2007) Dev. Biol. 306 (2), 480-492; Clark, H. F. et al (2003) Genome Res. 13 (10):2265-2270;

(42) Ly6G6D (lymphocyte antigen 6 complex, locus G6D; Ly6-D, MEGT1) NP_067079.2; NM_021246.2; Mallya, M. et al (2002) Genomics 80 (1):113-123; Ribas, G. et al (1999) J. Immunol. 163 (1):278-287;

(43) LGR5 (leucine-rich repeat-containing G protein-coupled receptor 5; GPR49, GPR67) NP_003658.1; NM_003667.2; Salanti, G. et al (2009) Am. J. Epidemiol. 170 (5):537-545; Yamamoto, Y. et al (2003) Hepatology 37 (3):528-533;

(44) RET (ret proto-oncogene, MEN2A; HSCR1; MEN2B; MTC1; (PTC); CDHF12; Hs.168114; RET51; RET-ELE1) NP_066124.1; NM_020975.4; Tsukamoto, H. et al (2009) Cancer Sci. 100 (10):1895-1901; Narita, N. et al (2009) Oncogene 28 (34):3058-3068;

(45) LY6K (lymphocyte antigen 6 complex, locus K; LY6K; HSJ001348; FLJ35226) NP_059997.3; NM_017527.3; Ishikawa, N. et al (2007) Cancer Res. 67 (24):11601-11611; de Nooij-van Dalen, A. G. et al (2003) Int. J. Cancer 103 (6):768-774;

(46) GPR19 (G protein-coupled receptor 19; Mm.4787) NP_006134.1; NM_006143.2; Montpetit, A. and Sinnett, D. (1999) Hum. Genet. 105 (1-2):162-164; O'Dowd, B. F. et al (1996) FEBS Lett. 234 (3):325-329;

(47) GPR54 (KISS1 receptor; KISS1R; GPR54; HOT7T175; AXOR12) NP_115940.2; NM_032551.4; Navenot, J. M. et al (2009) Mol. Pharmacol. 75 (6):1300-1306; Hata, K. et al (2009) Anticancer Res. 29 (2):617-623;

(48) ASPHD1 (aspartate beta-hydroxylase domain containing 1; LOC253982) NP_859069.2; NM_181718.3; Gerhard, D. S. et al (2004) Genome Res. 14 (10B):2121-2127;

(49) Tyrosinase (TYR; OCAIA; OCA1A; tyrosinase; SHEP3) NP_000363.1; NM_000372.4; Bishop, D. T. et al (2009) Nat. Genet. 41 (8):920-925; Nan, H. et al (2009) Int. J. Cancer 125 (4): 909-917;

(50) TMEM118 (ring finger protein, transmembrane RNFT2; FLJ14627) NP_001103373.1; NM_001109903.1; Clark, H. F. et al (2003) Genome Res. 13 (10):2265-2270; Scherer, S. E. et al (2006) Nature 440 (7082):346-351 (51) GPR172A (G protein-coupled receptor 172A, GPCR41; FLJ11856; D15Ertd747e) NP_078807.1; NM_024531.3; Ericsson, T. A. et al (2003) Proc. Natl. Acad. Sci. U.S.A. 100 (11):6759-6764; Takeda, S. et al (2002) FEBS Lett. 520 (1-3):97-101.

In one embodiment, the antibody binds to one or more of the following polypeptides: BMPR1B; E16; STEAP1; 0772P; MPF; NaPi2b; Sema 5b; PSCA hlg; ETBR; MSG783; STEAP2; TrpM4; CRIPTO; CD21; CD79b; FcRH2; HER2; NCA; MDP; IL20Ra; Brevican; EphB2R; ASLG659; PSCA; GEDA; BAFF-R; CD22; CD79a; CXCR5; HLA-DOB; P2X5; CD72; LY64; FcRH1; IRTA2; TENB2; PMEL17; TMEFF1; GDNF-Ra1; Ly6E; TMEM46; Ly6G6D; LGR5; RET; LY6K; GPR19; GPR54; ASPHD1; Tyrosinase; TMEM118; GPR172A; or CD33.

In one embodiment, the antibody binds to BMPR1B.
In one embodiment, the antibody binds to E16.
In one embodiment, the antibody binds to STEAP1.
In one embodiment, the antibody binds to 0772P.
In one embodiment, the antibody binds to MPF.
In one embodiment, the antibody binds to NaPi2b.
In one embodiment, the antibody binds to Sema 5b.
In one embodiment, the antibody binds to PSCA hlg.
In one embodiment, the antibody binds to ETBR.
In one embodiment, the antibody binds to MSG783.
In one embodiment, the antibody binds to STEAP2.
In one embodiment, the antibody binds to TrpM4.
In one embodiment, the antibody binds to CRIPTO.
In one embodiment, the antibody binds to CD21.
In one embodiment, the antibody binds to CD79b.
In one embodiment, the antibody binds to FcRH2.
In one embodiment, the antibody binds to HER2.
In one embodiment, the antibody binds to NCA.
In one embodiment, the antibody binds to MDP.
In one embodiment, the antibody binds to IL20Rα.
In one embodiment, the antibody binds to Brevican.
In one embodiment, the antibody binds to EphB2R.
In one embodiment, the antibody binds to ASLG659.
In one embodiment, the antibody binds to PSCA.
In one embodiment, the antibody binds to GEDA.
In one embodiment, the antibody binds to BAFF-R.
In one embodiment, the antibody binds to CD22.
In one embodiment, the antibody binds to CD79a.
In one embodiment, the antibody binds to CXCR5.
In one embodiment, the antibody binds to HLA-DOB.
In one embodiment, the antibody binds to P2X5.
In one embodiment, the antibody binds to CD72.
In one embodiment, the antibody binds to LY64.
In one embodiment, the antibody binds to FcRH1.
In one embodiment, the antibody binds to IRTA2.
In one embodiment, the antibody binds to TENB2.
In one embodiment, the antibody binds to PMEL17.
In one embodiment, the antibody binds to TMEFF1.
In one embodiment, the antibody binds to GDNF-Ra1.
In one embodiment, the antibody binds to Ly6E.
In one embodiment, the antibody binds to TMEM46.
In one embodiment, the antibody binds to Ly6G6D.
In one embodiment, the antibody binds to LGR5.
In one embodiment, the antibody binds to RET.
In one embodiment, the antibody binds to LY6K.
In one embodiment, the antibody binds to GPR19.
In one embodiment, the antibody binds to GPR54.
In one embodiment, the antibody binds to ASPHD1.
In one embodiment, the antibody binds to Tyrosinase.
In one embodiment, the antibody binds to TMEM118.
In one embodiment, the antibody binds to GPR172A.
In one embodiment, the antibody binds to CD33.

The parent antibody may also be a fusion protein comprising an albumin-binding peptide (ABP) sequence (Dennis et al. (2002) "Albumin Binding As A General Strategy For Improving The Pharmacokinetics Of Proteins" J Biol Chem. 277:35035-35043; WO 01/45746). Antibodies of the invention include fusion proteins with ABP sequences taught by: (i) Dennis et al (2002) J Biol Chem. 277:35035-35043 at Tables III and IV, page 35038; (ii) US 20040001827 at [0076]; and (iii) WO 01/45746 at pages 12-13, and all of which are incorporated herein by reference. Antibodies may be produced using recombinant methods and compositions, e.g., as described in U.S. Pat. No. 4,816,567 and known in the art. In some embodiments, the antibody is produced in a eukaryotic host cell (e.g., mammalian host cell). In some embodiments, the antibody is produced in a prokaryotic host cell (e.g., E. coli).

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g., a substitution) at one or more amino acid positions.

In certain embodiments, the invention contemplates an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability.

Drug Loading of ADC

The drug loading is the average number of drug moieties per antibody. Drug loading may range from 1 to 8 drugs (D) per antibody (Ab), i.e. where 1, 2, 3, 4, 5, 6, 7, and 8 drug moieties are covalently attached to the antibody. Compositions of ADC include collections of antibodies conjugated with a range of drugs, from 1 to 8. The average number of drugs per antibody in preparations of ADC from conjugation reactions may be characterized by conventional means such as mass spectroscopy, ELISA assay, electrophoresis, and HPLC. The quantitative distribution of ADC in terms of p may also be determined. By ELISA, the averaged value of p in a particular preparation of ADC may be determined (Hamblen et al (2004) Clin. Cancer Res. 10:7063-7070;

Sanderson et al (2005) Clin. Cancer Res. 11:843-852). However, the distribution of p (drug) values is not discernible by the antibody-antigen binding and detection limitation of ELISA. Also, ELISA assay for detection of antibody-drug conjugates does not determine where the drug moieties are attached to the antibody, such as the heavy chain or light chain fragments, or the particular amino acid residues. In some instances, separation, purification, and characterization of homogeneous ADC where p is a certain value from ADC with other drug loadings may be achieved by means such as reverse phase HPLC or electrophoresis.

For some antibody-drug conjugates, p may be limited by the number of attachment sites on the antibody. For example, an antibody may have only one or several cysteine thiol groups, or may have only one or several sufficiently reactive thiol groups through which a linker may be attached. Higher drug loading, e.g. p>5, may cause aggregation, insolubility, toxicity, or loss of cellular permeability of certain antibody-drug conjugates.

Typically, fewer than the theoretical maximum of drug moieties is conjugated to an antibody during a conjugation reaction. An antibody may contain, for example, many lysine residues that do not react with the linker-drug intermediate (X-L-D) or linker reagent. Only the most reactive lysine groups may react with an amine-reactive linker reagent. Also, only the most reactive cysteine thiol groups may react with a thiol-reactive linker reagent or linker-drug intermediate. Generally, antibodies do not contain many, if any, free and reactive cysteine thiol groups which may be linked to a drug moiety. Most cysteine thiol residues in the antibodies of the compounds exist as disulfide bridges and must be reduced with a reducing agent such as dithiothreitol (DTT) or TCEP, under partial or total reducing conditions. The loading (drug/antibody ratio, "DAR") of an ADC may be controlled in several different manners, including: (i) limiting the molar excess of linker-drug intermediate or linker reagent relative to antibody, (ii) limiting the conjugation reaction time or temperature, and (iii) partial or limiting reductive conditions for cysteine thiol modification.

Where more than one nucleophilic or electrophilic group of the antibody reacts with a linker-drug intermediate, or linker reagent followed by dimer drug moiety reagent, then the resulting product is a mixture of Antibody-drug conjugate s with a distribution of drug moieties attached to an antibody, e.g. 1, 2, 3, etc. Liquid chromatography methods such as polymeric reverse phase (PLRP) and hydrophobic interaction (HIC) may separate compounds in the mixture by drug loading value. Preparations of ADC with a single drug loading value (p) may be isolated, however, these single loading value ADCs may still be heterogeneous mixtures because the drug moieties may be attached, via the linker, at different sites on the antibody. Thus the antibody-drug conjugate compositions of the invention include mixtures of antibody-drug conjugate compounds where the antibody has one or more drug moieties and where the drug moieties may be attached to the antibody at various amino acid residues.

Exemplary Drug Moieties

Examples of drugs containing tertiary amine or pyridine functional groups include, but not limited to, topotecan, LB-100, IB-01212, Mcl-1 inhibitors, 68Ga-BNOTA-PRGD2, Venetoclax, technetium Tc 99mtilmanocept, E-7016, HM-30181AK, paclitaxel, AS-1896596, EM-015, Gadoteridol, BGJ-398, EC-1456, Dovitinib, pyrroltinib maleate, GSK-923295, irinotecan, BGP-15, 90Y-edotreotide, mibefradil, resminostat, itarnafloxin, NMS-P153, NMS-P937, irinotecansucrosofate, abiraterone, A-366, SB-743921, Gilteritinib, Abemaciclib, IPP-204106, Vinflunine, CX-5461, doxycycline, TP-0903, TLK-58747, irinotecan, numonafide, ON-123300, Vintafolide, KX2391, gadopentetatedimeglumine, gedatolisib, tasidotin HCl, Genzyme/Ergomed, TTL-1177, Naltrexone, CFI-400945 fumarate, Pictilisib, Felotaxel, OTX-008, Banoxantrone, G-773, Trabectedin, NO-saquinavir, ENMD-2076, Gadobutrol, BGB-102, Ga68-labeled, scutellarin conjugates, THZ-1, TSR-011, ONC-201, ASP-3026, galactosylceramide-enhanced vinorelbine, PMX-20005, 111In-RP-782, DSR-6434, vincristine sulfate, J-21475, Apitolisib, MDX-1203, gallium-68-SH-7139, CNX-1351, CT-1578, TG-02, imatinib, luminespib, vindesine-CB-3717 conjugates, AMG511, AZD1152hQPA Accurins, Mepacrine, CGM-097, TR-100, BGB-324, CEP-37440, OTSSP-167, APR-246, Indotecan, gadoterate meglumine, lucanthone, navitoclax, samarium (153Sm) lexidronam, DMDAPatA, OCT-1002, irinotecan hydrochloride, BAY-87-2243, SIMM-559, CEP-33779, XL-388, SHR-1258, Voruciclib, UNBS-5162, noscapine, artemisinin, PHA-665752, pyrrolobenzodiazepines, folate-vindesine hydrazide conjugate, BRN-103, NSC-134754, AMP-53, PKI-402, Tariquidar, CG-200745, VO-100, PRLX-93936, Cenisertib, SSR-125329, CRD-401, SN-24771, Balamapimod, BIBX-1382, 105509, KW-2152, Lidamycin, CT-17, SN-23490, L-000021649, U-74389G, JNJ-17029259, PAK-200, PFP-6, XR-842, RP-697, NCO-700, B-220, Pazelliptine, R-116010, NL-2001, RC-3940-II, BIM-46068, MDL-73811, CHIR-200131, Halitulin, Flezelastine, Cinchonine, BN-52207, ABT-546, NSC-639366, datelliptium chloride, WR-63320, LY-329146, dolaphenine androstaneSR-25989, XR-9051, RSU-1069, N-1379, epelmycin A, PNU-144113, FCE-27726, NSC-357704, PD-171851, DZ-3358, B-9309-068, Goe-7874, Ro-44-5912, MDL-103323, Mofarotene, Ro-46-7864, RU-45144, Win-63320, NC-190, NSC-646958, VA-033, GI-149893, BBR-2378, NSC-639365, Vinfosiltine, SDZ-62-434, BCH-2051, RB-90745, TI-356, ER-37328, SR-26050, CL-329753, LY-326315, AN-1006, CP-117227, R-teludipine, RB-90740, SYUIQ-05, SR-16388, SN-28049, SN-30000, topotecan hydrochloride, vinorelbine, WBZ-7, S-44563, GSK-1070916, RPR-203360, desmethyl, desaminopateamine A, EU-517, AT-9283, spirogermanium hydrochloride, E-7974, Azoacridone, vinorelbine, GTx-134, astemizole, retelliptine, mitonafide, rimcazole, PBT-1, Atiprimod, Topixantrone, A-620223, tridolgosir, tesetaxel EMD-94283, A-923573, E-7107, NRC-2694, alvespimycin hydrochloride, SMT-14400, PHA-793887, HB-19, S-12363, Soblidotin, CEP-28122, TKS-040, ABT-306552, ATI-1025, A-928605, PF-3758309, 99mTc-RP-527, MLN-576, K-454, W-198, Debio-0931, Zosuquidar, PF-337210, ABT-737, folatetubulysin conjugates, elacridar, CP-31398, AV-412, Elomotecan, GSK-1838705A, ABT-839, AEW-541, vincristine, gefitinib, doxorubicin, YHO-13351, Pelitinib, Cemadotin, A-947864, Tozasertib, PD-115934, dolastatin-10, SU-11274, omacetaxine mepesuccinate, EHT-1864, Dofequidar, DX-52-1, RTA-502, Canertinib, metoclopramide, BMS-753493, PD-166285, auristatin PYE, Alchemix, C-1305, ANG-1009, procaine hydrochloride, siramesine, Hoe-33342, Manzamines, OSI-632, STX-1801, BIBF-1000, lurtotecan, ZK-191703, Tiamulin, VX-322, docetaxel, Ro-28-2653, Becatecarin, GS-164, INK-401, Tamolarizine, Pibrozelesin, S-16020-2, NK-611, Ladirubicin, TOP-008, Declopramide, Lurtotecan, TAS-103, Dexniguldipine, BAM-1120, Conophylline, ICRF-193, Anhydrovinblastine, tubulysin, ecteinascidins, and L-745631.

Indications and Methods of Treatment

It is contemplated that the antibody-drug conjugates (ADC) of the present invention may be used to treat various diseases or disorders, e.g. characterized by the overexpression of a tumor antigen. Exemplary conditions or hyperproliferative disorders include benign or malignant solid tumors and hematological disorders such as leukemia and lymphoid malignancies. Others include neuronal, glial, astrocytal, hypothalamic, glandular, macrophagal, epithelial, stromal, blastocoelic, inflammatory, angiogenic and immunologic, including autoimmune, disorders.

In certain embodiments, an ADC of the invention comprising an anti-NaPi2b antibody, such as those described above, is used in a method of treating solid tumor, e.g., ovarian. In another embodiment, an ADC of the invention comprising an anti-CD33 antibody, such as those described herein, is used in a method of treating hematological malignancies such as non-Hodgkin's lymphoma (NHL), diffuse large hematopoietic lymphoma, follicular lymphoma, mantle cell lymphoma, chronic lymphocytic leukemia, multiple myeloma, acute myeloid leukemia (AML), and myeloid cell leukemia (MCL), and including B-cell related cancers and proliferative disorders. See: U.S. Pat. No. 8,226,945; Li et al (2013) Mol. Cancer. Ther. 12(7):1255-1265; Polson et al (2010) Leukemia 24:1566-1573; Polson et al (2011) Expert Opin. Investig. Drugs 20(1):75-85, the contents of which are incorporated by reference.

In another embodiment, an ADC of the invention comprising an anti-MUC16 antibody, such as those described herein, is used in a method of treating ovarian, breast and pancreatic cancers. The cancer may be associated with the expression or activity of a MUC16/CA125/0772P polypeptide. See: WO 2007/001851; U.S. Pat. Nos. 7,989,595; 8,449,883; 7,723,485; Chen et al (2007) Cancer Res. 67(10): 4924-4932; Junutula, et al., (2008) Nature Biotech., 26(8): 925-932, the contents of which are incorporated by reference.

In certain embodiments, an ADC of the invention comprising an anti-HER2 antibody, such as those described above, is used in a method of treating cancer, e.g., breast or gastric cancer, more specifically HER2+ breast or gastric cancer, wherein the method comprises administering such ADC to a patient in need of such treatment. In one such embodiment, the ADC comprises the anti-HER2 antibody trastuzumab or pertuzumab.

Generally, the disease or disorder to be treated is a hyperproliferative disease such as cancer. Examples of cancer to be treated herein include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

Autoimmune diseases for which the Antibody-drug conjugate s may be used in treatment include rheumatologic disorders (such as, for example, rheumatoid arthritis, Sjögren's syndrome, scleroderma, lupus such as systemic lupus erythematosus (SLE) and lupus nephritis, polymyositis/dermatomyositis, cryoglobulinemia, anti-phospholipid antibody syndrome, and psoriatic arthritis), osteoarthritis, autoimmune gastrointestinal and liver disorders (such as, for example, inflammatory bowel diseases (e.g., ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-associated vasculitis, including Churg-Strauss vasculitis, Wegener's granulomatosis, and polyarteritis), autoimmune neurological disorders (such as, for example, multiple sclerosis, opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, and autoimmune thyroid disease (e.g., Graves' disease and thyroiditis)). More preferred such diseases include, for example, rheumatoid arthritis, ulcerative colitis, ANCA-associated vasculitis, lupus, multiple sclerosis, Sjögren's syndrome, Graves' disease, IDDM, pernicious anemia, thyroiditis, and glomerulonephritis.

For the prevention or treatment of disease, the appropriate dosage of an ADC will depend on the type of disease to be treated, as defined above, the severity and course of the disease, whether the molecule is administered for preventive or therapeutic purposes, previous therapy, the patient's clinical history and response to the antibody, and the discretion of the attending physician. The molecule is suitably administered to the patient at one time or over a series of treatments. Depending on the type and severity of the disease, about 1 μg/kg to 15 mg/kg (e.g. 0.1-20 mg/kg) of molecule is an initial candidate dosage for administration to the patient, whether, for example, by one or more separate administrations, or by continuous infusion. A typical daily dosage might range from about 1 μg/kg to 100 mg/kg or more, depending on the factors mentioned above. An exemplary dosage of ADC to be administered to a patient is in the range of about 0.1 to about 10 mg/kg of patient weight.

EXPERIMENTALS

Example 1 (MC-Sq-Cit-PAB-Dolastatin10)

[4-[[(2S)-2-[[1-[5-(2,5-dioxopyrrol-1-yl)pentylcarbamoyl]cyclobutanecarbonyl]amino]-5-ureido-pentanoyl]amino]phenyl]methyl-[(1S)-1-[[(1S)-1-[[(1S,2R)-2-methoxy-4-[(2S)-2-[(1R,2R)-1-methoxy-2-methyl-3-oxo-3-[[(1S)-2-phenyl-1-thiazol-2-yl-ethyl]amino]propyl]pyrrolidin-1-yl]-1-[(1S)-1-methylpropyl]-4-oxo-butyl]-methyl-carbamoyl]-2-methyl-propyl]carbamoyl]-2-methyl-propyl]-dimethyl-ammonium extra equivalent of base was added, which improved product formation and gave clearer LC/MS peaks.

The reaction mixture was diluted with DMF and then purified directly on an HPLC under formic acid conditions. One pure fraction of [4-[[(2S)-2-[[1-[5-(2,5-dioxopyrrol-1-yl)pentylcarbamoyl]cyclobutanecarbonyl]amino]-5-ureido-pentanoyl]amino]phenyl]methyl-[(1S)-1-[[(1S)-1-[[(1S,2R)-2-methoxy-4-[(2S)-2-[(1R,2R)-1-methoxy-2-methyl-3-oxo-3-[[(1S)-2-phenyl-1-thiazol-2-yl-ethyl]amino]propyl]pyrrolidin-1-yl]-1-[(1S)-1-methylpropyl]-4-oxo-butyl]-methyl-carbamoyl]-2-methyl-propyl]carbamoyl]-2-methyl-propyl]-dimethyl-ammonium (100 mass %, C, 5 mg,

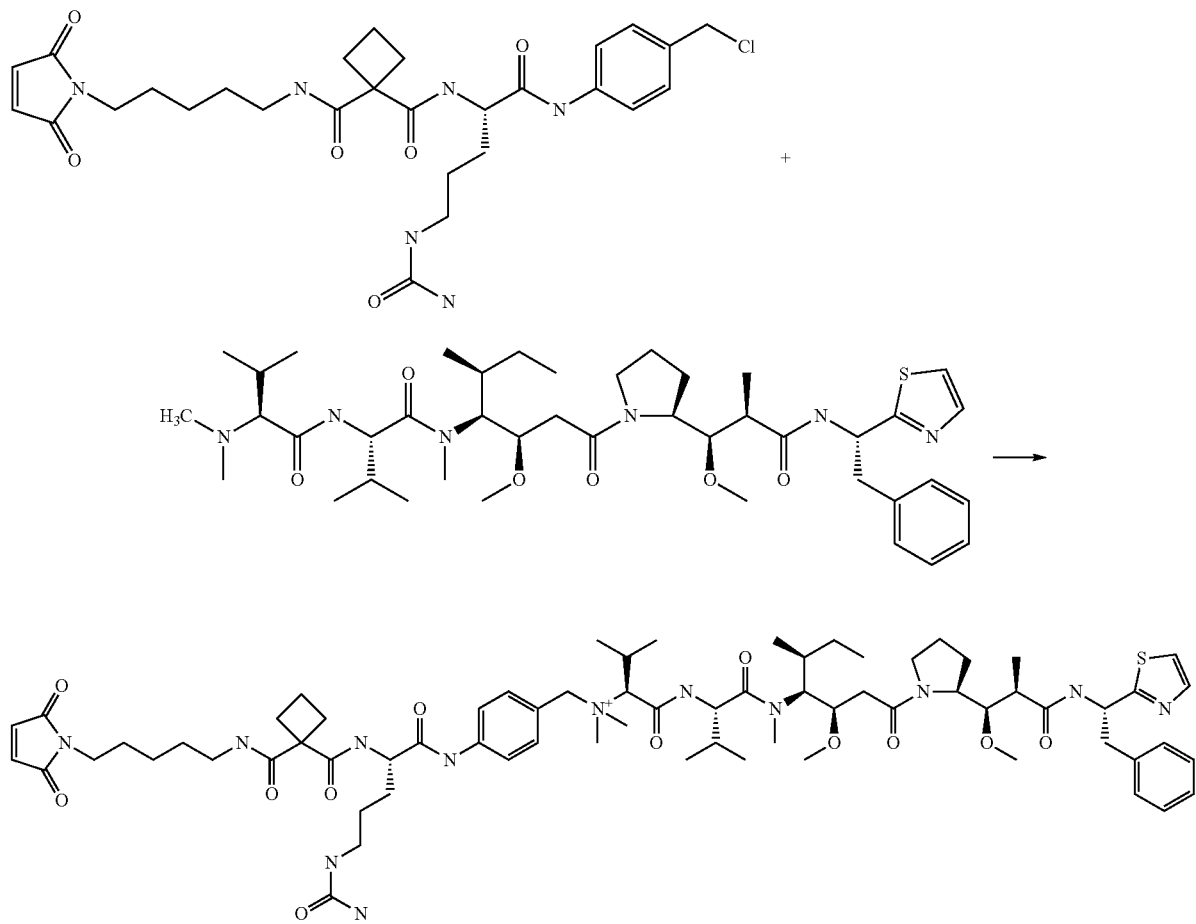

In a small vial, N1'-[(1S)-1-[[4-(chloromethyl)phenyl]carbamoyl]-4-ureido-butyl]-N1-[5-(2,5-dioxopyrrol-1-yl)pentyl]cyclobutane-1,1-dicarboxamide (100 mass %, 1 equiv., 0.04713 mmol, 1.000, 27.76 mg), Dolastatin 10 (100 mass %, 37 mg, 0.04713 mmol, 1.000, 37 mg) and tetrabutylammonium iodide (65.65 mass %, 0.3 equiv., 0.01414 mmol, 0.3000, 7.956 mg) were combined and dissolved in N,N-dimethylformamide (100 mass %, 50 μL, 0.646 mmol, 13.7, 47.3 mg, 0.05 mL). The mixture was stirred at RT for 3 hours and no reaction was observed. To the reaction mixture was added N,N-diisopropylethylamine (100 mass %, 1.5 equiv., 0.07069 mmol, 1.500, 9.136 mg, 0.0123 mL). The reaction mixture stirred overnight at room temperature. LC/MS, of the reaction mixture showed 16% product. An 0.0037350 mmol, 0.07925, 5 mg) M/Z=1338.1 (7.9% yield of one pure fraction) was obtained and one impure fraction was obtained.

1H NMR (400 MHz, DMSO-d6) δ 10.47 (d, J=2.5 Hz, 1H), 8.92 (q, J=9.0 Hz, 1H), 8.31 (s, 4H), 8.05-7.91 (m, 0H), 7.91-7.75 (m, 4H), 7.67 (s, 0H), 7.63 (d, J=3.2 Hz, 0H), 7.62-7.54 (m, 0H), 7.54 (s, 0H), 7.58-7.45 (m, 2H), 7.33-7.11 (m, 5H), 7.08-6.95 (m, 2H), 6.13 (t, J=5.6 Hz, 1H), 5.75 (s, 1H), 5.57-5.37 (m, 3H), 4.76-4.55 (m, 3H), 4.41 (dt, J=15.5, 6.0 Hz, 1H), 3.98 (q, J=6.3 Hz, 2H), 3.61-3.28 (m, 4H), 3.28-3.07 (m, 9H), 3.07-2.87 (m, 10H), 2.84-2.68 (m, 1H), 2.49-2.31 (m, 6H), 2.31-1.90 (m, 0H), 1.88-1.54 (m, 7H), 1.41 (ddt, J=28.5, 22.6, 10.5 Hz, 10H), 1.18 (tdd, J=19.3, 7.8, 4.5 Hz, 3H), 1.12-1.02 (m, 5H), 1.02-0.91 (m, 5H), 0.91-0.82 (m, 6H), 0.79 (td, J=7.4, 3.0 Hz, 4H).

Example 2 (MC-Sq-Cit-PAB-TubulysinM)

(2R)-2-((2S,3S)-1-(((1R,3R)-1-acetoxy-1-(4-((2R,4S)-4-carboxy-1-phenylpentan-2-ylcarbamoyl)thiazol-2-yl)-4-methylpentan-3-yl)(methyl)amino)-3-methyl-1-oxopentan-2-ylcarbamoyl)-1-(4-((S)-2-(1-(5-(2,5-dioxo-2,5-dihydro-1H-pyrrol-1-yl)pentylcarbamoyl)cyclobutanecarboxamido)-5-ureidopentanamido)benzyl)-1-methylpiperidinium product formed. The reaction mixture was then stirred for overnight at RT and then 1 extra equivalent of base was added and the mixture stirred for the rest of the day. Desired product was then observed, diluted and purified on HPLC to avoid any loss of product.

(2S,4R)-4-[[2-[(1R,3R)-1-acetoxy-3-[[(2S,3S)-2-[[(2R)-1-[[4-[[(2S)-2-[[1-[5-(2,5-dioxopyrrol-1-yl)pentylcarbamoyl]cyclobutanecarbonyl]amino]-5-ureido-pentanoyl]amino]phenyl]methyl]-1-methyl-piperidin-1-ium-2-

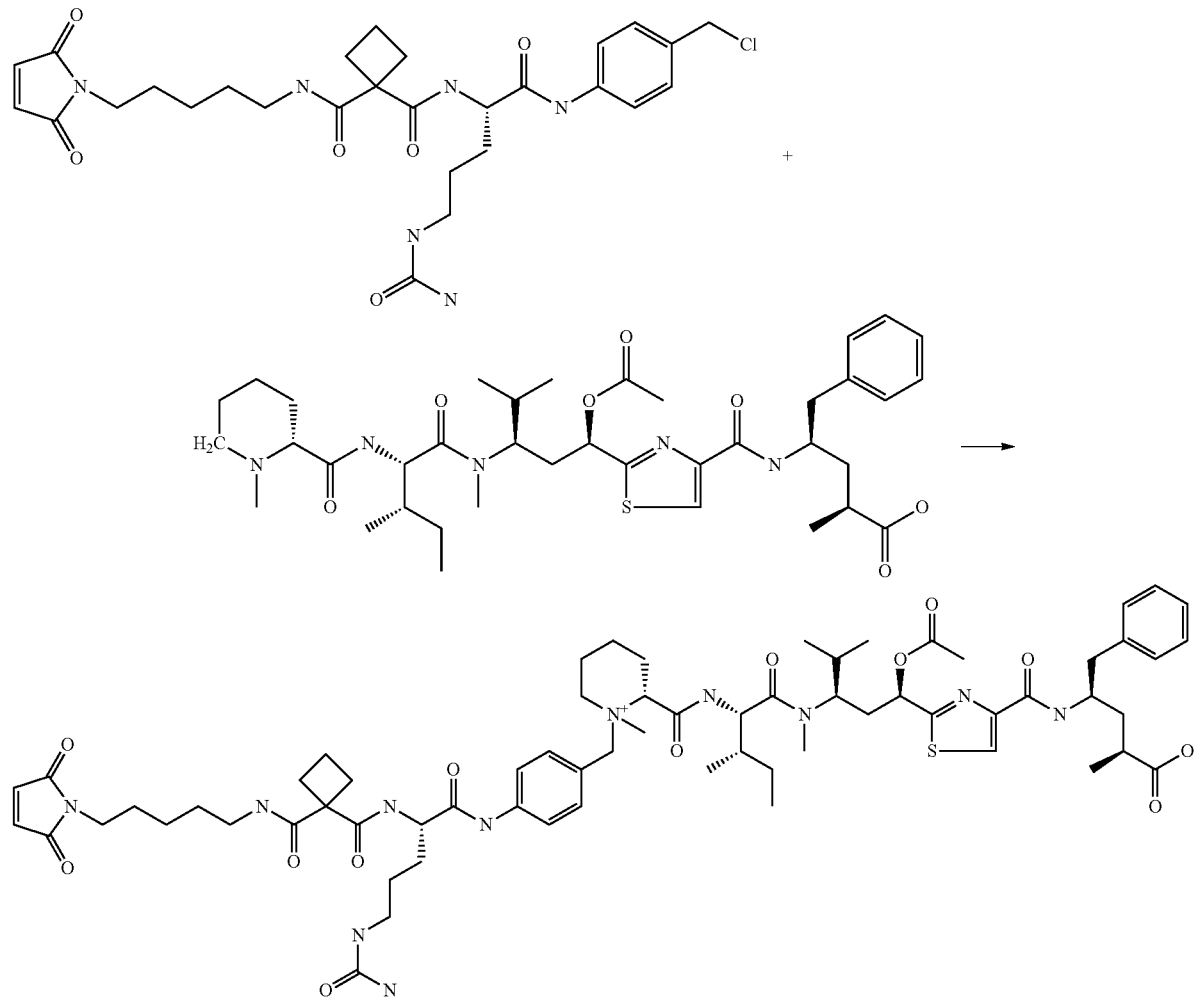

carbonyl]amino]-3-methyl-pentanoyl]-methyl-amino]-4-methyl-pentyl]thiazole-4-carbonyl]amino]-2-methyl-5-phenyl-pentanoic acid (100 mass %, 11.7 mg, 0.0091292 mmol, 0.3164, 11.7 mg) was isolated. 31.64% yield. HRMS: M/Z=1281.6780

In a small vial, N1'-[(1S)-1-[[4-(chloromethyl)phenyl]carbamoyl]-4-ureido-butyl]-N1-[5-(2,5-dioxopyrrol-1-yl)pentyl]cyclobutane-1,1-dicarboxamide (100 mass %, 17 mg, 0.02886 mmol, 1.000, 17 mg), (2S,4R)-4-[[2-[(1R,3R)-1-acetoxy-4-methyl-3-[methyl-[(2S,3S)-3-methyl-2-[[(2R)-1-methylpiperidine-2-carbonyl]amino]pentanoyl]amino]pentyl]thiazole-4-carbonyl]amino]-2-methyl-5-phenyl-pentanoic acid (100 mass %, 1 equiv., 0.02886 mmol, 1.000, 21.01 mg) and tetrabutylammonium iodide (65.65 mass %, 0.3 equiv., 0.008657 mmol, 0.3000, 4.872 mg) were taken up in N,N-dimethylformamide (100 mass %, 75 µL, 0.970 mmol, 33.6, 70.9 mg, 0.075 mL). The resulting reaction mixture was stirred for 1 hour at RT and no desired product was observed. To the reaction mixture was added N,N-diisopropylethylamine (100 mass %, 1.1 equiv., 0.03174 mmol, 1.100, 4.103 mg, 0.00554 mL) and a slight amount of 1H NMR (500 MHz, DMSO-d6) δ 10.80 (s, 2H), 9.50 (s, 2H), 8.48 (s, 6H), 8.36 (s, 3H), 8.12 (s, 2H), 8.05 (s, 1H), 7.75 (s, 3H), 7.33-7.26 (m, 4H), 7.26-7.18 (m, 5H), 7.13 (d, J=7.6 Hz, 5H), 6.99 (d, J=5.7 Hz, 2H), 6.42 (s, 2H), 5.73 (s, 2H), 5.56 (s, 3H), 4.64 (s, 4H), 4.57 (t, J=7.8 Hz, 2H), 4.38 (dq, J=15.0, 5.4 Hz, 2H), 4.13 (dd, J=13.0, 7.6 Hz, 2H), 3.05 (q, J=6.9, 6.2 Hz, 12H), 3.00-2.87 (m, 10H), 2.84-2.70 (m, 3H), 2.50 (s, 2H), 2.40 (hept, J=13.1, 10.5 Hz, 9H), 2.25 (d, J=11.2 Hz, 1H), 2.18-1.94 (m, 0H), 1.91-1.64 (m, 0H), 1.58 (s, 0H), 1.42 (ddt, J=23.8, 16.7, 8.4 Hz, 15H), 1.32-1.23 (m, 12H), 1.17 (p, J=8.3, 7.4 Hz, 6H), 1.11-0.99 (m, 6H), 0.94-0.85 (m, 12H), 0.80 (q, J=7.6 Hz, 10H).

Example 3 (Nitro-MM-PDS-PAB-Tubulysin M)

(2S,4R)-4-[[2-[(1R,3R)-1-acetoxy-4-methyl-3-[methyl-[(2S,3S)-3-methyl-2-[[(2R)-1-methyl-1-[[4-[[(2R)-2-[(6-nitro-3-pyridyl)disulfanyl]propoxy]carbonylamino]phenyl]methyl]piperidin-1-ium-2-carbonyl]amino]pentanoyl]amino]pentyl]thiazole-4-carbonyl]amino]-2-methyl-5-phenyl-pentanoic Acid

Step 1:
Mono Methyl-Nitro-PDS-PAB-Cl

Mono methyl (R)-2-((6-nitropyridin-3-yl)disulfanyl)propyl 4-(chloromethyl)phenylcarbamate

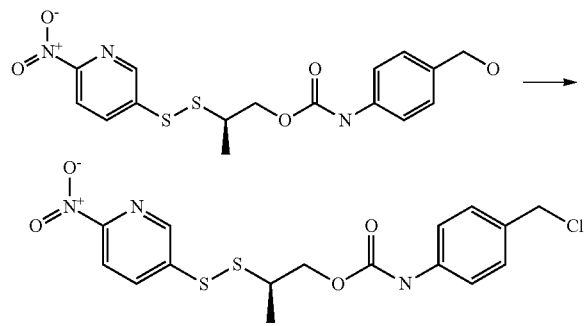

In a small vial, mono methyl (R)-2-((6-nitropyridin-3-yl)disulfanyl)propyl 4-(hydroxymethyl)phenylcarbamate (-Nitro-PDS-PAB-OH)(100 mass %, 50 mg, 0.1265 mmol, 1.000, 50 mg) was dissolved in N,N-dimethylformamide (100 mass %, 0.2 mL, 3 mmol, 20, 200 mg, 0.2 mL). The resulting reaction mixture was cooled in an ice bath and a solution of thionyl chloride (100 mass %, 1.2 equiv., 0.1517 mmol, 1.200, 18.05 mg, 0.01106 mL) in dichloromethane (100 mass %, 50 µL, 0.7800 mmol, 6.168, 66.25 mg, 0.05 mL) was added dropwise. The reaction mixture was removed from the ice bath and after 30 minutes of stirring at RT, LCMS showed desired product. One (1) extra equivalent of thionyl chloride was added as a solution in DCM dropwise to the reaction mixture and stirred overnight at RT. A new LCMS peak formed close to the product peak with a mass of 438. The reaction mixture was diluted with ethyl acetate, quenched with water, the organic layer washed twice with water, dried over MgSO₄ and concentrated onto silica and was purified by flash chromatography eluting with 30% EtOAc/Heptane. A white solid was isolated. LC/MS showed material to have an alcohol precursor as an impurity. Mono methyl (R)-2-((6-nitropyridin-3-yl)disulfanyl)propyl 4-(chloromethyl)phenylcarbamate (-Nitro-PDS-PAB-Cl) (100 mass %, B, 38 mg, 0.09181 mmol, 0.7260, 38 mg). (72.6% yield) M/Z=414.00

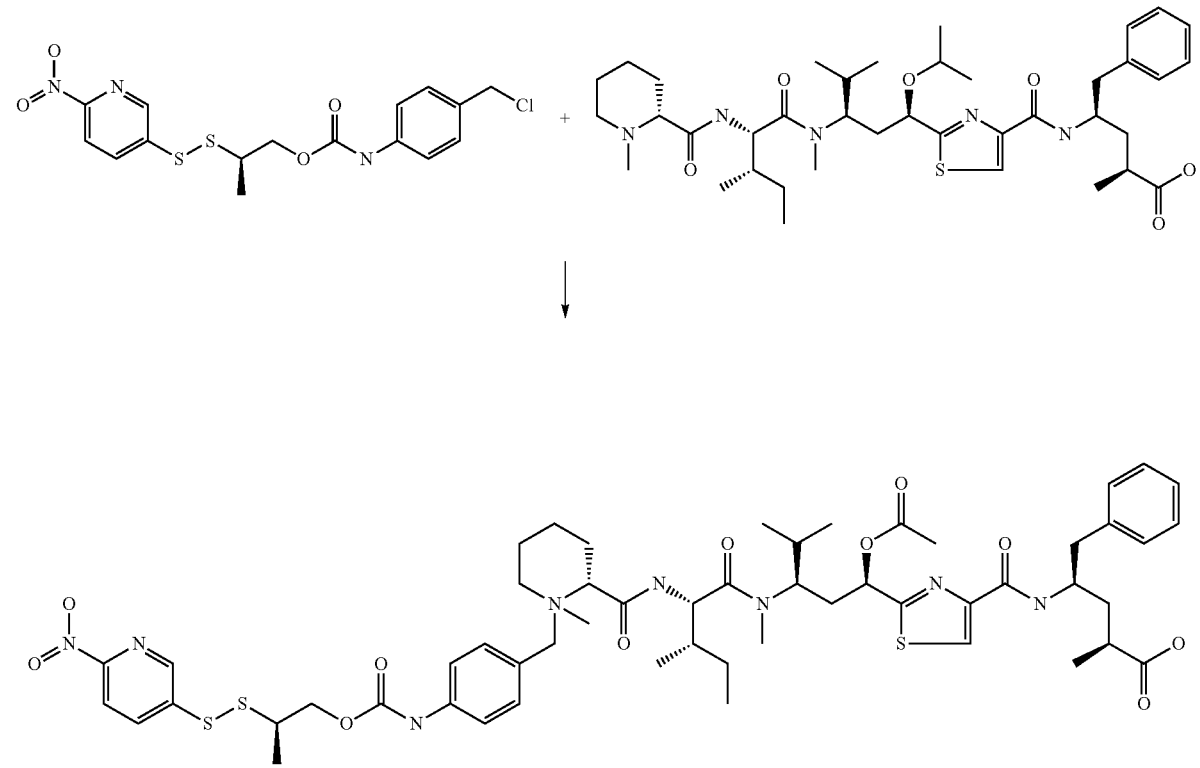

In a small vial, [(2R)-2-[(6-nitro-3-pyridyl)disulfanyl] propyl] N-[4-(chloromethyl)phenyl]carbamate (100 mass %) and (2S,4R)-4-[[2-[(1R,3R)-1-acetoxy-4-methyl-3-[methyl-[(2S,3S)-3-methyl-2-[[(2R)-1-methylpiperidine-2-carbonyl]amino]pentanoyl]amino]pentyl]thiazole-4-carbonyl]amino]-2-methyl-5-phenyl-pentanoic acid (100 mass %, 9.6 mg, 0.013 mmol, 1.0, 9.6 mg) were taken up in N,N-dimethylformamide (100 mass %). To the reaction mixture was added tetrabutylammonium iodide (65.65 mass %, 0.2 equiv., 0.0026 mmol, 0.20, 1.5 mg) followed by N,N-diisopropylethylamine (100 mass %, 1 equiv., 0.013 mmol, 1.0, 1.7 mg, 0.0023 mL). The reaction mixture was warmed to 38° C. for 20 minutes then stirred at RT for 2 hours. LC/MS showed desired product. The reaction was stopped about half way to avoid decomposition, diluted with DMF, and purified directly on HPLC under acidic conditions. (2S,4R)-4-[[2-[(1R,3R)-1-acetoxy-4-methyl-3-[methyl-[(2S,3S)-3-methyl-2-[[(2R)-1-methyl-1-[[4-[[(2R)-2-[(6-nitro-3-pyridyl)disulfanyl]propoxy]carbonylamino]phenyl]methyl]piperidin-1-ium-2-carbonyl]amino]pentanoyl]amino]pentyl]thiazole-4-carbonyl]amino]-2-methyl-5-phenyl-pentanoic acid was isolated. (100 mass %, 4.6 mg, 0.0041576 mmol, 0.32, 4.6 mg) (32% yield), M/Z=1106.4.

Example 4 (MC-Sq-Cit-PAB-DuocarmycinDM)

Preparation of 2-[[2-[(1S)-1-(chloromethyl)-5-hydroxy-1,2-dihydrobenzo[e]indole-3-carbonyl]-1H-indol-5-yl]oxy]ethyl-[[4-[[(2S)-2-[[1-[5-(2,5-dioxopyrrol-1-yl)pentylcarbamoyl]cyclobutanecarbonyl]amino]-5-ureido-pentanoyl]amino]phenyl]methyl]-dimethyl-ammonium Step 1: (S)—N-(5-(2,5-dioxo-2,5-dihydro-1H-pyrrol-1-yl)pentyl)-N-(1-(4-(hydroxymethyl)phenylamino)-1-oxo-5-ureidopentan-2-yl)cyclobutane-1,1-dicarboxamide

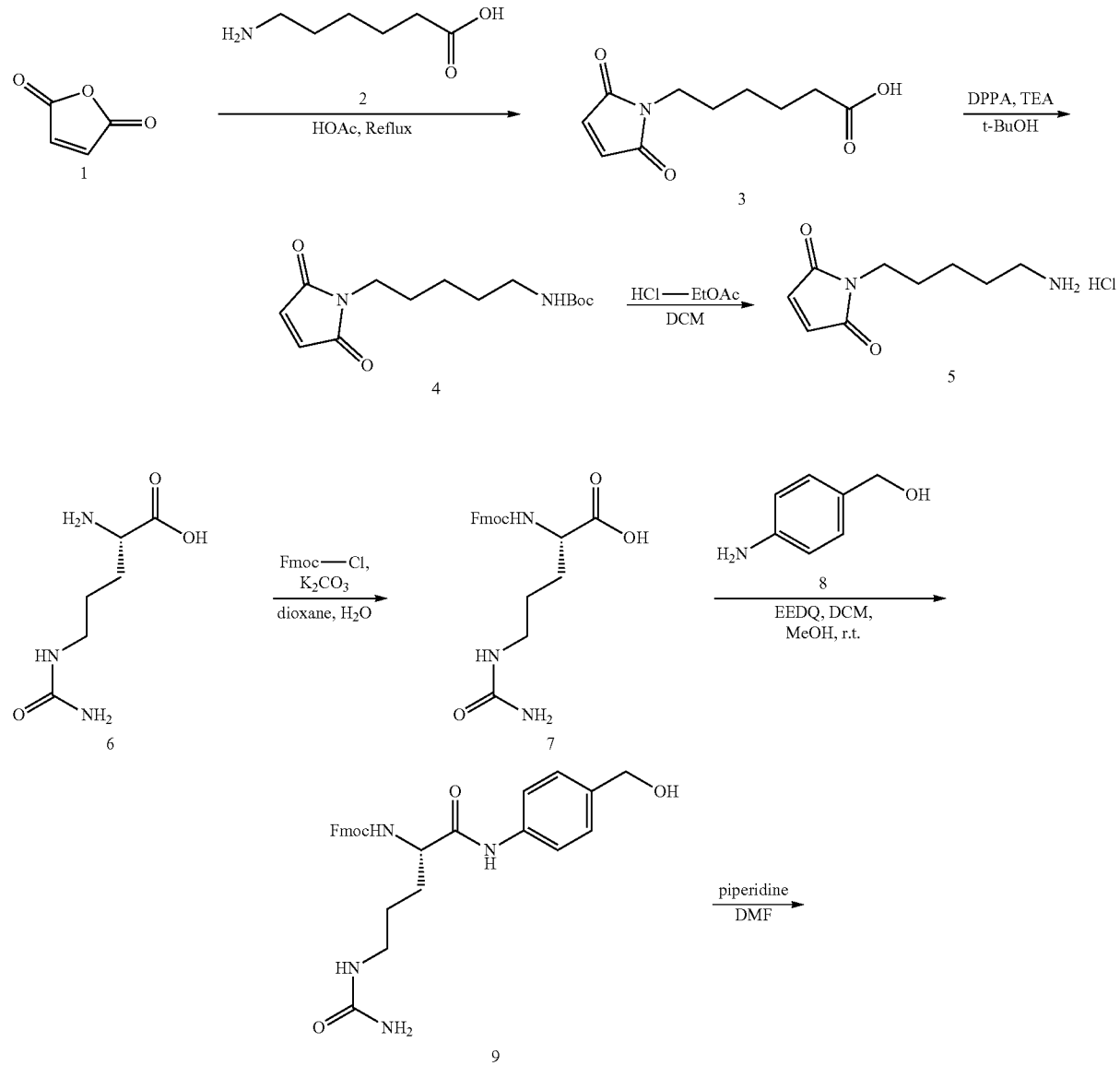

-continued
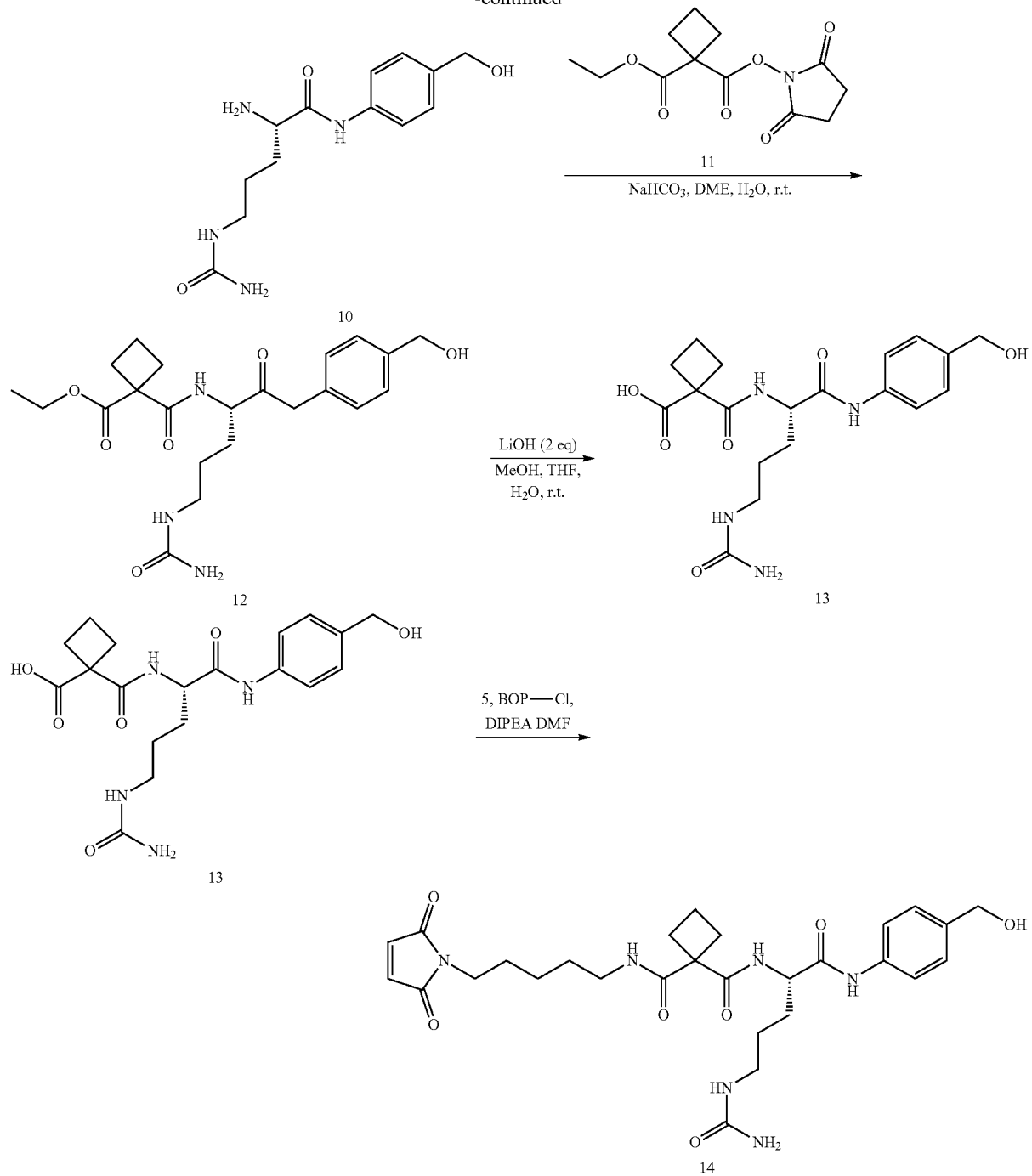
Procedure
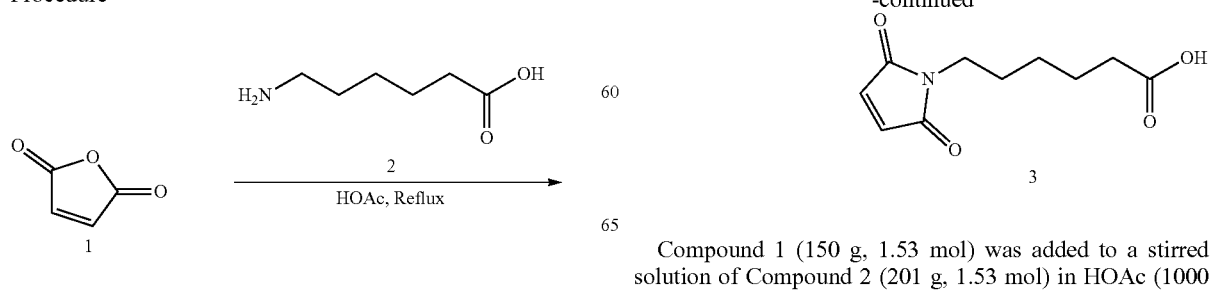
Compound 1 (150 g, 1.53 mol) was added to a stirred solution of Compound 2 (201 g, 1.53 mol) in HOAc (1000 mL). After the mixture was stirred at r.t. for 2 h, it was heated at reflux for 8 h. The organic solvents were removed under reduced pressure and the residue was extracted with EtOAc (500 mL×3), and washed with H₂O. The combined organic layers were dried over Na₂SO₄ and concentrated to give the product. The resulting product was washed with petroleum ether to give compound 3 as white solid (250 g, 77.4%).

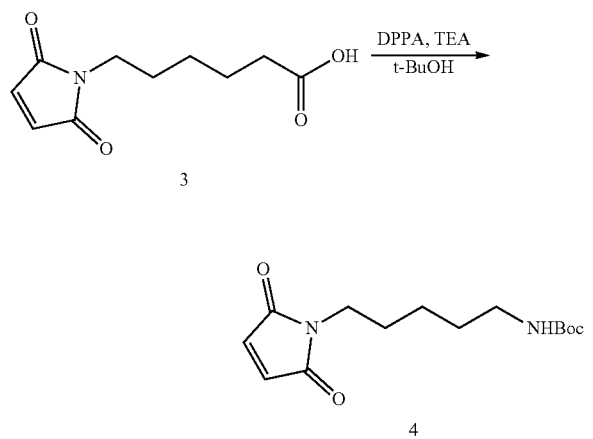

DPPA (130 g, 473 mmol) and TEA (47.9 g, 473 mmol) was added to a solution of compound 3 (100 g, 473 mmol) in t-BuOH (200 mL). The mixture was heated at reflux for 8 h under N₂. The mixture was concentrated, and the residue was purified by column chromatography on silica gel (PE: EtOAc=3:1) to give compound 4 (13 g, 10%).

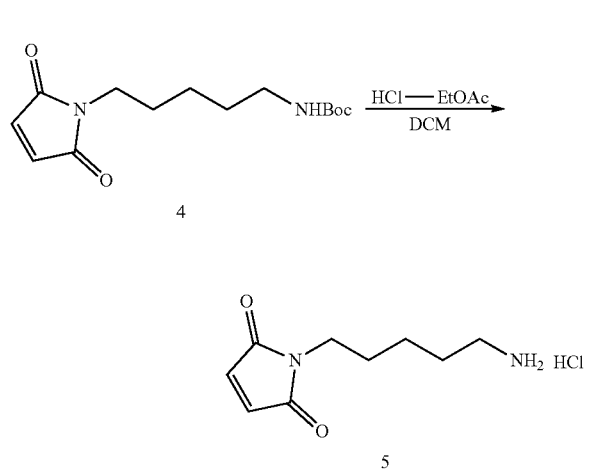

To a solution of compound 4 (28 g, 992 mmol) in anhydrous EtOAc (30 mL) was added HCl/EtOAc (50 mL) dropwise. After the mixture was stirred at r.t. for 5 h, it was filtered and the solid was dried to give compound 5 (16 g, 73.7%).

¹H NMR (400 MHz, DMSO-d₆): δ 8.02 (s, 2H), 6.99 (s, 2H), 3.37-3.34 (m, 2H), 2.71-2.64 (m, 2H), 1.56-1.43 (m, 4H), 1.23-1.20 (m, 2H).

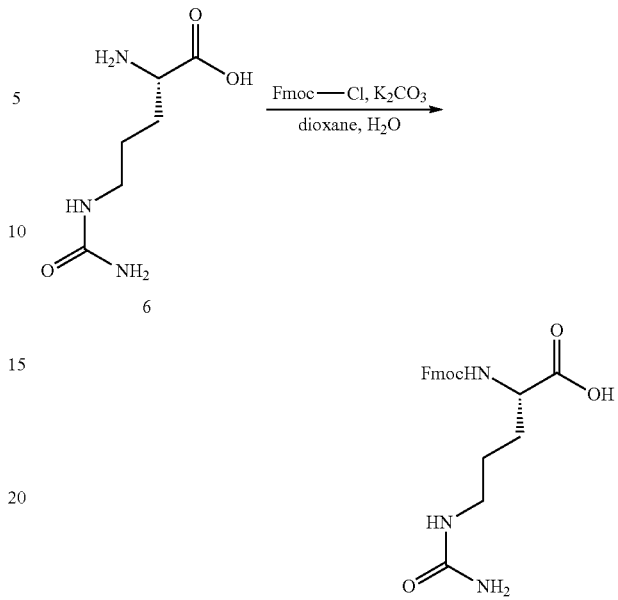

To a mixture of compound 6 (17.50 g, 0.10 mol) in a mixture of dioxane and H₂O (50 mL/75 mL) was added K₂CO₃ (34.55 g, 0.25 mol). Fmoc-Cl (30.96 g, 0.12 mol) was added slowly at 0° C. The reaction mixture was warmed to r.t. over 2 h. Organic solvent was removed under reduced pressure, and the water slurry was adjusted to pH=3 with 6 M HCl solution, and extracted with EtOAc (100 mL×3). The organic layer was dried over Na₂SO₄, filtered, and concentrated under reduced pressure to give the desired product 7 (38.0 g, 95.6%). (Compound 7 later became commercially available.)

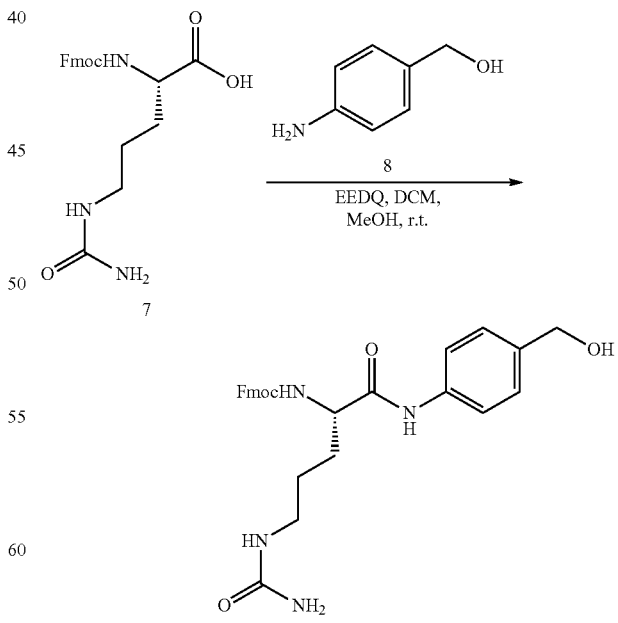

To a solution of compound 7 (4 g, 10 mmol) in a mixture of DCM and MeOH (100 mL/50 mL) was added 4-aminophenyl-methanol (8) (1.6 g, 13 mmol, 1.3 eq) and EEDQ (3.2 g, 13 mmol, 1.3 eq). After the mixture was stirred at r.t. for 16 h under N2, it was concentrated to give a brown solid. MTBE (200 mL) was added and it was stirred at 15° C. for 2 h. The solid was collected by filtration, washed with MTBE (50 mL×2) to give the crude product 9 as an orange solid (4.2 g, 84%). LCMS (ESI): m/z 503.0 [M+1].

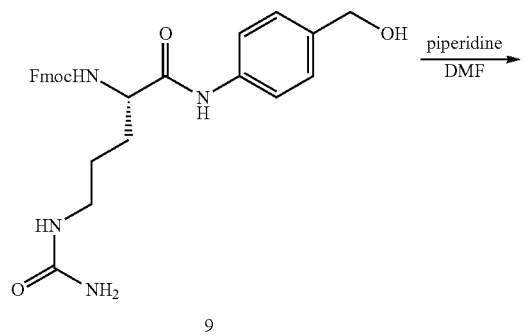

9

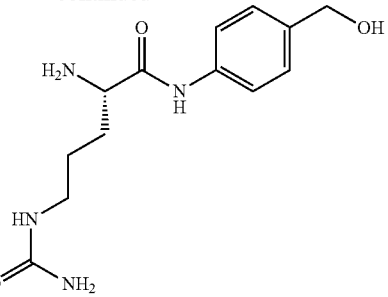

10

To a stirred solution of compound 9 (4.2 g, 8.3 mmol) in dry DMF (20 ml) was added piperidine (1.65 mL, 17 mmol, 2 eq) dropwise at r.t. The mixture was stirred at r.t. for 30 min, and solid precipitate formed. Dry DCM (50 mL) was added, and the mixture became transparent immediately. The mixture was stirred at r.t. for another 30 min, and LCMS showed compound 9 was consumed. It was concentrated to dryness under reduced pressure (make sure no piperidine remained), and the residue was partitioned between EtOAc and H$_2$O (50 mL/20 mL). The aqueous phase was washed with EtOAc (50 mL×2) and concentrated to give 10 as an oily residual (2.2 g, 94%) (contained small amount of DMF).

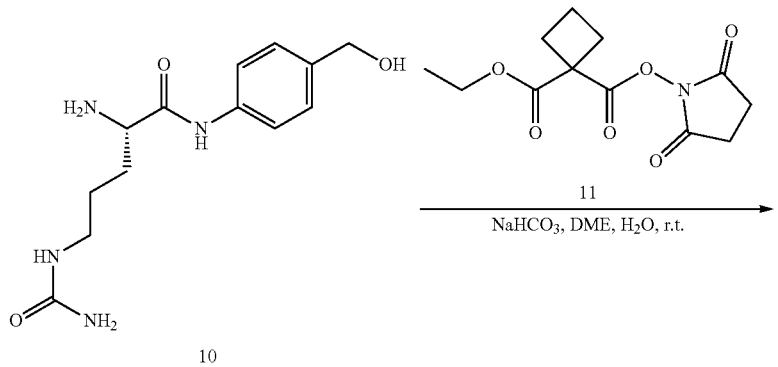

10

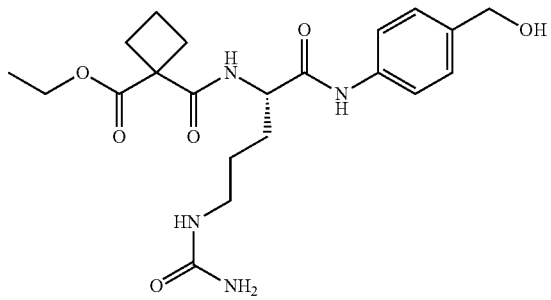

12

To a solution of compound 11 (8 g, 29.7 mmol) in DME (50 mL) was added a solution of compound 10 (6.0 g, 21.4 mmol) and NaHCO₃ (7.48 g, 89.0 mmol) in water (30 mL). After the mixture was stirred at r.t. for 16 h, it was concentrated to dryness under reduced pressure and the residue was purified by column chromatography (DCM:MeOH=10:1) to give crude compound 12 as white solid (6.4 g, 68.7%).

LCMS (ESI): m/z 435.0 [M+1].

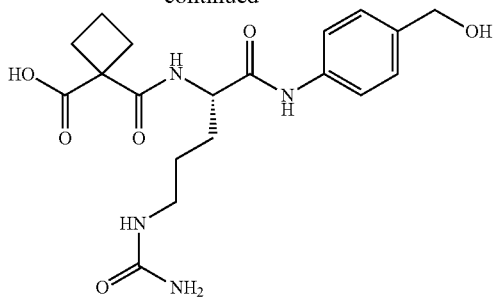

13

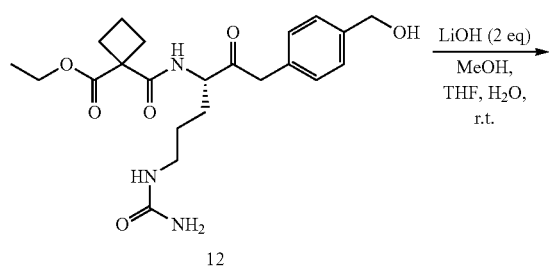

12

To a stirred solution of compound 12 (6.4 g, 14.7 mmol) in a mixture of THF and MeOH (20 mL/10 mL) was added a solution of LiOH.H₂O (1.2 g, 28.6 mmol) in H₂O (20 mL) at r.t. After the reaction mixture was stirred at r.t. for 16 h, solvent was removed under reduced pressure, and the residue obtained was purified by preparative HPLC to give compound 13 (3.5 g, yield: 58.5%).

LCMS (ESI): m/z 406.9 [M+1].

$^1$H NMR (400 MHz, Methanol-$d_4$) δ 8.86 (d, J=8.4 Hz, 2H), 8.51 (d, J=8.4 Hz, 2H), 5.88-5.85 (m, 1H), 5.78 (s, 2H), 4.54-4.49 (m, 3H), 4.38-4.32 (m, 1H), 3.86-3.75 (m, 1H), 3.84-3.80 (m, 2H), 3.28-3.21 (m, 1H), 3.30-3.24 (m, 1H), 3.00-2.80 (m, 1H), 2.37-2.28 (m, 2H).

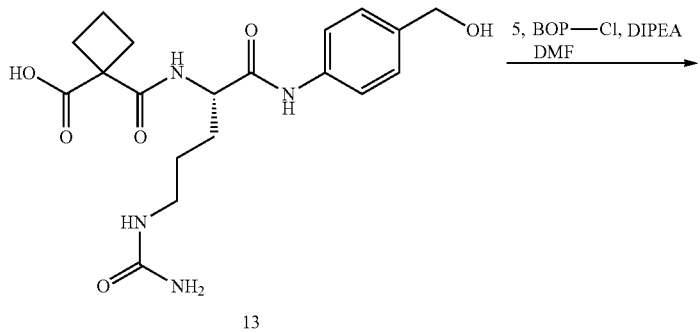

13

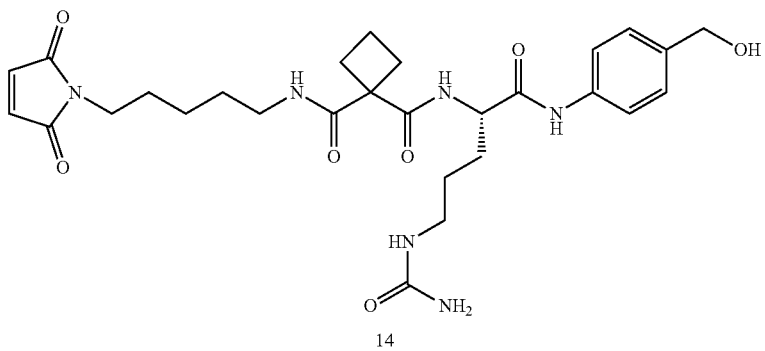

14

DIPEA (1.59 g, 12.3 mmol) and BOP-Cl (692 mg, 2.71 mmol) was added to a solution of compound 13 (1.0 g, 2.46 mmol) in DMF (10 mL) at 0° C., followed by compound 5 (592 mg, 2.71 mmol). The mixture was stirred at 0° C. for 0.5 h. The reaction mixture was quenched with a citric acid solution (10 mL), extracted with DCM/MeOH (10:1). The organic layer was dried and concentrated, and the residue was purified by column chromatography on silica gel (DCM:MeOH=10:1) to give compound 14 (1.0 g, 71%).

$^1$H NMR (400 MHz, DMSO-d$_6$): δ 10.00 (s, 1H), 7.82-7.77 (m, 2H), 7.53 (d, J=8.4 Hz, 2H), 7.19 (d, J=8.4 Hz, 2H), 6.96 (s, 2H), 5.95 (t, J=6.4 Hz, 1H), 5.39 (s, 2H), 5.08 (t, J=5.6 Hz, 1H), 4.40-4.35 (m, 3H), 4.09 (d, J=4.8 Hz, 1H), 3.01 (d, J=3.2 Hz, 2H), 3.05-2.72 (m, 4H), 2.68-2.58 (m, 3H), 2.40-2.36 (m, 4H), 1.72-1.70 (m, 3H), 1.44-1.42 (m, 1H), 1.40-1.23 (m, 6H), 1.21-1.16 (m, 4H).

Step 2: (S)—N-(1-(4-(chloromethyl)phenylamino)-1-oxo-5-ureidopentan-2-yl)-1-(6-(2,5-dioxo-2,5-dihydro-1H-pyrrol-1-yl)hexanamido)cyclobutanecarboxamide

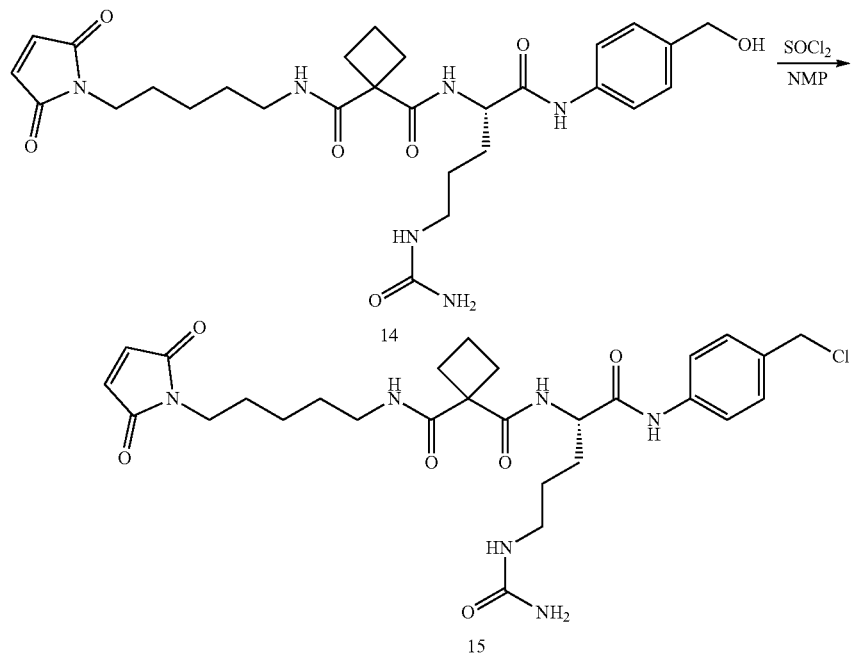

To a solution of compound 14 (2.0 g, 3.5 mmol) in NMP (50 mL) was added SOCl$_2$ (1.25 g, 10.5 mmol) dropwise at 0° C. After the reaction mixture was stirred at 20° C. for 30 min, it was diluted with water (50 mL) and extracted with EtOAc (50 mL×3). The organic layer was dried, concentrated and purified by flash column (DCM:MeOH=20:1) to give the product 15 (1.0 g, 48.4%) as a gray solid. LCMS: (5-95, AB, 1.5 min), 0.696 min, m/z=589.0 [M+1]$^+$.

Step 3: 2-[[2-[(1S)-1-(chloromethyl)-5-hydroxy-1,2-dihydrobenzo[e]indole-3-carbonyl]-1H-indol-5-yl]oxy]ethyl-[[4-[[(2S)-2-[[1-[5-(2,5-dioxopyrrol-1-yl)pentylcarbamoyl] cyclobutanecarbonyl]amino]-5-ureido-pentanoyl]amino]phenyl]methyl]-dimethyl-ammonium

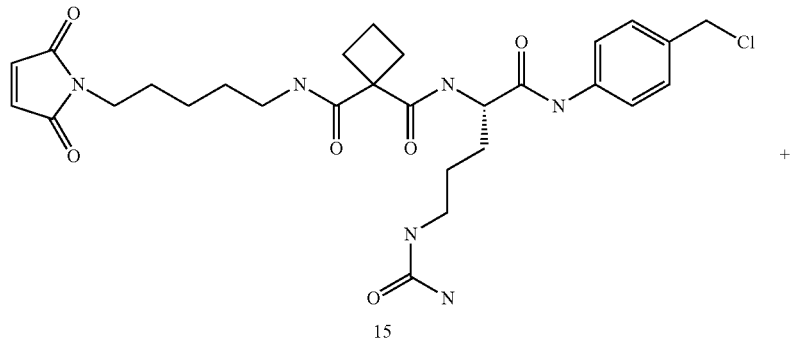

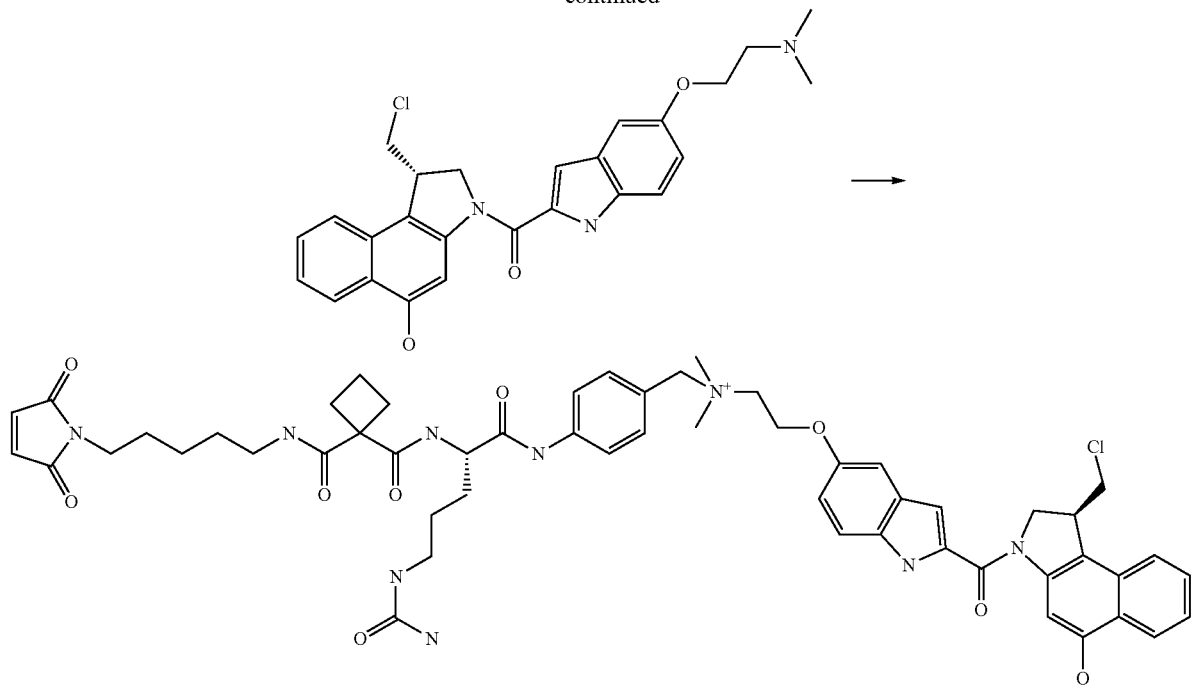

N1'-[(1S)-1-[[4-(chloromethyl)phenyl]carbamoyl]-4-ureido-butyl]-N1-[5-(2,5-dioxopyrrol-1-yl)pentyl]cyclobutane-1,1-dicarboxamide 15 (100 mass %, 1 equiv., 0.04310 mmol, 1.000, 25.39 mg) and [(1S)-1-(chloromethyl)-5-hydroxy-1,2-dihydrobenzo[e]indol-3-yl]-[5-(2-dimethylaminoethyloxy)-1H-indol-2-yl]methanone (100 mass %, 20 mg, 0.04310 mmol, 1.000, 20 mg) were combined in N,N-dimethylformamide (100 mass %) and the resulting mixture was allowed to stir for several days. Next tetrabutylammonium iodide (65.65 mass %, 0.3 equiv., 0.01293 mmol, 0.3000, 7.276 mg) was added and the mixture stirred overnight. No exchange of iodide with chloride was observed. Then, N,N-diisopropylethylamine (100 mass %, 1.2 equiv., 0.05172 mmol, 1.200, 6.685 mg, 0.00902 mL) was added and the mixture stirred for 4 hours. The reaction mixture contained a major peak on LCMS, which corresponded to desired product mass. The reaction mixture was then diluted with DMF, purified directly on HPLC under acidic conditions and pure fractions were isolated. Concentration of the fractions at RT degraded some material. As a result, the material was repurified. 2-[[2-[(1S)-1-(chloromethyl)-5-hydroxy-1,2-dihydrobenzo[e]indole-3-carbonyl]-1H-indol-5-yl]oxy]ethyl-[[4-[[(2S)-2-[[1-[5-(2,5-dioxopyrrol-1-yl)pentylcarbamoyl]cyclobutanecarbonyl]amino]-5-ureidopentanoyl]amino]phenyl]methyl]-dimethyl-ammonium (100 mass %, 11.8 mg, 0.0116 mmol, 0.269, 11.8 mg). 26.9% yield. M/Z=1017.35

Example 5 MC-Sq-Cit-PAB-Vinblastine (5S,7S,9S)-9-((3aR,3a1R,4R,5 S,5aR,10bR)-4-acetoxy-3a-ethyl-5-hydroxy-8-methoxy-5-(methoxycarbonyl)-6-methyl-3a,3a1,4,5,5a,6,11,12-octahydro-1H-indolizino[8,1-cd]carbazol-9-yl)-3-(4-((S)-2-(1-((5-(2,5-dioxo-2,5-dihydro-1H-pyrrol-1-yl)pentyl)carbamoyl)cyclobutanecarboxamido)-5-ureidopentanamido)benzyl)-5-ethyl-5-hydroxy-9-(methoxycarbonyl)-1,2,3,4,5,6,7,8,9,10-decahydro-3,7-methano[1]azacycloundecino[5,4-b]indol-3-ium

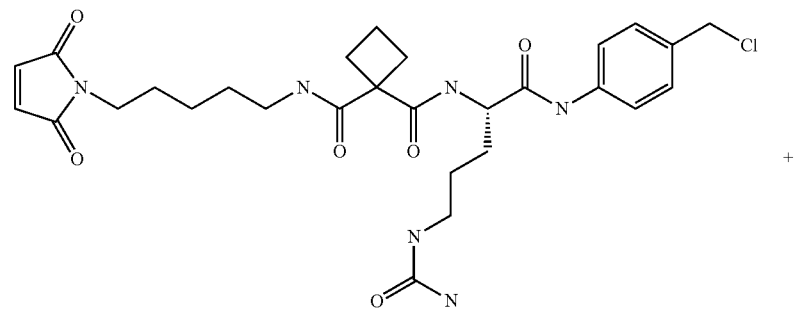

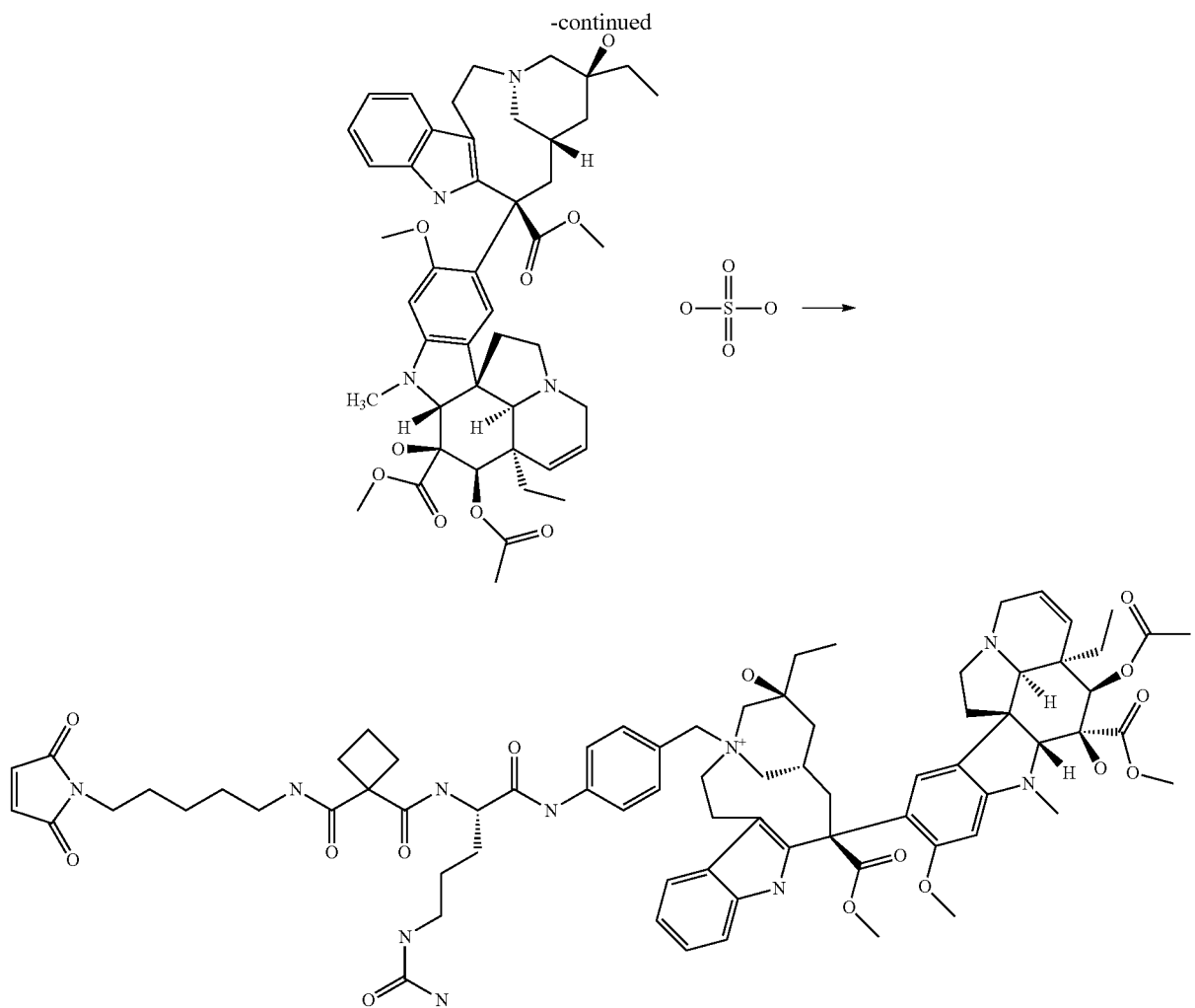

In a small vial was added N1'-[(1S)-1-[[4-(chloromethyl)phenyl]carbamoyl]-4-ureido-butyl]-N1-[5-(2,5-dioxopyrrol-1-yl)pentyl]cyclobutane-1,1-dicarboxamide (100 mass %, 1 equiv., 0.04400 mmol, 1.000, 25.92 mg) and vinblastine (89.21 mass %, B, 40 mg, 0.04400 mmol, 1.000, 40 mg) in N,N-dimethylformamide (100 mass %, 100 μL, 1.29 mmol, 29.4, 94.5 mg, 0.1 mL). To this mixture was added tetrabutylammonium iodide (65.65 mass %, 0.3 equiv., 0.01320 mmol, 0.3000, 7.428 mg) and N,N-diisopropylethylamine (100 mass %, 1 equiv., 0.04400 mmol, 1.000, 5.687 mg, 0.00767 mL) and the mixture was stirred for several days. One (1) extra equivalent of base was added to push reaction further.

The reaction mixture was diluted with DMF, purified directly on HPLC under acidic conditions. One pure fraction was isolated to give the final product (100 mass %, 8.1 mg, 0.0059 mmol, 0.13, 8.1 mg) M/Z=1364.85 (13% yield). Several impure fractions were also isolated.

1H NMR (500 MHz, DMSO-d6) δ 10.58 (s, 1H), 9.84 (s, 1H), 8.78 (s, 1H), 8.43 (s, 2H), 8.11 (d, J=7.9 Hz, 1H), 7.91 (t, J=5.6 Hz, 1H), 7.74 (d, J=8.1 Hz, 2H), 7.66 (d, J=8.1 Hz, 1H), 7.47 (d, J=8.1 Hz, 2H), 7.35 (d, J=8.0 Hz, 1H), 7.14-6.99 (m, 2H), 6.98 (d, J=2.4 Hz, 1H), 6.57 (s, 1H), 6.41 (s, 1H), 6.31 (t, J=6.6 Hz, 1H), 5.80 (dd, J=10.5, 4.9 Hz, 1H), 5.54 (s, 2H), 5.28 (d, J=10.1 Hz, 1H), 5.13 (s, 2H), 4.60 (d, J=12.4 Hz, 2H), 4.40 (dt, J=17.3, 6.1 Hz, 2H), 4.18-4.07 (m, 2H), 3.78 (s, 3H), 3.62 (t, J=14.1 Hz, 6H), 3.36 (t, J=7.0 Hz, 2H), 3.20 (dq, J=29.0, 8.5, 6.3 Hz, 2H), 3.07 (q, J=6.6 Hz, 2H), 2.98 (q, J=6.4 Hz, 2H), 2.93-2.86 (m, 1H), 2.83-2.71 (m, 2H), 2.67 (s, 3H), 2.48-2.33 (m, 5H), 2.30 (d, J=14.8 Hz, 1H), 2.12-2.04 (m, 1H), 1.97 (s, 3H), 1.70 (ddtd, J=44.3, 19.2, 9.5, 8.5, 4.4 Hz, 4H), 1.56-1.31 (m, 14H), 1.26-1.14 (m, 3H), 0.81 (t, J=7.4 Hz, 4H), 0.60 (t, J=7.3 Hz, 3H).

Examples 6 and 7

Example 6—MC-Sq-Cit-PAB-Morph-Linked-Gefitinib (S)-4-(3-(4-(3-chloro-4-fluorophenylamino)-7-methoxyquinazolin-6-yloxy)propyl)-4-(4-(2-(1-(5-(2,5-dioxo-2,5-dihydro-1H-pyrrol-1-yl)pentylcarbamoyl)cyclobutanecarboxamido)-5-ureidopentanamido)benzyl)morpholin-4-ium Example 7—MC-Sq-Cit-PAB-Primidine-Linked-Gefitinib (S)-4-(3-chloro-4-fluorophenylamino)-1-(4-(2-(1-(5-(2,5-dioxo-2,5-dihydro-1H-pyrrol-1-yl)pentylcarbamoyl)cyclobutanecarboxamido)-5-ureidopentanamido)benzyl)-7-methoxy-6-(3-morpholinopropoxy)quinazolin-1-ium

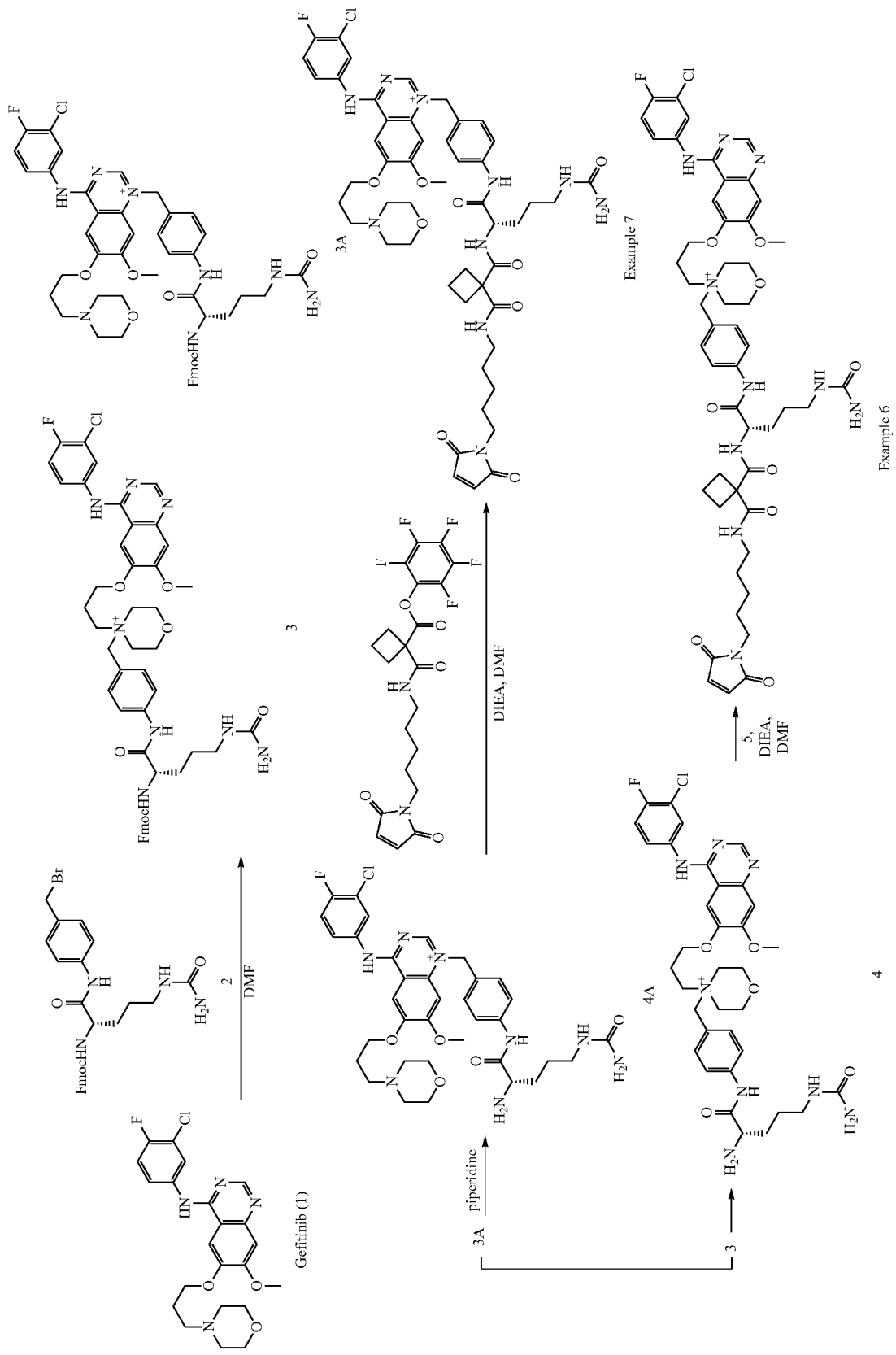
Scheme 1

Scheme 2. Synthesis of intermediates
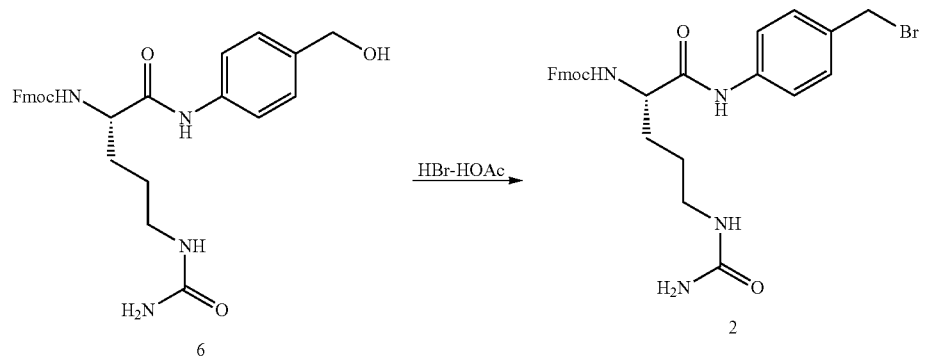
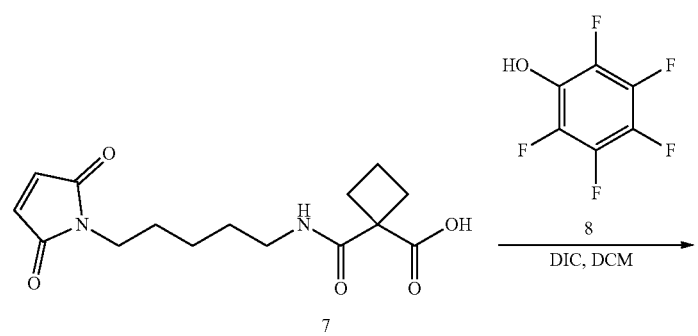
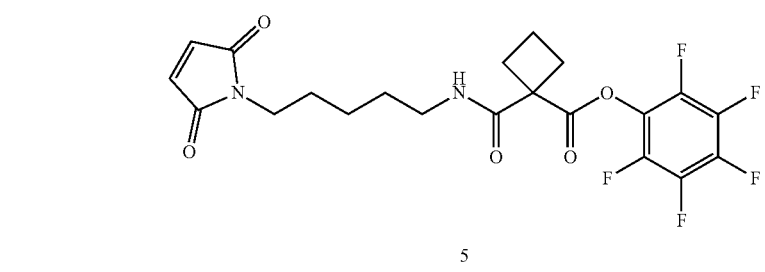
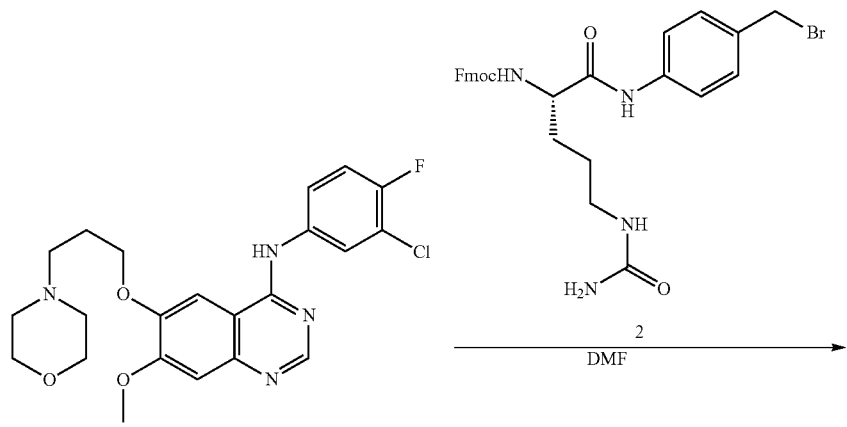

-continued

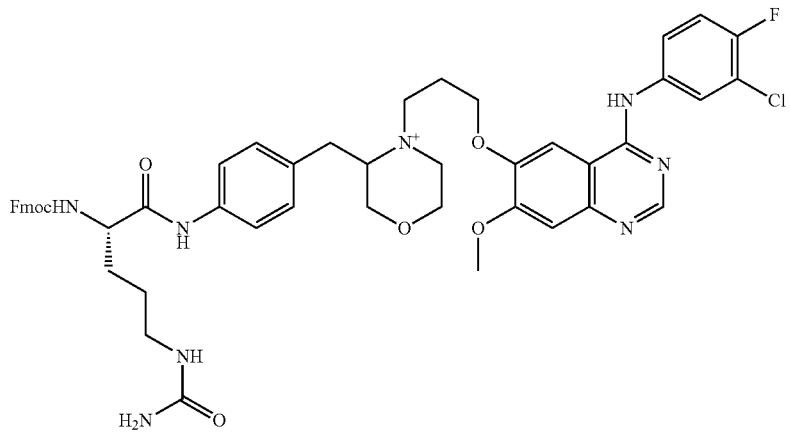

3

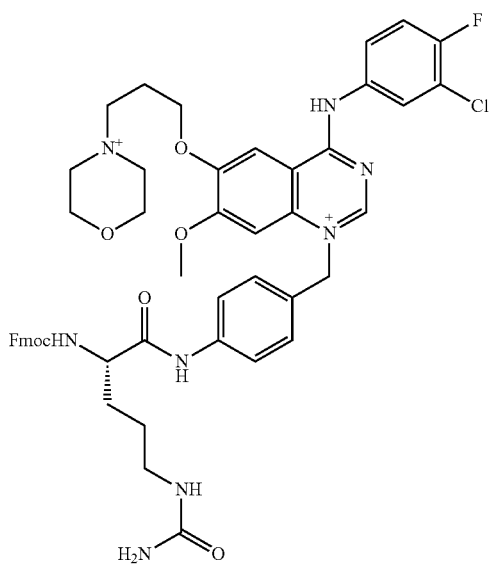

3A

A solution of compound 1 (113.88 mg, 0.20 mmol) and compound 2 (100 mg, 0.22 mmol) in DMF (3.0 mL) was stirred at 23° C. for 18.0 h. The reaction mixture was concentrated, and purified by silica gel chromatography (10 to 20% MeOH in DCM) to give compound 3A (9 mg, 4.3% yield) as yellow solid and compound 3 (8 mg, 3.5% yield) as white solid. $^1$HNMR for 3a: (400 MHz, DMSO-d6) δ 10.10 (s, 1H), 8.31 (s, 1H), 8.17 (s, 1H), 7.87-7.66 (d, J=8.8 Hz, 2H), 7.69-7.58 (m, 6H), 7.39-7.02 (m, 8H), 6.86 (s, 1H), 6.0 (s, 1H), 5.43 (s, 2H), 5.33 (s, 2H), 4.25-4.12 (m, 6H), 3.74 (s, 4H), 3.53-3.51 (m, 5H), 2.99-2.92 (m, 2H), 2.40-2.32 (m, 5H), 1.89-1.85 (m, 2H), 1.60-1.36 (m, 4H);

LCMS (5-95AB/1.5 min): $R_T$=0.673 min, [M+H]$^+$ 931.3.

$^1$HNMR for 3: (DMSO, 400 MHz) δ: 10.59 (s, 1H), 10.05 (s, 1H), 8.50 (s, 2H), 8.46 (s, 1H), 8.18-8.16 (d, J=8.0 Hz, 1H), 8.00 (s, 1H), 7.88-7.71 (m, 7H), 7.514-7.24 (m, 8H), 6.29 (s, 1H), 5.54 (s, 2H), 4.69 (s, 2H), 4.30-4.14 (m, 6H), 3.97-3.95 (m, 8H), 3.57-3.51 (m, 6H), 2.98-2.97 (d, J=5.6 Hz, 2H), 1.68-1.60 (m, 2H), 1.47-1.40 (m, 2H);

LCMS (5-95AB/1.5 min): $R_T$=0.662 min, [M+H]$^+$ 931.3.

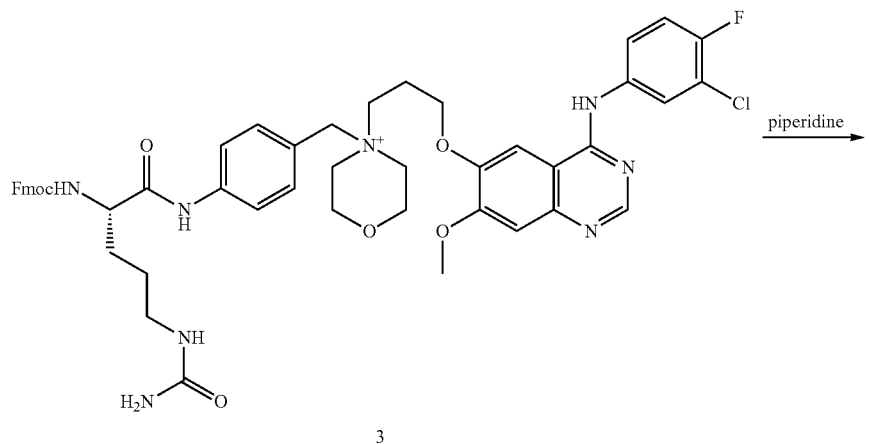
3
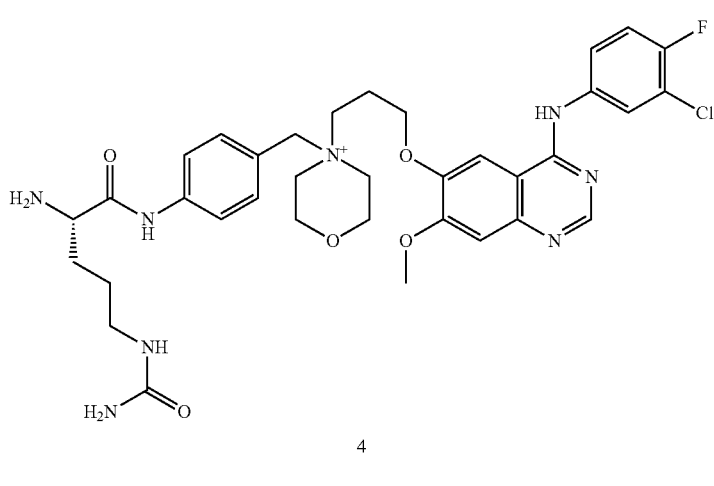
4
To a solution of compound 3 (50.0 mg, 0.050 mmol) in DMF (1.5 mL) was added piperidine (9.13 mg, 0.110 mmol), and the mixture was stirred at 23° C. for 3.0 h. LCMS showed 50.6% of product. The mixture was concentrated, and the residue was washed with MTBE (6.0 mL) two times to give compound 4 (31 mg, 0.044 mmol, 81.4%) as white solid which was used directly. LCMS (5-95AB/1.5 min): RT=0.553 min, [M+H]$^+$ 709.2
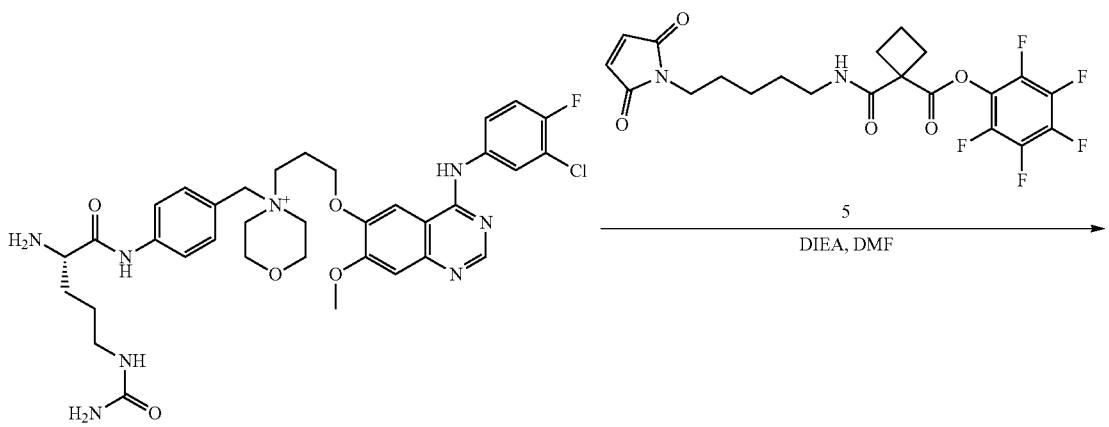
4

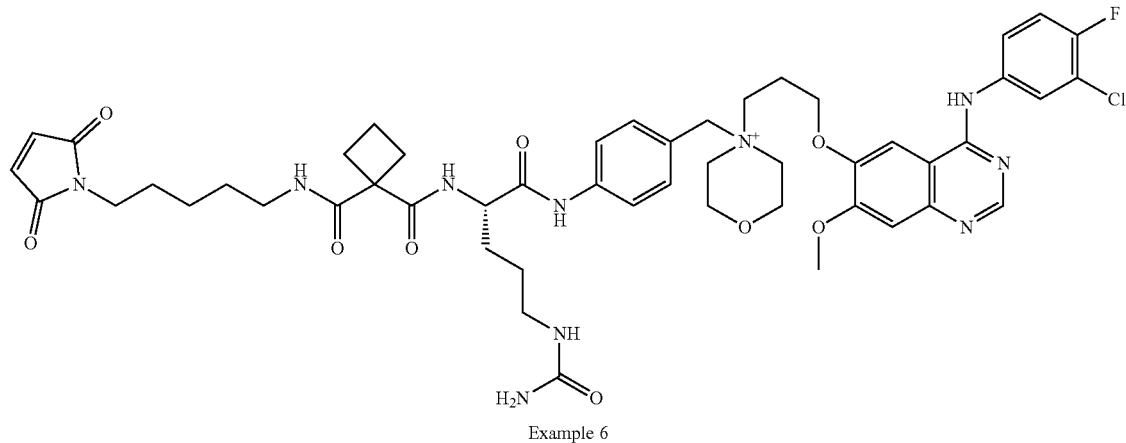

Example 6

To a solution of compound 4 (31.0 mg, 0.040 mmol) in DMF (3.0 mL) was added compound 5 (41.4 mg, 0.090 mmol) and DIEA (11.3 mg, 0.090 mmol). After the mixture was stirred at 23° C. for 18.0 h, LCMS showed 52% of product. The residue was purified by prep-HPLC (FA, acetonitrile 20%-50%) to give (S)-4-(3-(4-(3-chloro-4-fluorophenylamino)-7-methoxyquinazolin-6-yloxy)propyl)-4-(4-(2-(1-(5-(2,5-dioxo-2,5-dihydro-1H-pyrrol-1-yl)pentylcarbamoyl)cyclobutanecarboxamido)-5-ureidopentanamido)benzyl)morpholin-4-ium, Example 6 (10.4 mg, 23.6% yield) as a white solid. LCMS (5-95AB/1.5 min): RT=0.736 min, [M+H]⁺ 1001.1

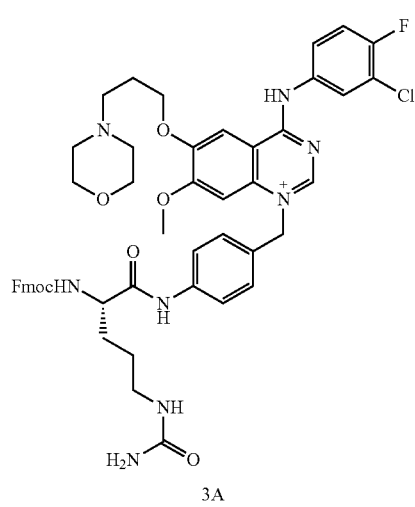

3A piperidine →

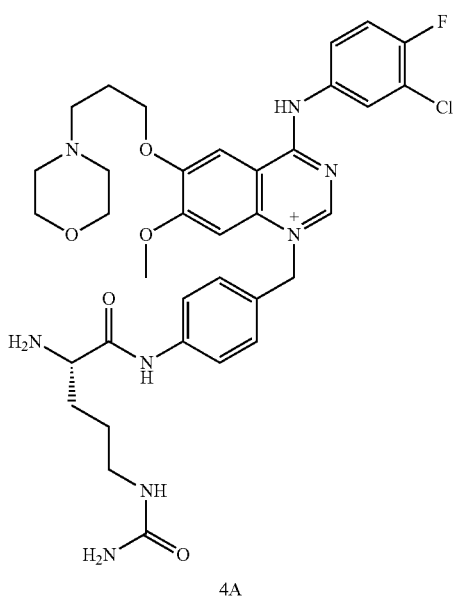

4A

To a solution of compound 3A (110.0 mg, 0.120 mmol) in DMF (2.5 mL) was added piperidine (20.1 mg, 0.240 mmol). The mixture was stirred at 23° C. for 3.0 h. LCMS showed 50.7% of product. The mixture was concentrated to remove DMF, washed with MTBE (10.0 mL) twice to give crude compound 4A (85 mg, 100% yield) as yellow solid, which was used directly in the next step.

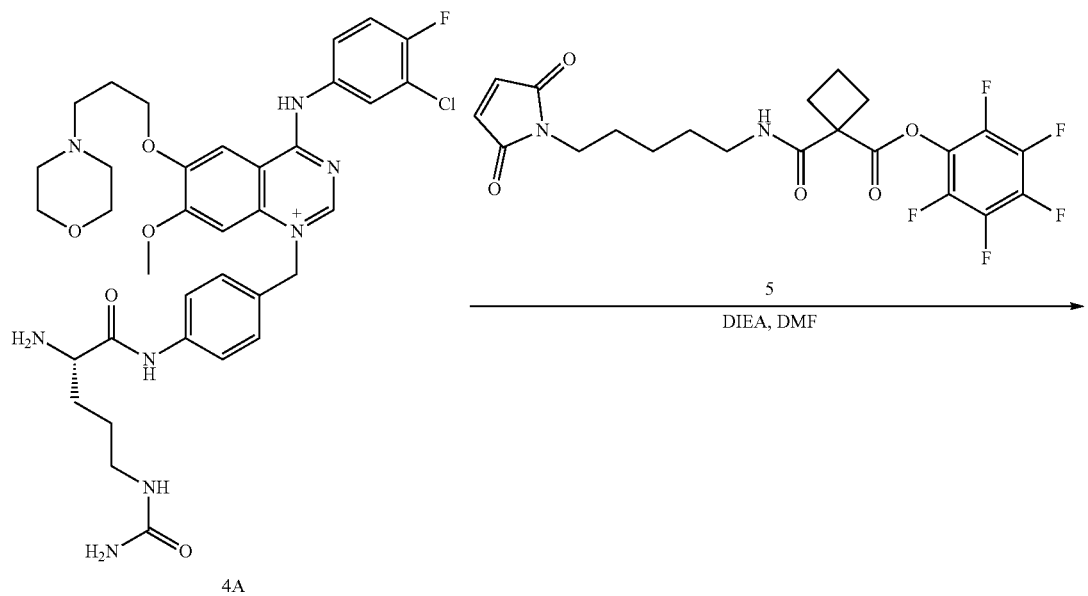

4A

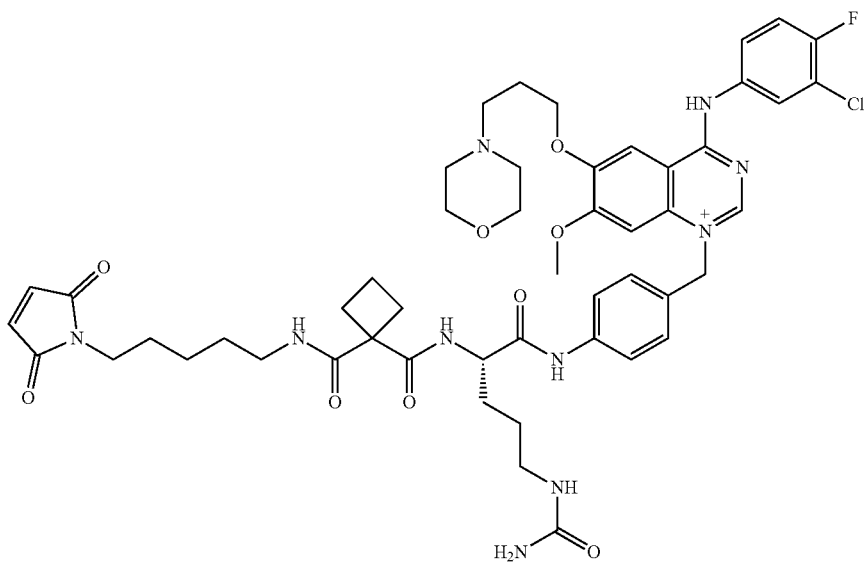

Example 7

To a solution of compound 4A (40 mg, 0.060 mmol) in DMF (3 mL) was added compound 5 (53.4 mg, 0.110 mmol), and DIEA (14.6 mg, 0.113 mmol). The mixture was stirred at 23° C. for 18.0 h. The resulting residue was purified by preparative HPLC (FA, acetonitrile 20%-50%) to give (S)-4-(3-chloro-4-fluorophenylamino)-1-(4-(2-(1-(5-(2,5-dioxo-2,5-dihydro-1H-pyrrol-1-yl)pentylcarbamoyl)cyclobutanecarboxamido)-5-ureidopentanamido)benzyl)-7-methoxy-6-(3-morpholinopropoxy)quinazolin-1-ium, Example 7 (10.3 mg, 17.9% yield) as yellow solid. LCMS (5-95AB/1.5 min): RT=0.740 min, [M]⁺ 1001.6.

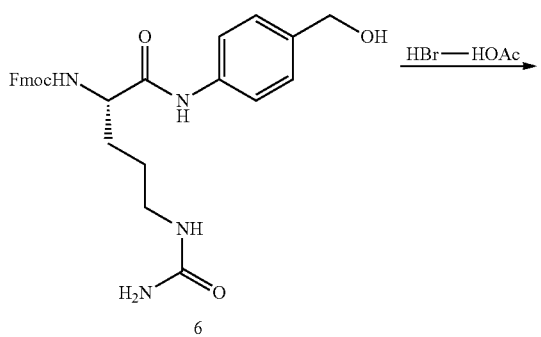

6

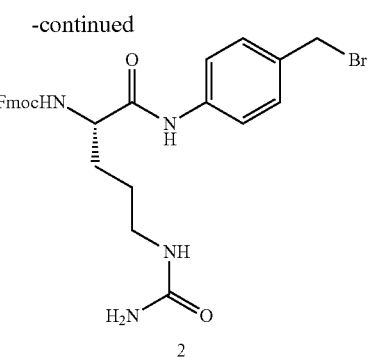

To a flask filled with compound 6 (1000 mg, 1.99 mmol) added the solution of HBr/HOAc (4.0 mL) dropwise at 0° C. It was stirred at 25° C. for 3.0 h. LCMS (5-95AB/1.5 min) showed 90.2% of product. The mixture was concentrated, EtOAc (300 mL) was added and concentrated to remove the small amount of acid, then the residue was poured into ice-water (50.0 mL) and the solid was collected by filtration to give compound 2 (726 mg, 41.3% yield) as gray solid. LCMS (5-95AB/1.5 min): RT=0.772 min, [M+H]$^+$ 567.0.

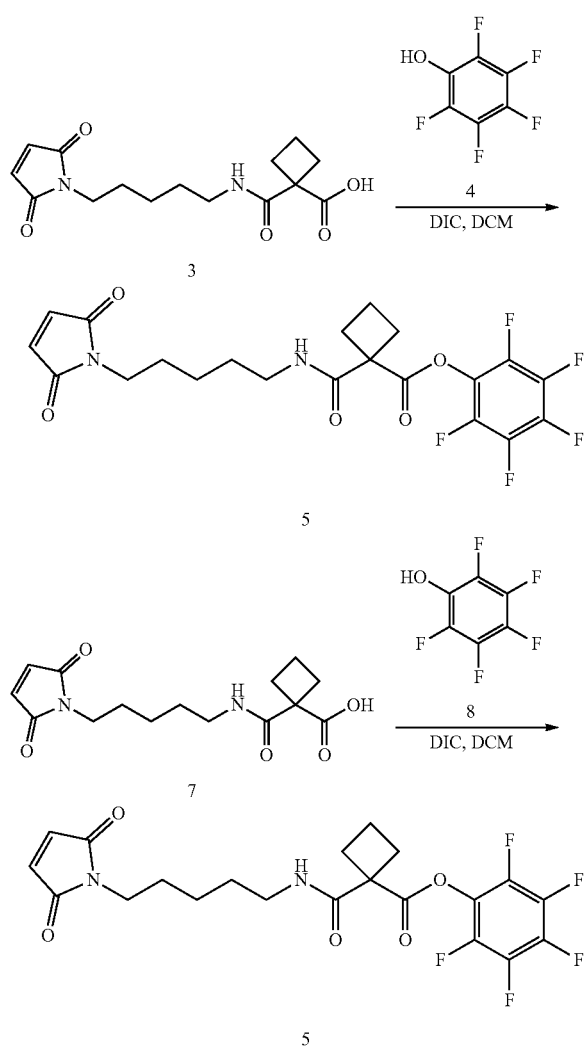

To a solution of compound 7 (200 mg, 0.65 mmol) in DCM (12 mL) was added compound 7 (179 mg, 0.97 mmol) and DIC (123 mg, 0.97 mmol), the mixture was stirred at 23° C. for 1.5 h. LCMS showed 70.9% of product. The mixture was concentrated, and washed with THF (2.0 mL) twice to give compound 5 (120 mg, 0.263 mmol, 40.5% yield) as colorless oil which was used directly in the next step.

Method of Preparing ADCs

Preparation of Cysteine Engineered Antibodies for Conjugation by Reduction and Reoxidation Under certain conditions, the cysteine engineered antibodies may be made reactive for conjugation with linker-drug intermediates of the invention, by treatment with a reducing agent such as DTT (Cleland's reagent, dithiothreitol) or TCEP (tris(2-carboxyethyl)phosphine hydrochloride; Getz et al (1999) Anal. Biochem. Vol 273:73-80; Soltec Ventures, Beverly, Mass.). Full length, cysteine engineered monoclonal antibodies (ThioMabs) expressed in CHO cells (Gomez et al (2010) Biotechnology and Bioeng. 105(4): 748-760; Gomez et al (2010) Biotechnol. Prog. 26:1438-1445) were reduced, for example with about a 50 fold excess of DTT overnight at room temperature to reduce disulfide bonds which may form between the newly introduced cysteine residues and the cysteine present in the culture media.

Light chain amino acids are numbered according to Kabat (Kabat et al., *Sequences of proteins of immunological interest*, (1991) 5th Ed., US Dept of Health and Human Service, National Institutes of Health, Bethesda, Md.). Heavy chain amino acids are numbered according to the EU numbering system (Edelman et al (1969) Proc. Natl. Acad. of Sci. 63(1):78-85), except where noted as the Kabat system. Single letter amino acid abbreviations are used.

Full length, cysteine engineered monoclonal antibodies (ThioMabs) expressed in CHO cells bear cysteine adducts (cystines) or glutathionylated on the engineered cysteines due to cell culture conditions. To liberate the reactive thiol groups of the engineered cysteines, the ThioMabs are dissolved in 500 mM sodium borate and 500 mM sodium chloride at about pH 8.0 and reduced with about a 50-100 fold excess of 1 mM TCEP (tris(2-carboxyethyl)phosphine hydrochloride (Getz et al (1999) Anal. Biochem. Vol 273: 73-80; Soltec Ventures, Beverly, Mass.) for about 1-2 hrs at 37° C. Alternatively, DTT can be used as reducing agent. The formation of inter-chain disulfide bonds was monitored either by non-reducing SDS-PAGE or by denaturing reverse phase HPLC PLRP column chromatography. The reduced ThioMab is diluted and loaded onto a HiTrap SP FF column in 10 mM sodium acetate, pH 5, and eluted with PBS containing 0.3M sodium chloride, or 50 mM Tris-Cl, pH 7.5 containing 150 mM sodium chloride.

Disulfide bonds were reestablished between cysteine residues present in the parent Mab by carrying out reoxidation. The eluted reduced ThioMab is treated with 15× or 2 mM dehydroascorbic acid (dhAA) at pH 7 for 3 hours or for 3 hrs in 50 mM Tris-Cl, pH 7.5, or with 2 mM aqueous copper sulfate (CuSO$_4$) at room temperature overnight. Other oxidants, i.e. oxidizing agents, and oxidizing conditions, which are known in the art may be used. Ambient air oxidation may also be effective. This mild, partial reoxidation step forms intrachain disulfides efficiently with high fidelity. The buffer is exchanged by elution over Sephadex G25 resin and eluted with PBS with 1 mM DTPA. The thiol/Ab value is checked by determining the reduced antibody concentration from the absorbance at 280 nm of the solution and the thiol concentration by reaction with DTNB (Aldrich, Milwaukee, Wis.) and determination of the absorbance at 412 nm.

Liquid chromatography/Mass Spectrometric Analysis was performed on a TSQ Quantum Triple Quadrupole™ mass spectrometer with extended mass range (Thermo Electron, San Jose Calif.). Samples were chromatographed on a PRLP-S®, 1000 A, microbore column (50 mm×2.1 mm, Polymer Laboratories, Shropshire, UK) heated to 75° C. A linear gradient from 30-40% B (solvent A: 0.05% TFA in water, solvent B: 0.04% TFA in acetonitrile) was used and the eluent was directly ionized using the electrospray source. Data were collected by the Xcalibur® data system and deconvolution was performed using ProMass® (Novatia, LLC, New Jersey). Prior to LC/MS analysis, antibodies or drug conjugates (50 micrograms) were treated with PNGase F (2 units/ml; PROzyme, San Leandro, Calif.) for 2 hours at 37° C. to remove N-linked carbohydrates.

Hydrophobic Interaction Chromatography (HIC) samples were injected onto a Butyl HIC NPR column (2.5 micron particle size, 4.6 mm×3.5 cm) (Tosoh Bioscience) and eluted with a linear gradient from 0 to 70% B at 0.8 ml/min (A: 1.5 M ammonium sulfate in 50 mM potassium phosphate, pH 7, B: 50 mM potassium phosphate pH 7, 20% isopropanol). An Agilent 1100 series HPLC system equipped with a multi wavelength detector and Chemstation software was used to resolve and quantitate antibody species with different ratios of drugs per antibody. Cysteine engineered antibodies of the present invention can be prepared according the general method described above.

Conjugation of Linker-Drug Intermediates to Antibodies (Procedure 1)

Engineered antibody cysteines were blocked as mixed disulfides with glutathione and/or cysteine as expressed in CHO cells. These cysteines had to be "deblocked" prior to conjugation.

Deblocked antibody (5-12 mg/mL) in 20 mM succinate, 150 mM NaCl, 2 mM EDTA was brought to 75-100 mM Tris, pH 7.5-8 (using 1M Tris). Co-solvent (DMSO, DMF, or DMA) was added to the antibody solution, followed by linker-drug (in DMSO or DMF) to give a final %-organic solvent of 10-13% and final concentration of linker-drug 2.5-10× relative to antibody concentration. Reactions were allowed to proceed at room temperature for 1-12 hours (until maximum conjugation was achieved). Conjugation reactions were purified via cation exchange chromatography and/or gel filtration using disposable columns (S maxi or Zeba, respectively). Additional purification by preparative gel filtration (S200 columns) was performed if the crude conjugate was significantly aggregated according to analytical SEC (e.g., >10%). Conjugates were subsequently exchanged into formulation buffer (20 mM His-acetate, pH 5.5, 240 mM sucrose) using either gel filtration or dialysis. Tween-20 was subsequently added to the purified conjugate to reach a final concentration of 0.02%. Final conjugate concentrations ranged from 2.4 to 7.5 mg/mL (% Yield: 34-81% from deblocked antibody). Conjugates were analyzed by LCMS to obtain a measurement of the drug-antibody ratio (DAR), which ranged from 1.3 to 2.1 (average: 1.8). Conjugates were also analyzed for presence of high-molecular weight aggregates using analytical SEC (Zenix or Shodex columns); final, purified conjugates displayed aggregation ranging from 0-10%. Conjugates were also assessed for endotoxin contamination, which, in all cases, did not exceed 1.3 EU/mg. Free, unconjugated drug did not exceed 1% of the final conjugate.

Conjugation of Linker-Drug Intermediates to Antibodies (Procedure 2, Alternative Procedure)

After the reduction and reoxidation procedures of the above example, the antibody is dissolved in PBS (phosphate buffered saline) buffer and chilled on ice. An excess, from about 1.5 molar to 20 equivalents of a linker-drug intermediate with a thiol-reactive functional group such as maleimido or bromo-acetamide, is dissolved in DMSO, diluted in acetonitrile and water, and added to the chilled reduced, reoxidized antibody in PBS. After about one hour, an excess of maleimide is added to quench the reaction and cap any unreacted antibody thiol groups. The conjugation mixture may be loaded and eluted through a HiTrap SP FF column to remove excess drug-linker intermediate and other impurities. The reaction mixture is concentrated by centrifugal ultrafiltration and the cysteine engineered antibody drug conjugate is purified and desalted by elution through G25 resin in PBS, filtered through 0.2 μm filters under sterile conditions, and frozen for storage.

The ADCs of the present invention can be prepared according to the procedure described in the above section.

Assays

Select linkers were then tested and found active in in vitro and in vivo assays. The cleavage data is shown in the table below Cathepsin B Cleavage Assay Like peptide linkers, non-peptide linkers for ADCs are expected to be cleavable in a lysosome for proper drug release. As a digestive organelle of the cell, the lysosome is enriched with some proteases which show optimal hydrolytic activity at an acidic pH. Cathepsin B is a representative lysosomal protease and has been shown to contribute to the activation of ADC peptide linkers. As an initial screen, an assay was developed using purified cathepsin B to identify cleavable linker-drug constructs that are suitable for conjugation with antibody. Norfloxacin was used to represent the drug component of the linker-drug. The percentage of cleavage relative to the control peptides (such as Val-Cit) was measured at a given time point as well as the kinetic parameters of the cleavage reaction (Km and Vmax). A detailed description of the assay is shown below. From this assay, a variety of proteolytically active and structurally diverse linkers can be identified and later used in making ADCs.

Cathepsin B cleavage activity using experimental linker-drugs as substrate was measured by monitoring the release of Norfloxacin using LC/MS. Varying concentrations of linker-drug (3-fold serial dilutions) were incubated in 20 uL reactions containing 20 nM Cathepsin B (EMD Millipore cat. #219364, human liver), 10 mM MES pH 6.0, 1 mM DTT, 0.03% CHAPS, and 25 nM Norfloxacin-d5 internal standard (Santa Cruz Biotechnology, cat. #sc-301482). Reactions were incubated for 1 hour at 37° C., followed by addition of 60 uL of 2% formic acid to quench the reactions. Samples were analyzed by injecting 2 uL of stopped reactions on a Waters Acquity UPLC BEH Phenyl column (2.1 mm×50 mm, Waters cat. #186002884). Samples were purified using a linear 2 minute gradient (0% to 80%) of acetonitrile, 0.1% formic acid on a Water Acquity UPLC. Norfloxacin and Norfloxacin-d5 internal standard were detected using an AB Sciex QTrap 5500 triple quadrupole mass spectrometer operating in positive MRM mode (Norfloxacin 320→233 m/z, Norfloxacin-d5 325→233 m/z). The quantified norfloxacin (normalized with internal standard) was plotted against linker-drug concentration, and the resulting plot was curve fitted with a Michaelis-Menten fit using GraphPad Prism software for the kinetic constants Km and Vmax.

In Vitro Cell Proliferation Assay

Efficacy of an ADC was measured by a cell proliferation assay employing the following protocol (CELLTITER GLO™ Luminescent Cell Viability Assay, Promega Corp. Technical Bulletin TB288; Mendoza et al (2002) Cancer Res. 62:5485-5488):

1. An aliquot of 100 μl of cell culture containing about $10^4$ cells (SKBR-3, BT474, MCF7 or MDA-MB-468) in medium was deposited in each well of a 96-well, opaque-walled plate.

2. Control wells were prepared containing medium and without cells.

3. ADC was added to the experimental wells and incubated for 3-5 days.

4. The plates were equilibrated to room temperature for approximately 30 minutes.

5. A volume of CELLTITER GLO™ Reagent equal to the volume of cell culture medium present in each well was added.

6. The contents were mixed for 2 minutes on an orbital shaker to induce cell lysis.

7. The plate was incubated at room temperature for 10 minutes to stabilize the luminescence signal.

8. Luminescence was recorded and reported in graphs as RLU=relative luminescence units.

Data are plotted as the mean of luminescence for each set of replicates, with standard deviation error bars. The protocol is a modification of the CELLTITER GLO™ Luminescent Cell Media: SK-BR-3 grow in 50/50/10% FBS/glutamine/250 μg/mL G-418 OVCAR-3 grow in RPMI/20% FBS/glutamine In Vivo Assay 1. The efficacy of the anti-Napi2B antibody-drug conjugates (ADCs) was investigated in a mouse xenograft model of Igrov-1 (human ovarian cancer).

Female C.B-17 SCID-beige mice (Charles River Laboratories; San Diego, Calif.) were each inoculated in the thoracic mammary fat pad area with 5 million Igrov-1 cells. When the xenograft tumors reached an average tumor volume of 100-300 mm3 (referred to as Day 0), animals were randomized into groups of 7-10 mice each and received a single intravenous injection of the ADCs. Tumors and body weights of mice were measured 1-2 times a week throughout the study. Mice were promptly euthanized when body weight loss was >20% of their starting weight. All animals were euthanized before tumors reached 3000 mm3 or showed signs of impending ulceration.

2. The efficacy of the anti-Napi2B antibody-drug conjugates (ADCs) was investigated in a mouse xenograft model of OVCAR3-X2.1 (human ovarian cancer). The OVCAR3 cell line was obtained from ATCC (American Type Culture Collection; Manassas, Va.) and a sub-line OVCAR3-X2.1 was generated at Genentech for optimal growth in mice.

Female C.B-17 SCID-beige mice (Charles River Laboratories; San Diego, Calif.) were each inoculated in the thoracic mammary fat pad area with ten million OVCAR3-X2.1 cells. When the xenograft tumors reached an average tumor volume of 100-300 mm3 (referred to as Day 0), animals were randomized into groups of 7-10 mice each and received a single intravenous injection of the ADCs. Tumors and body weights of mice were measured 1-2 times a week throughout the study. Mice were promptly euthanized when body weight loss was >20% of their starting weight. All animals were euthanized before tumors reached 3000 mm3 or showed signs of impending ulceration.

3. The efficacy of the anti-CD22 antibody-drug conjugates (ADCs) is investigated in a mouse xenograft model of BJAB-luc (human Burkitt's lymphoma) or WSU-DLCL2 (human diffuse large B-cell lymphoma). The BJAB cell line is obtained from DSMZ (German Collection of Microorganisms and Cell Cultures; Braunschweig, Germany), and a sub-line BJAB-luc is generated at Genentech to stably express the luciferase gene. The WSU-DLCL2 cell line is also originated from DSMZ.

Female C.B-17 SCID mice (Charles River Laboratories; Hollister, Calif.) are each inoculated subcutaneously in the flank area with 20 million cells of BJAB-luc or WSU-DLCL2. When the xenograft tumors reached an average tumor volume of 100-300 mm3 (referred to as Day 0), animals are randomized into groups of 7-10 mice each and received a single intravenous injection of the ADCs. Tumors and body weights of mice are measured 1-2 times a week throughout the study. Mice are promptly euthanized when body weight loss is >20% of their starting weight. All animals are euthanized before tumors reached 3000 mm3 or showed signs of impending ulceration.

4. The efficacy of the anti-CD22 antibody-drug conjugates (ADCs) was investigated in a mouse xenograft model of WSU-DLCL2 (human diffuse large B-cell lymphoma). The WSU-DLCL2 cell line was obtained from DSMZ (German Collection of Microorganisms and Cell Cultures; Braunschweig, Germany).

Female C.B-17 SCID mice (Charles River Laboratories; Hollister, Calif.) were each inoculated subcutaneously in the flank area with 20 million WSU-DLCL2 cells. When the xenograft tumors reached an average tumor volume of 100-300 mm3 (referred to as Day 0), animals were randomized into groups of 7-10 mice each and received a single intravenous injection of the ADCs. Tumors and body weights of mice were measured 1-2 times a week throughout the study.

Mice were promptly euthanized when body weight loss was >20% of their starting weight. All animals were euthanized before tumors reached 3000 mm3 or showed signs of impending ulceration.

BIOLOGICAL DATA
ADC Linker-Drug structures

| Example | 1 |
|---|---|
| Corresponding ADC | Anti-Napi2b 10H1.11.4B LC K149C MC-Sq-Cit-PAB Dolastatin 10 (ADC1-1, DAR 1.9) and Anti-CD22 10F4v3 LC K149C MC-Sq-Cit-PAB Dolastatin 10 (ADC1-2, DAR 1.9) |
| Structure | 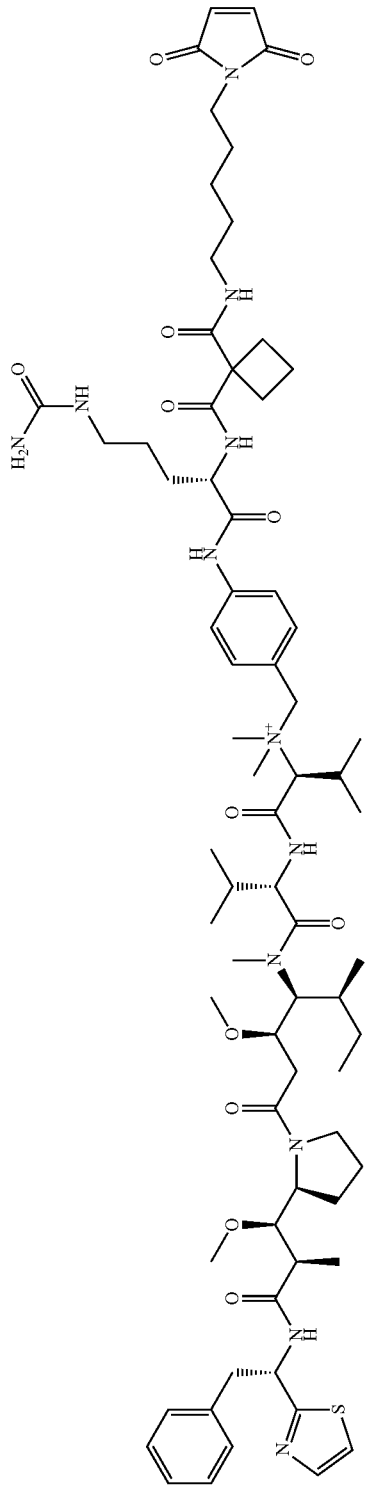 |
| Name | (S)-N-(4-((S)-2-(1-(5-(2,5-dioxo-2,5-dihydro-1H-pyrrol-1-yl)pentylcarbamoyl)cyclobutanecarboxamido)-5-ureidopentanamido)benzyl)-1-(((S)-1-(((3R,4S,5S)-3-methoxy-1-((S)-2-((1R,2R)-1-methoxy-2-methyl-3-oxo-3-((S)-2-phenyl-1-(thiazol-2-yl)ethylamino)propyl)pyrrolidin-1-yl)-5-methyl-1-oxoheptan-4-yl)(methyl)amino)-3-methyl-1-oxobutan-2-ylamino)-N,N,3-trimethyl-1-oxobutan-2-aminium |

-continued

| | BIOLOGICAL DATA ADC Linker-Drug structures |
|---|---|
| Example | 2 |
| Corresponding ADC | Anti-CD22 10F4v3 LC K149C MC-Sq-Cit-PAB-Tubulysin M (ADC2-2, DAR 1.8) and Anti-Napi2b 10H1.11.4B LC K149C MC-Sq-Cit-PAB-Tubulysin M (ADC2-1, DAR 1.8) |
| Structure | 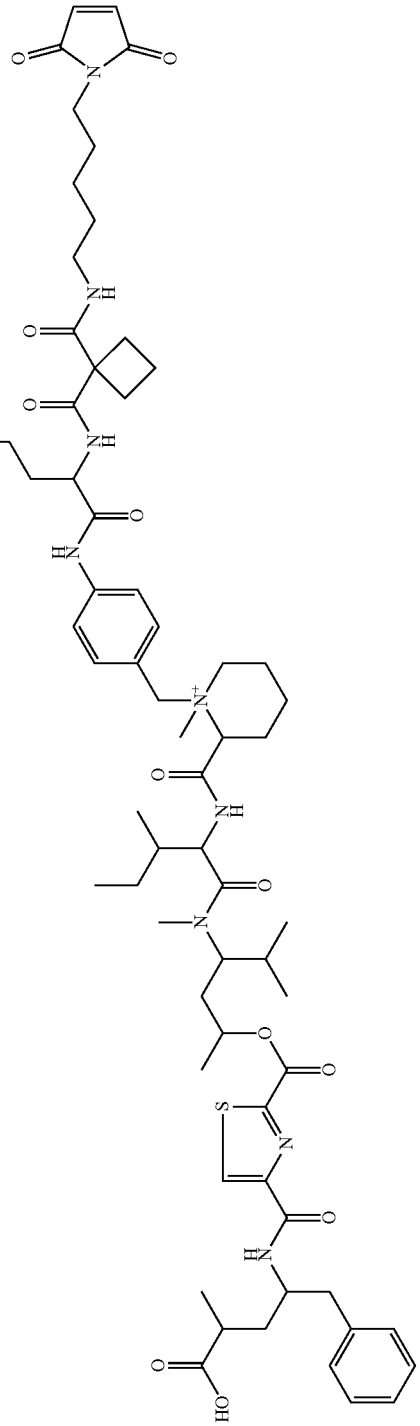 |
| Name | 2-(1-((1-acetoxy-1-(4-(4-carboxy-1-phenylpentan-2-ylcarbamoyl)thiazol-2-yl)-4-methylpentan-3-yl)(methyl)amino)-3-methyl-1-oxopentan-2-ylcarbamoyl)-1-(4-(2-(1-(5-(2,5-dioxo-2,5-dihydro-1H-pyrrol-1-yl)pentylcarbamoyl)cyclobutanecarboxamido)-5-ureidopentanamido)benzyl)-1-methylpiperidinium |

| | -continued |
|---|---|
| | BIOLOGICAL DATA<br>ADC Linker-Drug structures |

| Example | 3 |
|---|---|
| Corresponding ADC | Anti-CD22 10F4v3 LC K149C difulfide tubulysin M (DAR 2.0) and Anti-NaPi2b 10H1.11.4B LC K149C disulfide tubulysin M (DAR 2.0) |
| Structure | |
| Name | (2S,4R)-4-[[2-[(1R,3R)-1-acetoxy-4-methyl-3-[methyl-[(2S,3S)-3-methyl-2-[[(2R)-1-methyl-1[[4-[[(2R)-2-[(6-nitro-3-pyridyl)disulfanyl]propoxy]carbonylamino]phenyl]methyl]piperidin-1-ium-2-carbonyl]amino]pentanoyl]amino]pentyl]thiazole-4-carbonyl]amino]-2-methyl-5-phenyl-pentanoic acid<br>(Nitro-MM-PDS-PAB-Tubulysin M) |

| Example | 4 |
|---|---|
| Structure | |
| Name | 2-[[2-[((1S)-1-(chloromethyl)-5-hydroxy-1,2-dihydrobenzo[e]indole-3-carbonyl]-1H-indol-5-yl]oxy]ethyl-[[4-[[(2S)-2-[[1-[5-(2,5-dioxopyrrol-1-yl)pentyl]carbamoyl]cyclobutanecarbonyl]amino]-5-ureido-pentanoyl]amino]phenyl]methyl]-dimethyl-ammonium<br>(MC-Sq-Cit-PAB-DuocarmycinDM) |

-continued
BIOLOGICAL DATA
ADC Linker-Drug structures
| Example | 5 |
|---|---|
| Structure | 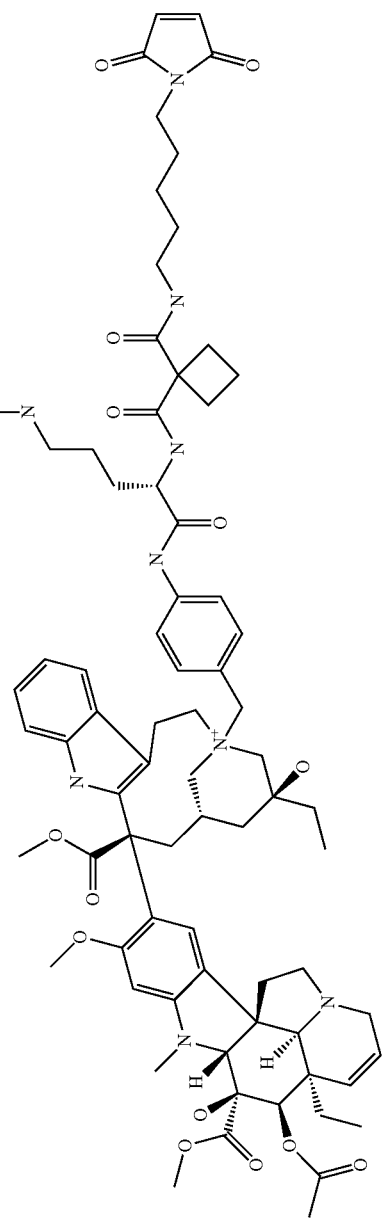 |
| Name | (S)-4-(3-(4-(3-chloro-4-fluorophenylamino)-7-methoxyquinazolin-6-yloxy)propyl)-4-(4-(2-(1-(5-(2,5-dioxo-2,5-dihydro-1H-pyrrol-1-yl)pentylcarbamoyl)cyclobutanecarboxamido)-5-ureidopentanamido)benzyl)morpholin-4-ium MC-Sq-Cit-PAB-morph-linked-gefitinib |
| Example | 6 |
|---|---|
| Structure | 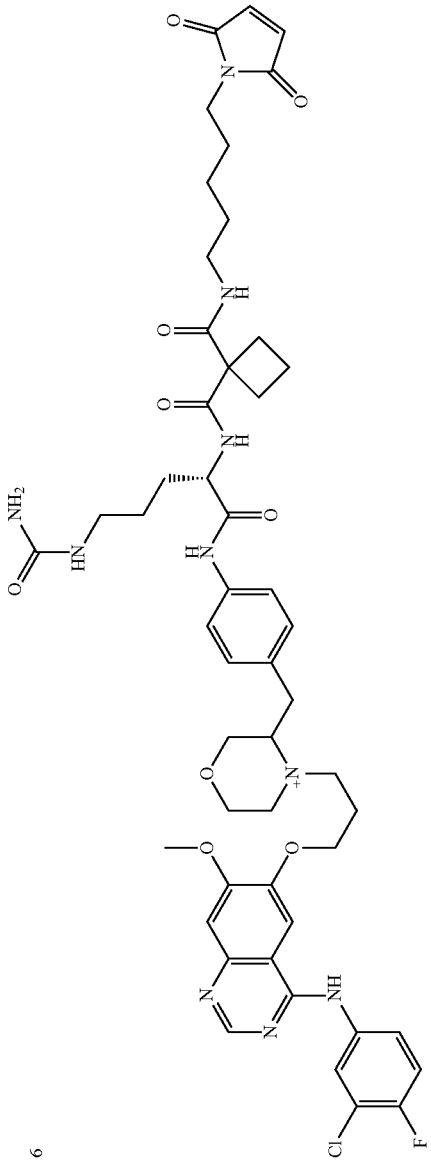 |

| Example | 7 |
|---|---|
| Structure | (chemical structure) |
| Name | (S)-4-(3-chloro-4-fluorophenylamino)-1-(4-(2-(1-(5-(2,5-dioxo-2,5-dihydro-1H-pyrrol-1-yl)pentylcarbamoyl)cyclobutanecarboxamido)-5-ureidopentanamido)benzyl)-7-methoxy-6-(3-morpholinopropoxy)quinazolin-1-ium MC-Sq-Cit-PAB-primidine-linked-gefitinib |

Sequences

NaPi2b Humanized Antibody:

In one embodiment, the Napi2b antibody of ADCs of the present invention comprises three light chain hypervariable regions and three heavy chain hypervariable regions (SEQ ID NO:1-6), the sequences of which are shown below.

In one embodiment, the Napi2b antibody of ADCs of the present invention comprises the variable light chain sequence of SEQ ID NO: 7 and the variable heavy chain sequence of SEQ ID NO: 8.

In one embodiment, the NaPi2b antibody of ADCs of the present invention comprises the light chain sequence of SEQ ID NO: 9 and the heavy chain sequence of SEQ ID NO: 10.

| | | |
|---|---|---|
| 10H1.11.4B HVR-L1 | RSSETLVHSSGNTYLE | Seq ID No: 1 |
| 10H1.11.4B HVR-L2 | RVSNRFS | Seq ID No: 2 |
| 10H1.11.4B HVR-L3 | FQGSFNPLT | Seq ID No: 3 |
| 10H1.11.4B HVR-H1 | GFSFSDFAMS | Seq ID No: 4 |
| 10H1.11.4B HVR-H2 | ATIGRVAFHTYYPDSMKG | Seq ID No: 5 |
| 10H1.11.4B HVR-H3 | ARHRGFDVGHFDF | Seq ID No: 6 |
| 10H1.11.4B VL | DIQMTQSPSSLSASVGDRVTITCRSSETLVHSSGNTYLEWYQQK PGKAPKWYRVSNRFSGVPSRFSGSGSGTDFTLTISSLQPEDFAT YYCFQGSFNPLTFGQGTKVEIKR | SEQ ID NO: 7 |
| 10H1.11.4B VH | EVQLVESGGGLVQPGGSLRLSCAASGFSFSDFAMSWVRQAPGK GLEWVATIGRVAFHTYYPDSMKGRFTISRDNSKNTLYLQMNSL RAEDTAVYYCARHRGFDVGHFDFWGQGTLVTVSS | SEQ ID NO: 8 |
| 10H1.11.4B Light Chain | DIQMTQSPSSLSASVGDRVTITCRSSETLVHSSGNTYLEWYQQK PGKAPKWYRVSNRFSGVPSRFSGSGSGTDFTLTISSLQPEDFAT YYCFQGSFNPLTFGQGTKVEIKRTVAAPSVFIFPPSDEQLKSGTA SVVCLLNNFYPREAKVQWKVDNALQSGNSQESVTEQDSKDST YSLSSTLTLSKADYEKHKVYACEVTHQGLSSPVTKSFNRGEC | SEQ ID NO: 9 |
| 10H1.11.4B Heavy Chain | EVQLVESGGGLVQPGGSLRLSCAASGFSFSDFAMSWVRQAPGK GLEWVATIGRVAFHTYYPDSMKGRFTISRDNSKNTLYLQMNSL RAEDTAVYYCARHRGFDVGHFDFWGQGTLVTVSSCSTKGPSVF PLAPSSKSTSGGTAALGCLVKDYFPEPVTVSWNSGALTSGVHTF PAVLQSSGLYSLSSVVTVPSSSLGTQTYICNVNHKPSNTKVDKK VEPKSCDKTHTCPPCPAPELLGGPSVFLFPPKPKDTLMISRTPEV TCVVVDVSHEDPEVKFNWYVDGVEVHNAKTKPREEQYNSTYR VVSVLTVLHQDWLNGKEYKCKVSNKALPAPIEKTISKAKGQPR EPQVYTLPPSREEMTKNQVSLTCLVKGFYPSDIAVEWESNGQPE NNYKTTPPVLDSDGSFFLYSKLTVDKSRWQQGNVFSCSVMHEA LHNHYTQKSLSLSPGK | SEQ ID NO: 10 |

Anti-CD33 Humanized Antibody:

In one embodiment, the anti-CD33 antibody of ADCs of the present invention comprises three light chain hypervariable regions and three heavy chain hypervariable regions, the sequences (SEQ ID NO:11-16) of which are shown below.

In one embodiment, the anti-CD33 antibody of ADCs of the present invention comprises the variable light chain sequence of SEQ ID NO: 17 and the variable heavy chain sequence of SEQ ID NO: 18.

| | | |
|---|---|---|
| 15G15.33- HVR L1 | RSSQSLLHSNGYNYLD | SEQ ID NO: 11 |
| 15G15.33- HVR L2 | LGVNSVS | SEQ ID NO: 12 |
| 15G15.33- HVR L3 | MQALQTPWT | SEQ ID NO: 13 |
| 15G15.33- HVR H1 | NHAIS | SEQ ID NO: 14 |

| | | |
|---|---|---|
| 15G15.33-HVR H2 | GIIPIFGTANYAQKFQG | SEQ ID NO: 15 |
| 15G15.33-HVR H3 | EWADVFDI | SEQ ID NO: 16 |
| 15G15.33 VL | EIVLTQSPLSLPVTPGEPASISCRSSQSLLHSNGYNYLDWYLQKPGQSPQLLIYLGVNSVSGVPDRFSGSGSGTDFTLKISRVEAEDVGVYYCMQALQTPWTFGQGTKVEIK | SEQ ID NO: 17 |
| 15G15.33 VH | QVQLVQSGAEVKKPGSSVKVSCKASGGIFSNHAISWVRQAPGQGLEWMGGIIPIFGTANYAQKFQGRVTITADESTSTAFMELSSLRSEDTAVYYCAREWADVFDIWGQGTMVTVSS | SEQ ID NO: 18 |

In one embodiment, the anti-CD33 antibody of ADCs of the present invention comprises the light chain sequence of SEQ ID NO: 19 and the heavy chain sequence of SEQ ID NO: 20.

In one embodiment, the anti-CD33 antibody of ADCs of the present invention comprises three light chain hypervariable regions and three heavy chain hypervariable regions, the sequences (Seq ID NO: 19-24) of which are shown below.

In one embodiment, the anti-CD33 antibody of ADCs of the present invention comprises the variable light chain sequence of SEQ ID NO: 25 and the variable heavy chain sequence of SEQ ID NO: 26.

In one embodiment, the anti-CD33 antibody of ADCs of the present invention comprises the variable light chain sequence of SEQ ID NO: 27 and the variable heavy chain sequence of SEQ ID NO: 28.

In one embodiment, the anti-CD33 antibody of ADCs of the present invention comprises the variable light chain sequence of SEQ ID NO: 29 and the variable heavy chain sequence of SEQ ID NO: 30.

In one embodiment, the anti-CD33 antibody of ADCs of the present invention comprises the variable light chain sequence of SEQ ID NO: 31 and the variable heavy chain sequence of SEQ ID NO: 32.

| | | |
|---|---|---|
| 9C3-HVR L1 | RASQGIRNDLG | Seq ID NO: 19 |
| 9C3-HVR L2 | AASSLQS | Seq ID NO: 20 |
| 9C3-HVR L3 | LQHNSYPWT | Seq ID NO: 21 |
| 9C3-HVR H1 | GNYMS | Seq ID NO: 22 |
| 9C3-HVR H2 | LIYSGDSTYYADSVKG | Seq ID NO: 23 |
| 9C3-HVR H3 | DGYYVSDMVV | Seq ID NO: 24 |
| 9C3 VL | DIQMTQSPSSLSASVGDRVTITCRASQGIRNDLGWYQQKPGKAPKRLIYAASSLQSGVPSRFSGSGSGTEFTLTISSLQPEDFATYYCLQHNSYPWTFGQGTKLEIK | Seq ID NO: 25 |
| 9C3 VH | EVQLVESGGALIQPGGSLRLSCVASGFTISGNYMSWVRQAPGKGLEWVSLIYSGDSTYYADSVKGRFNISRDISKNTVYLQMNSLRVEDTAVYYCVRDGYYVSDMVVWGKGTTVTVSS | Seq ID NO: 26 |
| 9C3.2 VL | DIQMTQSPSSLSASVGDRVTITCRASQGIRNDLGWYQQKPGKAPKRLIYAASSLQSGVPSRFSGSGSGTEFTLTISSLQPEDFATYYCLQHNSYPWTFGQGTKLEIK | Seq ID NO: 27 |
| 9C3.2 VH | EVQLVESGGALIQPGGSLRLSCVASGFTISGNYMSWVRQAPGKGLEWVSLIYSGDSTYYADSVKGRFTISRDISKNTVYLQMNSLRVEDTAVYYCVRDGYYVSDMVVWGKGTTVTVSS | Seq ID NO: 28 |
| 9C3.3 VL | DIQMTQSPSSLSASVGDRVTITCRASQGIRNDLGWYQQKPGKAPKRLIYAASSLQSGVPSRFSGSGSGTEFTLTISSLQPEDFATYYCLQHNSYPWTFGQGTKLEIK | Seq ID NO: 29 |
| 9C3.3 VH | EVQLVESGGALIQPGGSLRLSCVASGFTISGNYMSWVRQAPGKGLEWVSLIYSGDSTYYADSVKGRFSISRDISKNTVYLQMNSLRVEDTAVYYCVRDGYYVSDMVVWGKGTTVTVSS | Seq ID NO: 30 |

| | | |
|---|---|---|
| 9C3.4 VL | DIQMTQSPSSLSASVGDRVTITCRASQGIRNDLGWYQQ KPGKAPKRLIYAASSLQSGVPSRFSGSGSGTEFTLTISSL QPEDFATYYCLQHNSYPWTFGQGTKLEIK | Seq ID NO: 31 |
| 9C3.4 VH | EVQLVESGGALIQPGGSLRLSCVASGFTISGNYMSWVR QAPGKGLEWVSLIYSGDSTYYADSVKGRFAISRDISKN TVYLQMNSLRVEDTAVYYCVRDGYYVSDMVVWGKG TTVTVSS | Seq ID NO: 32 |

Anti-CD22 Humanized Antibody:

In one embodiment, the anti-CD22 antibody of ADCs of the present invention comprises three light chain hypervariable regions and three heavy chain hypervariable regions (SEQ ID NO: 41-46), the sequences of which are shown below.

In one embodiment, the anti-CD22 antibody of ADCs of the present invention comprises the variable light chain sequence of SEQ ID NO: 47 and the variable heavy chain sequence of SEQ ID NO: 48.

In one embodiment, the anti-CD22 antibody of ADCs of the present invention comprises the light chain sequence of SEQ ID NO: 49 and the heavy chain sequence of SEQ ID NO: 50.

| | | |
|---|---|---|
| h10F4.V3.K149C HVR-L1 | RSSQSIVHSVGNTFLE | Seq ID No: 41 |
| h10F4.V3.K149C HVR-L2 | KVSNRFS | Seq ID No: 42 |
| h10F4.V3.K149C HVR-L3 | FQGSQFPYT | Seq ID No: 43 |
| h10F4.V3.K149C HVR-H1 | GYEFSRSWMN | Seq ID No: 44 |
| h10F4.V3.K149C HVR-H2 | RIYPGDGDTNYSGKFKG | Seq ID No: 45 |
| h10F4.V3.K149C HVR-H3 | DGSSWDWYFDV | Seq ID No: 46 |
| h10F4.V3.K149C VL | DIQMTQSPSSLSASVGDRVTITCRSSQSIVHSVGNTFLEWYQQKP GKAPKLLIYKVSNRFSGVPSRFSGSGSGTDFTLTISSLQPEDFATY YCFQGSQFPYTFGQGTKVEIKR | SEQ ID NO: 47 |
| h10F4.V3.K149C VH | EVQLVESGGGLVQPGGSLRLSCAASGYEFSRSWMNWVRQAPG KGLEWVGRIYPGDGDTNYSGKFKGRFTISADTSKNTAYLQMNS LRAEDTAVYYCARDGSSWDWYFDVWGQGTLVTVSS | SEQ ID NO: 48 |
| h10F4.V3.K149C Light Chain | DIQMTQSPSSLSASVGDRVTITCRSSQSIVHSVGNTFLEWYQQKP GKAPKLLIYKVSNRFSGVPSRFSGSGSGTDFTLTISSLQPEDFATY YCFQGSQFPYTFGQGTKVEIKRTVAAPSVFIFPPSDEQLKSGTAS VVCLLNNFYPREAKVQWCVDNALQSGNSQESVTEQDSKDSTY SLSSTLTLSKADYEKHKVYACEVTHQGLSSPVTKSFNRGEC | SEQ ID NO: 49 |
| h10F4.V3.K149C Heavy Chain | EVQLVESGGGLVQPGGSLRLSCAASGYEFSRSWMNWVRQAPG KGLEWVGRIYPGDGDTNYSGKFKGRFTISADTSKNTAYLQMNS LRAEDTAVYYCARDGSSWDWYFDVWGQGTLVTVSSASTKGPS VFPLAPSSKSTSGGTAALGCLVKDYFPEPVTVSWNSGALTSGVH TFPAVLQSSGLYSLSSVVTVPSSSLGTQTYICNVNHKPSNTKVD KKVEPKSCDKTHTCPPCPAPELLGGPSVFLFPPKPKDTLMISRTP EVTCVVVDVSHEDPEVKFNWYVDGVEVHNAKTKPREEQYNST YRVVSVLTVLHQDWLNGKEYKCKVSNKALPAPIEKTISKAKGQ PREPQVYTLPPSREEMTKNQVSLTCLVKGFYPSDIAVEWESNGQ PENNYKTTPPVLDSDGSFFLYSKLTVDKSRW QQGNVFSCSVMHEALHNHYTQKSLSLSPGK | SEQ ID NO: 50 |

ADC In Vitro Data

| | | | | | | | |
|---|---|---|---|---|---|---|---|
| anti-CD22 10F4v3 LC K149C MC-Sq-Cit-PAB-Tubulysin M (ADC2-2) displays target-specific killing in BJAB and WSU-DLCL2 ||||||||
| | | BJAB IC50 || WSU-DLCL2 IC50 || Jurkat IC50 ||
| Molecule Name | DAR | nM | ng/mL | nM | ng/mL | nM | ng/mL |
| anti-CD22 10F4v3 LC K149C MC-Sq-Cit-PAB-Tubulysin M (ADC2-2) | 1.9 | 17.4 | 2610 | 0.147 | 22.05 | >133.33 | >20000 |
| Anti-Napi2b 10H1.11.4B LC K149C MC-Sq-Cit-PAB-Tubulysin M (ADC2-1) | 1.9 | >133.33 | >20000 | 83.5 | 12525 | >133.33 | >20000 |

| | | | | | | | | |
|---|---|---|---|---|---|---|---|---|
| anti-CD22 10F4v3 LC K149C MC-Sq-Cit-PAB-Dolastatin 10 (ADC1-2) displays target-specific killing in WSU-DLCL2 |||||||||
| | | | BJAB IC50 || WSU-DLCL2 IC50 || Jurkat IC50 ||
| Molecule Name | CNJ | DAR | nM | ng/mL | nM | ng/mL | nM | ng/mL |
| anti-CD22 10F4v3 LC K149C MC-Sq-Cit-PAB-Dolastatin 10 (ADC1-2) | 3048 | 1.8 | 53.0 | 7950 | 0.385 | 57.8 | 71.4 | 10710 |
| Anti-Napi2b 10H1.11.4B LC K149C MC-Sq-Cit-PAB-Dolastatin 10 (ADC1-1) | 3047 | 1.8 | >133.33 | >20000 | 44.2 | 6630 | 73.6 | 11040 |

| | | | | | | | | |
|---|---|---|---|---|---|---|---|---|
| anti-Napi2b 10H1.11.4B LC K149C MC-Sq-Cit-PAB-Tubulysin M (ADC2-1) displays target-specific killing in IGROV-1 and OVCAR-3x2.1 in the EdU Prolif assay |||||||||
| | | | IGROV-1 IC50 || OVCAR-3x2.1 IC50 || NCI-H441 IC50 ||
| Molecule Name | CNJ | DAR | nM | ng/mL | nM | ng/mL | nM | ng/mL |
| Anti-Napi2b 10H1.11.4B LC K149C MC-Sq-Cit-PAB-Tubulysin M (ADC2-1) | 3030 | 1.9 | 2.07 | 310.5 | 1.004 | 150.6 | >133.33 | >20000 |
| anti-CD22 10F4v3 LC K149C MC-Sq-Cit-PAB-Tubulysin M (ADC2-2) | 3031 | 1.9 | >133.33 | >20000 | >133.33 | >20000 | >133.33 | >20000 |

| | | | | | | | | |
|---|---|---|---|---|---|---|---|---|
| anti-Napi2b 10H1.11.4B LC K149C MC-Sq-Cit-PAB-Dolastatin 10 (ADC-1) displays target-specific killing in IGROV-1 and OVCAR-3x2.1 in the EdU Prolif assay |||||||||
| | | | IGROV-1 IC50 || OVCAR-3x2.1 IC50 || NCI-H441 IC50 ||
| Molecule Name | CNJ | DAR | nM | ng/mL | nM | ng/mL | nM | ng/mL |
| Anti-Napi2b 10H1.11.4B LC K149C MC-Sq-Cit-PAB-Dolastatin 10 (ADC1-1) | 3047 | 1.8 | 3.19 | 478.5 | 1.52 | 228.0 | 95.4 | 14310 |
| anti-CD22 10F4v3 LC K149C MC-Sq-Cit-PAB-Dolastatin 10 (ADC1-2) | 3048 | 1.8 | 114.2 | 17130 | 35.5 | 5325 | 106.5 | 15975 |

ADC In Vivo Data

The following ADCs were tested in in vivo assays described above and were found to be active. The activities of said ADCs are illustrated in FIG. 1 and the description below.

FIG. 1 shows efficacy comparison of CD22 ADCs in SCID mice with WSU-DLCL2 human diffuse large B-cell lymphoma tumors. CD22 ADC1-2 and ADC2-2 both demonstrated dose-dependent inhibition of tumor growth compared with vehicle group, and ADC1-2 displayed greater anti-tumor activity than ADC2-2. The non-binding control NaPi2b ADCs had minimal effect on the tumor growth.

What is claimed is:

1. An antibody-drug conjugate prepared by conjugating an antibody with a linker-drug intermediate compound selected from:

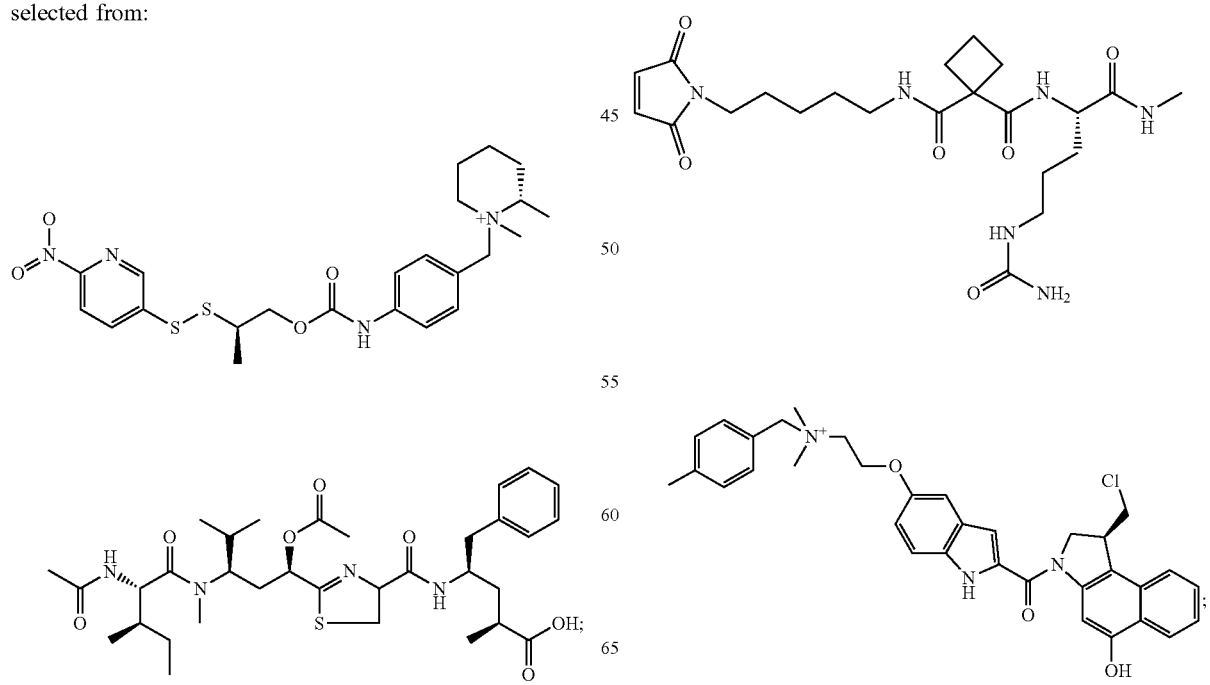

131
-continued

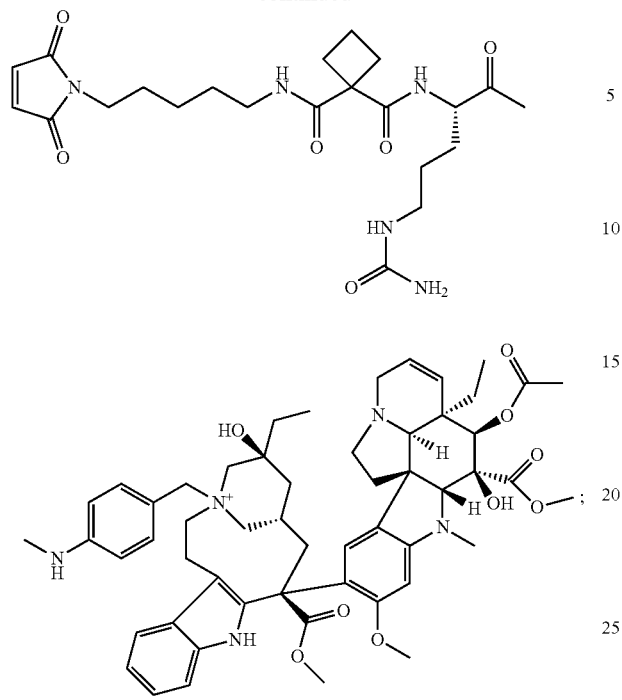

132
-continued

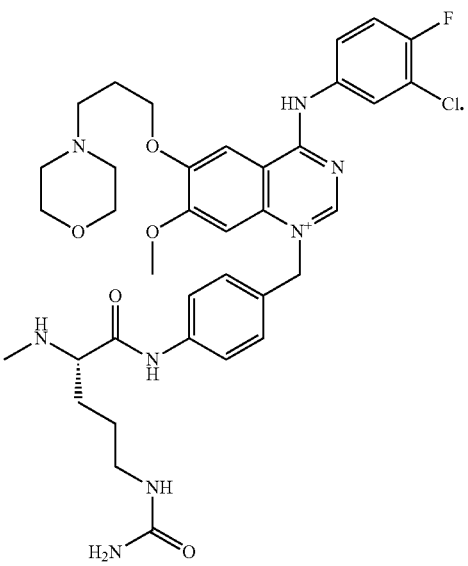

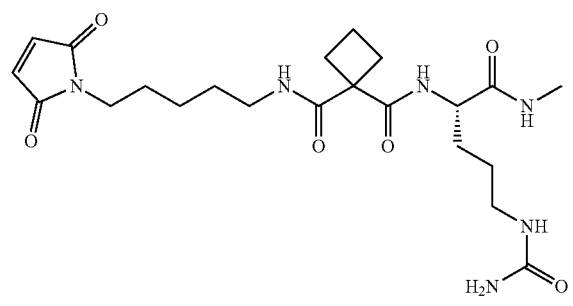

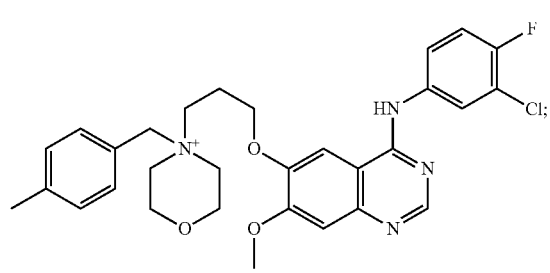

and

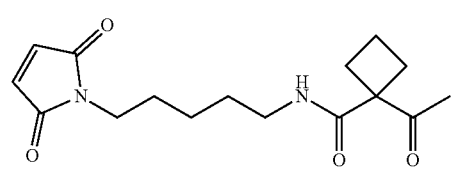

2. The antibody-drug conjugate of claim 1, wherein the antibody is a cysteine engineered antibody.

3. The antibody-drug conjugate of claim 1, wherein the antibody binds to one or more of polypeptides selected from the group consisting of: BMPR1B; E16; STEAP1; 0772P (Muc16); MPF; NaPi2b (NaPi3b); Sema 5b; PSCA hlg; ETBR; MSG783; STEAP2; TrpM4; CRIPTO; CD21; CD79b; FcRH2; HER2; NCA; MDP; IL20Rα; Brevican; EphB2R; ASLG659; PSCA; GEDA, BAFF-R; CD22; CD79a; CXCR5; HLA-DOB; P2X5; CD72; LY64; FcRH1; IRTA2; TENB2; PMEL17; TMEFF1; GDNF-Ra1; Ly6E; TMEM46; Ly6G6D; LGR5; RET; LY6K; GPR19; GPR54; ASPHD1; Tyrosinase; TMEM118; GPR172A; CD33; and CLL1.

4. The antibody-drug conjugate of claim 3, wherein the antibody binds to NaPi2b.

5. The antibody-drug conjugate of claim 4, wherein the NaPi2b antibody comprise an HVR-L1 comprising the amino acid sequence of SEQ ID NO:1, an HVR-L2 comprising the amino acid sequence of SEQ ID NO:2, an HVR-L3 comprising the amino acid sequence of SEQ ID NO:3, an HVR-H1 comprising the amino acid sequence of SEQ ID NO: 4, an HVR-H2 comprising the amino acid sequence of SEQ NO:5, and an HVR-H3 comprising the amino acid sequence of SEQ ID NO: 6.

6. The antibody-drug conjugate of claim 5, wherein said NaPi2b antibody comprises a VL domain comprising the amino acid sequence of SEQ NO:7 and a VH domain comprising the amino acid sequence of SEQ ID NO:8.

7. The antibody-drug conjugate of claim 5, wherein said NaPi2b antibody comprises an amino acid sequence of SEQ ID NO:9 and an amino acid sequence of SEQ ID NO: 10.

8. The antibody-drug conjugate of claim 5, wherein said NaPi2b antibody comprises an amino acid sequence that has at least 95% sequence identity with amino acid sequence of SEQ ID NO:9 and that comprises an amino acid sequence that has at least 95% sequence identity with an amino acid sequence of SEQ ID NO: 10.

9. The antibody-drug conjugate of claim 3, wherein the antibody binds to CD22.

10. The antibody-drug conjugate of claim 9, wherein the CD22 antibody comprise an HVR-L1 comprising the amino acid sequence of SEQ ID NO:41, an HVR-L2 comprising the amino acid sequence of SEQ ID NO:42, an HVR-L3 comprising the amino acid sequence of SEQ ID NO:43, an HVR-H1 comprising the amino acid sequence of SEQ ID NO: 44, an HVR-H2 comprising the amino acid sequence of SEQ ID NO:45, and an HVR-H3 comprising the amino acid sequence of SEQ ID NO: 46.

11. The antibody-drug conjugate of claim 9, wherein said CD22 antibody comprises a VL domain comprising the amino acid sequence of SEQ ID NO:47 and a VH domain comprising the amino acid sequence of SEQ ID NO:48.

12. The antibody-drug conjugate of claim 9, wherein said CD22 antibody comprises an amino acid sequence of SEQ ID NO:49 and an amino acid sequence of SEQ ID NO: 50.

13. The antibody-drug conjugate of claim 9, wherein said CD22 antibody comprises an amino acid sequence that has at least 95% sequence identity with amino acid sequence of SEQ ID NO:49 and that comprises an amino acid sequence that has at least 95% sequence identity with an amino acid sequence of SEQ ID NO: 50.

14. A pharmaceutical composition comprising the antibody-drug conjugate of claim 1 and a pharmaceutically acceptable carrier thereof.

15. The antibody-drug conjugate of claim 1 wherein the linker-drug intermediate compound has the structure:

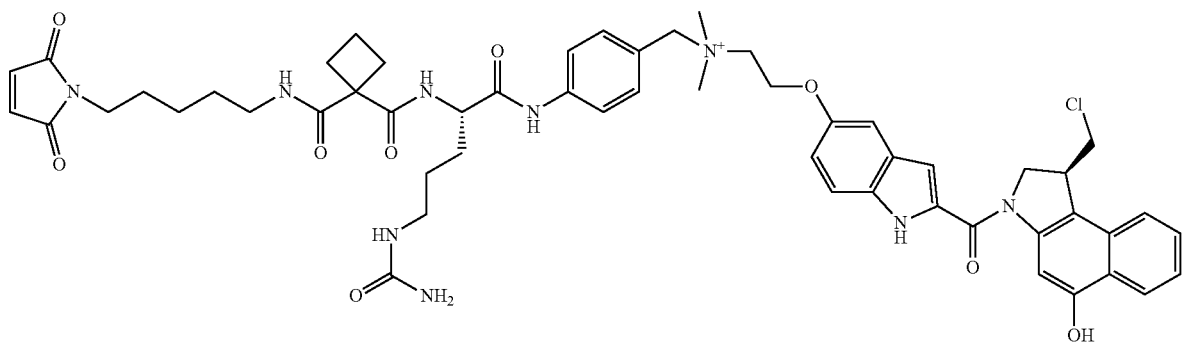

16. The antibody-drug conjugate of claim 1 wherein the linker-drug intermediate compound has the structure:

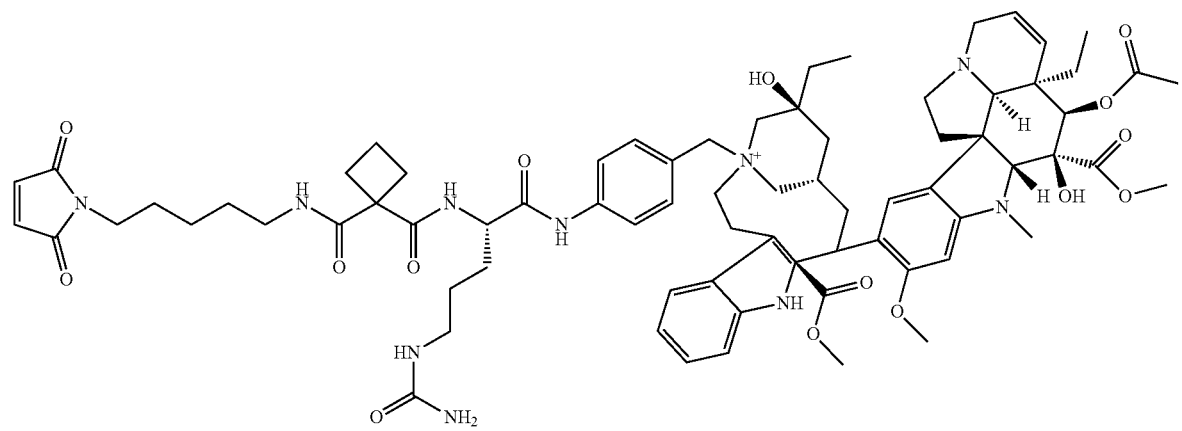

17. The antibody-drug conjugate of claim 1 wherein the linker-drug intermediate compound has the structure:
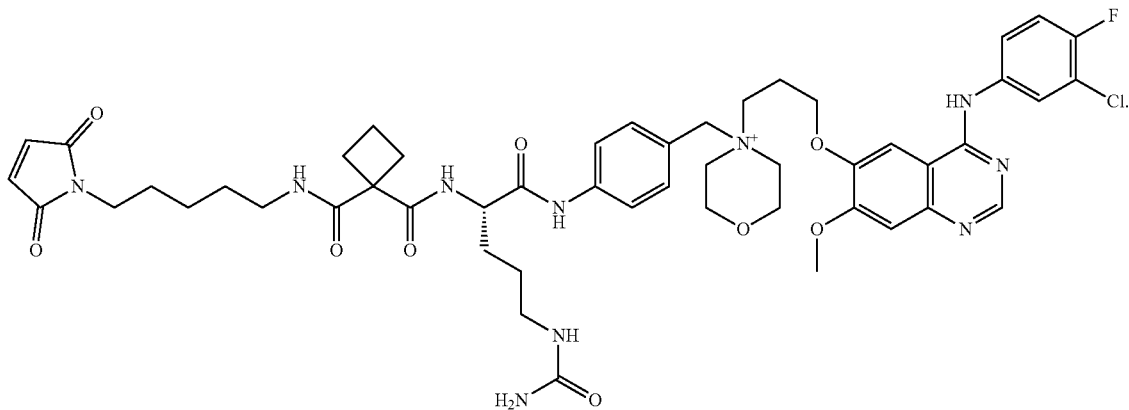 [SMILES: COc1cc2ncnc(Nc3ccc(F)c(Cl)c3)c2cc1OCCC[N+]1(Cc2ccc(NC(=O)[C@H](CCCNC(N)=O)NC(=O)C3(C(=O)NCCCCCN4C(=O)C=CC4=O)CCC3)cc2)CCOCC1]
18. The antibody-drug conjugate of claim 1 wherein the linker-drug intermediate compound has the structure:
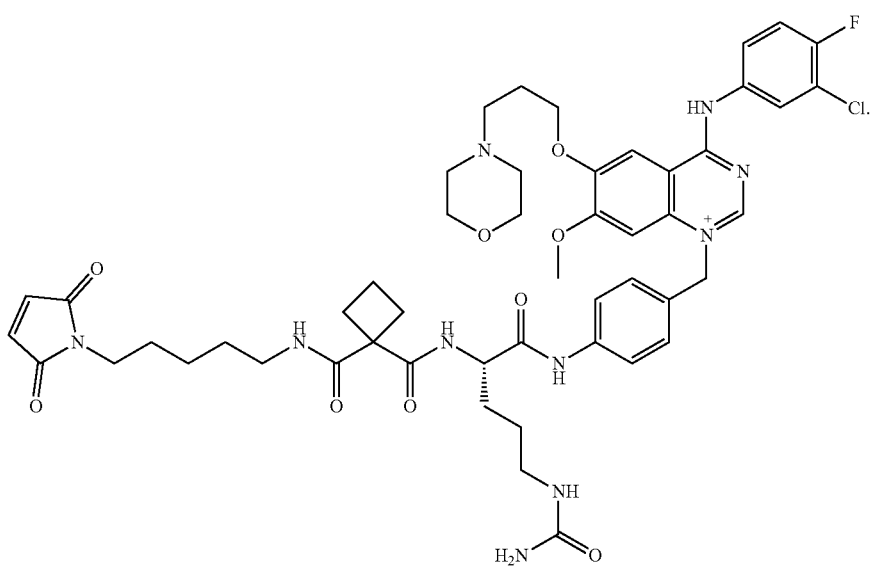
\* \* \* \* \*